(12) United States Patent
Bottomley et al.

(10) Patent No.: US 12,415,838 B2
(45) Date of Patent: Sep. 16, 2025

(54) MODIFIED MENINGOCOCCAL fHbp POLYPEPTIDES

(71) Applicant: GLAXOSMITHKLINE BIOLOGICALS SA, Rixensart (BE)

(72) Inventors: Matthew Bottomley, Siena (IT); Enrico Malito, Siena (IT); Manuele Martinelli, Siena (IT); Maria Scarselli, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 18/440,212

(22) Filed: Feb. 13, 2024

(65) Prior Publication Data

US 2024/0218026 A1    Jul. 4, 2024

Related U.S. Application Data

(62) Division of application No. 17/245,681, filed on Apr. 30, 2021, now Pat. No. 11,932,671, which is a division of application No. 16/458,365, filed on Jul. 1, 2019, now Pat. No. 11,021,522, which is a division of application No. 15/120,674, filed as application No. PCT/EP2015/054174 on Feb. 27, 2015, now Pat. No. 10,392,424.

(30) Foreign Application Priority Data

Feb. 28, 2014 (EP) ..................... 14157399
Jul. 17, 2014 (EP) ..................... 14177566

(51) Int. Cl.
  *A61K 39/02*   (2006.01)
  *A61K 39/095*  (2006.01)
  *C07K 14/22*   (2006.01)
  *A61K 39/00*   (2006.01)

(52) U.S. Cl.
  CPC ............ *C07K 14/22* (2013.01); *A61K 39/095* (2013.01); *A61K 2039/523* (2013.01); *A61K 2039/55511* (2013.01); *A61K 2039/70* (2013.01)

(58) Field of Classification Search
  None
  See application file for complete search history.

(56) References Cited

U.S. PATENT DOCUMENTS

| | | | |
|---|---|---|---|
| 10,392,424 B2 | 8/2019 | Bottomley et al. | |
| 11,021,522 B2 | 6/2021 | Bottomley et al. | |
| 11,066,450 B2 | 7/2021 | Bottomley et al. | |
| 11,707,513 B2 | 7/2023 | Biolchi et al. | |
| 2006/0251670 A1 | 11/2006 | Comanducci et al. | |
| 2007/0020624 A1 | 1/2007 | Rubenfield et al. | |
| 2007/0027309 A1 | 2/2007 | Weinstock et al. | |
| 2008/0063665 A1 | 3/2008 | Oster et al. | |
| 2017/0008933 A1 | 1/2017 | Bottomley et al. | |
| 2017/0226161 A1 | 8/2017 | Bottomley et al. | |
| 2018/0214531 A1 | 8/2018 | Biolchi et al. | |
| 2021/0253617 A1 | 8/2021 | Hoelzl et al. | |
| 2021/0253647 A1 | 8/2021 | Bottomley et al. | |

FOREIGN PATENT DOCUMENTS

| | | |
|---|---|---|
| CN | 102816217 A | 12/2012 |
| CN | 104602704 A | 5/2015 |
| CN | 106795208 A | 5/2017 |
| JP | 2006-521782 A | 9/2006 |
| JP | 2017-502625 A | 2/2015 |
| JP | 2017512060 A | 5/2017 |
| JP | 6687597 B2 | 4/2020 |
| WO | 2001052885 A1 | 7/2001 |
| WO | 2004048404 A2 | 6/2004 |
| WO | 2006024954 A2 | 3/2006 |
| WO | 2007060548 A2 | 5/2007 |
| WO | 2008079372 A2 | 7/2008 |
| WO | 2011051893 A1 | 5/2011 |
| WO | 2011110634 A1 | 9/2011 |
| WO | 2011126863 A1 | 10/2011 |
| WO | 2012032169 A1 | 3/2012 |
| WO | 2013079970 A1 | 6/2013 |
| WO | 2013186753 A1 | 12/2013 |
| WO | 2014030003 A1 | 2/2014 |
| WO | 2015128480 A1 | 9/2015 |
| WO | 2016008960 A1 | 1/2016 |
| WO | 2016008961 A1 | 1/2016 |

OTHER PUBLICATIONS

Muriel et al., "Neisseria meningitidis recruits factor H using protein mimicry of host carbohydrates", Nature, vol. 458, No. 7240, Apr. 16, 2009 (Apr. 16, 2009), pp. 890-893.

European Patent Office as International Searching Authority, International Search Report and Written Opinion for International Appl. No. PCT/EP2015/054174 (published as WO 2015128480), dated Jul. 15, 2015, 11 pages.

European Patent Office, priority search results and written opinion received for corresponding EP Appl. No. 14 17 7566, (16 pages) dated Nov. 21, 2014.

Mar. 10, 2016 (Mar. 10, 2016), "N. meningitidis mature truncated mutant fHbp protein S32V/L 126R, Seq 44.", retrieved from EBI accession No. GSP:BCL30499 Database accession No. BCL30499 ; & Database Geneseq [Online].

Mar. 10, 2016 (Mar. 10, 2016), "N. meningitidis mature truncated mutant fHbp protein S32V/L 123R, Seq 45.", retrieved from EBI accession No. GSP:BCL30500 Database accession No. BCL30500 ; & Database Geneseq [Online].

Mar. 10, 2016 (Mar. 10, 2016), "N. meningitidis M1239 mature truncated mutant fHbp protein L 126R, Seq 56.", retrieved from EBI accession No. GSP:BCL30511 Database accession No. BCL30511 ; & Database Geneseq [Online].

Mar. 10, 2016 (Mar. 10, 2016), "N. meningitidis 2996 mature truncated mutant fHbp protein L 123R, Seq 54.", retrieved from EBI accession No. GSP:BCL30509 Database accession No. BCL30509 ; & Database Geneseq [Online].

(Continued)

*Primary Examiner* — Jennifer E Graser

(57) ABSTRACT

Modified meningococcal fHbp polypeptides with increased stability.

18 Claims, 5 Drawing Sheets

Specification includes a Sequence Listing.

(56) References Cited

OTHER PUBLICATIONS

Mar. 10, 2016 (Mar. 10, 2016), "Neisseria meningitidis mutant fHbp fusion protein sequence B, Seq ID 30.", retrieved from EBI accession No. GSP:BCL30485 Database accession No. BCL30485.
International Search Report and Written Opinion for International Application No. PCT/EP2015/054174 (published as WO 2015/128480) dated Sep. 3, 2015 (11 total pages).
Bork et al. (Molecular and Cellular Biology) 1988, 8:1247-1252.
Database UniProt [Online] Feb. 22, 2012 (Feb. 22, 2012), "SubName: Full= Factor H binding protein variant A93_001 (ECO:0000313: EMBL: AEV41632.1}; Flags: Fragment;", retrieved from EBI accession No. Uniprot: 39I6U8 Database accession No. G9I6U8 sequence.
Database Geneseq [Online] Sep. 4, 2008 (Sep. 4, 2008), "Neisseria ORF2086 subfamily A protein, Seq ID No. 6.", XP055141124, retrieved from EBI accession No. GSP:ASQ06840 Database accession No. ASQ06840 sequence.
Assessment report of Bexsero (common name "Meningococcal group B Vaccine (rDNA, component, adsorbed)") by the European Medicines Agency (Committee for Medicinal Products for Human Use (CHMP)); Procedure No. EMEA/H/C/002333; dated Nov. 15, 2012, available online at http://www.ema.europa.eu/docs/en GB/documentlibrary/EPAR_-_Public_assessment_report/human/002333/WC500137883.pdf; retrieved on Dec. 16, 2016; 102 total pages.
Beernink, et al., A meningococcal factor H binding protein mutant that eliminates factor H binding enhances protective antibody responses to vaccination, 2011 J. Immunol. 186(6):3606-3614.
Beernink, et al., "Fine Antigenic Specificity and Cooperative Bactericidal Activity of Monoclonal Antibodies Directed at the Meningococcal Vaccine Candidate for Factor H-Binding Protein" Infection and Immunity 76(9):4232-4240.
Beernink et al., Impaired immunogenicity of a meningococcal factor H-binding protein vaccine engineered to eliminate factor H binding. Clin Vaccine Immunol. Jul. 2010; 17(7):1074-8.
Beernink et al., Rapid Genetic Grouping of Factor H-Binding Protein (Genome-Derived Neisserial Antigen 1870), a Promising Group B Meningococcal Vaccine Candidate, 2006 Clinical and Vaccine Immunology 13(7): 758-763.
Beernink et al: "The Effect of Human Factor H on Immunogenicity of Meningococcal Native Outer Membrane Vesicle Vaccines with Over-Expressed Factor H Binding Protein", PLOS Pathogens, vol. 8, No. 5, May 10, 2012, pp. e1002688-e1002688 (9 total pages).
Beernink & Granoff, The modular architecture of meningococcal factor H-binding protein, 2009 Microbiology 155:2873-2883.
Bork, "Powers and Pitfalls in Sequence Analysis: The 70% Hurdle", Genome Research; 10(4); 398-400; 2000.
Bowie et al., "Deciphering the message in protein sequences: tolerance to amino acid substitutions", Science, 1990, 257:1306-1310; 1990.
Brehony, et al., Variation of the factor H-binding protein of Neisseria meningitidis, 2009, Microbiology 155:4155-4169.
Burgess et al., "Possible dissociation of the heparin-binding and mitogenic activities of heparin-binding (acidic fibroblast) growth factor-1 from its receptor-binding activities by site-directed mutagenesis of a single lysine residue", J. of Cell Bio. 111:2129-2138; 1990.
Esposito Susanna et al: "A phase 2 randomized controlled trial of a multicomponent meningococcal serogroup B vaccine, 4CMenB, in infants (II)", Human Vaccines & Immunotherapeutics Jul. 2014, vol. 10, No. 7, Jul. 11, 2014(Jul. 11, 2014), pp. 2005-2014.
Giuntini et al., "Monoclonal Antibodies to Meningococcal Factor H Binding Protein with Overlapping Epitopes and Discordant Functional Activity", PLOS One, vol. 7, No. 3; pp. e34272-e34272 (2012).
Granoff et al., "Chapter 21 Section: Two: Licensed vaccines—Meningococcal vaccines" in "Vaccines (6th Edition)", Jan. 1, 2013 (Jan. 1, 2013), Elsevier, XP055150061, ISBN: 978-1-45-570090-5; pp. 388-418.

Granoff et al., Does binding of complement factor H to the meningococcal vaccine antigen, factor H binding protein, decrease protective serum antibody responses? Clin Vaccine Immunol. Aug. 2013;20(8):1099-1107.
Greenspan et al., "Defining epitopes: it's not as easy as it seems", Nature Biotechnology 17: 936-937, 1999.
Jacobsson et al., "Prevalence and sequence variations of the genes encoding the five antigens included in the novel 5CVMB vaccine covering group B meningococcal disease", Vaccine, 27:10; pp. 1579-1584 (2009).
Johnson et al., Design and evaluation of meningococcal vaccines through structure-based modification of host and pathogen molecules. PLoS Pathog. 2012;8(10):e1002981.
Koeberling et al., "Meningococcal outer membrane vesicle vaccines derived from mutant strains engineered to express factor H binding proteins from antigenic variant groups 1 and 2", Clinical and Vaccine Immunology, American Society for Microbiology, Washington, DC, US, vol. 16, No. 2, Feb. 1, 2009, pp. 156-162.
Lazar et al., "Transforming growth factor alpha: mutation of aspartic acid 47 and leucine 48 results in different biological activities", Molecular and Cellular Biology; 8(3); 1247-1252; 1988.
Lucidarme, J. sequence entitled "Factor H-binding protein" published as UniProtKB Accession No. D3JZH2, dated Mar. 23, 2010, available at http://www.uniprot.org/uniprot/D3JZH2.txt?version=1.
Lucidarme, J. sequence entitled "Factor H-binding protein" published as UniProtKB Accession No. D3JZI3, dated Mar. 23, 2010, available at http://www.uniprot.org/uniprot/D3JZI3.txt?version=1.
Masignani et al., Vaccination against Neisseria meningitidis using three variants of the lipoprotein GNA1870. J Exp Med. Mar. 17, 2003;197(6):789-99.
McGuinness et al., Lancet 337:514-517, 1991.
McGuinness et al., Mol. Microbiol. 7:505-514, 1993.
Mikayama, et al., Nov. 1993, Proc. Natl. Acad. Sci. USA, vol. 90: 10056-10060).
Murphy, E. sequence entitled "Factor H binding protein variant A93_001" published as UniProtKB Accession No. G9I6U8, dated Feb. 22, 2012, available at http://www.uniprot.org/uniprot/G916U8.txt?version= 1.
Pajon et al., Design of meningococcal factor H binding protein mutant vaccines that do not bind human complement factor, H. Infect Immun. Aug. 2012;80(8):2667-77.
PENG Shi-ze, et al., Expression and Immunological Analysis of Recombinant Nessaria Meningitis Group B Recombinant fHBP Fusion Protein, China Biotechnology, 2010, p. 28-33, vol. 31(5) (English Language Abstract).
Peeters, et al., "Phase I clinical trial with a hexavalent PorA containing meningococcal outer membrane vesicle vaccine", Vaccine, vol. 14, No. 10, pp. 1009-1015, 1996.
Romanelli, et al. sequence entitled "Factor H binding protein" published as UniProtKB Accession No. L0GGE0, dated Mar. 6, 2013, available at http://www.uniprot.org/uniprot/LOGGEO.txt?version=1.
Romanelli, et al. sequence entitled "Factor H binding protein" published as UniProtKB Accession No. L0GFA3, dated Mar. 6, 2013, available at http://www.uniprot.org/uniprot/LOGFA3.txt?version=1.
Rossi et al., Meningococcal factor H-binding protein vaccines with decreased binding to human complement factor H have enhanced immunogenicity in human factor H transgenic mice. Vaccine. Nov. 4, 2013;31(46):5451-7.
Rudinger J. In: Peptide Hormones. (Ed) JA Parsons, University Park Press, pp. 1-7, 1976.
Schneider et al., Neisseria meningitidis recruits factor H using protein mimicry of host carbohydrates. Nature. Apr. 16, 2009;458(7240):890-893.
Skolnick, et al., Trends in Biotechnology 18, 34-39, 2000.
Snape, et al., "Immunogenicity of two investigational serogroup B meningococcal vaccines in the first year of life: a randomized comparative trial", Pediatr. Infect. Dis. J., 29(11), pp. e71-e79, Nov. 2010.
Van Der Veen et al., Nonfunctional variant 3 factor H binding proteins as meningococcal vaccine candidates. Infect Immun. Mar. 2014; 82(3):1157-63.

(56) References Cited

OTHER PUBLICATIONS

Vermont, C.L., et al., "Cross-Reactivity of Antibodies agaisnt PorA after Vaccination with a Meningococcal B Outer Membrane Vesicle Vaccine", Infection and Immunity, Apr. 2003, p. 1650-1655.

Zlotnick, G. W.; sequence described as "Neisseria ORF2086 subfamily A protein" corresponding to Seq ID No. 6 of international patent application publication WO2008079372; sequence published as Geneseq Accession No. ASQ06840, dated Sep. 4, 2008.

International Search Report and Written Opinion for Application No. PCT/EP2015/066228 dated Aug. 26, 2015, by the European Patent Office as International Searching Authority, 14 pages total.

International Search Report and Written Opinion for Application No. PCT/EP2015/066229 dated Jan. 10, 2015, by the European Patent Office as International Searching Authority, 15 pages total.

Intellectual Property Office of Singapore, Written Opinion dated Jan. 26, 2018 for Singapore Appl. No. 11201610945P (based on Inl'l. Appl. No. PCT/EP2015/066229 filed Jul. 16, 2015); 8 total pages.

European Patent Office, office action received for corresponding EP Appl. No. 15 707 351.1 (published as EP3110442), dated Aug. 8, 2017, 5 total pages.

European Patent Office, priority search results and written opinion received for corresponding EP Appl. No. 14 15 7399, (8 pages) dated Sep. 18, 2014.

Murphy E., et al., "Sequence Diversity of the Factor H Binding Protein Vaccine Candidate in Epidemiologically Relevant Strains of Serogroup B Neisseria Meningitidis, "Journal of Infectious Diseases, 2009, vol. 200, pp. 379-389.

MODIFIED MENINGOCOCCAL fHbp POLYPEPTIDES

CROSS-REFERENCE TO RELATED APPLICATIONS

This application is a Divisional of U.S. patent application Ser. No. 17/245,681, filed Apr. 30, 2021, which is a Divisional of U.S. patent application Ser. No. 16/458,365, filed Jul. 1, 2019, now issued as U.S. Pat. No. 11,021,522 on May 12, 2021, which is a Divisional of U.S. patent application Ser. No. 15/120,674, filed Aug. 22, 2016, now issued as U.S. Pat. No. 10,392,424 on Aug. 7, 2019, which is the U.S. National Stage Application submitted under 35 U.S.C. § 371 of International Application No. PCT/EP2015/054174, filed Feb. 27, 2015, which claims the benefit of European patent applications 14157399.8 (filed Feb. 28 2014) and 14177566.8 (filed Jul. 17 2014), the complete contents of which are hereby incorporated herein by reference for all purposes.

REFERENCE TO SEQUENCE LISTING

The instant application contains a Sequence Listing which has been submitted electronically in XML file format and is hereby incorporated by reference in its entirety. Said XML copy, created on Jan. 30, 2024, is named VN56080D3-US_SL.xml and is 74,750 bytes in size.

TECHNICAL FIELD

This invention is in the field of protein engineering, relating in particular to the meningococcal factor H binding protein (fHbp), which is known to be a useful vaccine immunogen.

BACKGROUND ART

*Neisseria meningitidis* is a Gram-negative encapsulated bacterium which colonises the upper respiratory tract of approximately 10% of human population. Conjugate vaccines are available against serogroups A, C, W135 and Y, but the only vaccine which is available for protecting against serogroup B in a two-dose regimen is the BEXSERO™ product which was approved in 2013.

One of the protective immunogens in BEXSERO™ is fHbp, which has also been known as protein '741' (SEQ ID NO: 2536 in ref. 1; SEQ ID 1 herein), 'NMB1870', 'GNA1870' [2-4, 'P2086', 'LP2086' or 'ORF2086' [5-7]. The 3D structure of this protein is known [8,9], and the protein has two β-barrels connected by a short linker. Many publications have reported on the protective efficacy of this protein in meningococcal vaccines e.g. see references 10-14. The fHbp lipoprotein is expressed in various strains across all serogroups. fHbp sequences have been grouped into three variants [2] (referred to herein as v1, v2 and v3), and it has been found in general that serum raised against a given variant is bactericidal against strains which express that variant, but is not active against strains which express one of the other two variants i.e. there is intra-variant cross-protection, but not inter-variant cross-protection (except for some v2 and v3 cross-reactivity).

To increase inter-family cross-reactivity the fHbp sequence has been engineered to contain specificities for all three variants [15]. Protein engineering has also been used to remove fHbp's interaction with siderophores [16] and with factor H [17-25]. Disruption of the interaction with fH has been reported for all three variants and is postulated to provide a superior vaccine immunogen ×[22,26]. For v2 polypeptides, however, references 23 and 24 report an inherent instability which is also seen in mutants with disrupted fH-binding. The instability appears to arise from the N-terminal β-barrel domain, and reference 23 warns that any substitutions in this barrel might promote instability.

It is an object of the invention to provide further fHbp v2 and v3 mutants, but having enhanced stability.

DISCLOSURE OF THE INVENTION

Full-length fHbp from strain 2996 in v2 has the following amino acid sequence (SEQ ID NO: 2):
<u>MNRTAFCCLSLTAALILTA</u>CSSGGGGVAADIGAGLADALTAPLDHKDKS

LQSLTLDQSVRKNEKLKLAAQGAEKTYGNGDSLNTGKLKNDKVSRFDFI

RQIEVDGQLITLESGEFQIYKQDHSAVVALQIEKINNPDKIDSLINQRS

FLVSGLGGEHTAFNQLPDGKAEYHGKAFSSDDAGGKLTYTIDFAAKQGH

GKIEHLKTPEQNVELAAAELKADEKSHAVILGDTRYGSEEKGTYHLALF

GDRAQEIAGSATVKIGEKVHEIGIAGKQ

The mature lipoprotein lacks the first 19 amino acids of SEQ ID NO: 2 (underlined; provides SEQ ID NO: 4), and the ΔG form of SEQ ID NO: 2 lacks the first 26 amino acids (SEQ ID NO: 5).

Full-length fHbp from strain M1239 in v3 has the following amino acid sequence (SEQ ID NO: 3):
<u>MNRTAFCCLSLTTALILTA</u>CSSGGGGSGGGGVAADIGTGLADALTAPLD

HKDKGLKSLTLEDSIPQNGTLTLSAQGAEKTFKAGDKDNSLNTGKLKND

KISRFDFVQKIEVDGQTITLASGEFQIYKQNHSAVVALQIEKINNPDKT

DSLINQRSFLVSGLGGEHTAFNQLPGGKAEYHGKAFSSDDPNGRLHYSI

DFTKKQGYGRIEHLKTLEQNVELAAAELKADEKSHAVILGDTRYGSEEK

GTYHLALFGDRAQEIAGSATVKIGEKVHEIGIAGKQ

The mature lipoprotein lacks the first 19 amino acids of SEQ ID NO: 3 (underlined; provides SEQ ID NO: 40), and the ΔG form of SEQ ID NO: 3 lacks the first 31 amino acids (SEQ ID NO: 17).

The inventors have identified residues within SEQ ID NO: 2 and SEQ ID NO: 3 which can be modified to increase the polypeptide's stability. These residues are generally present across v2 and v3 sequences and so their modification can provide v2 and v3 fHbp sequences with enhanced stability. Moreover, the inventors have shown that, as well as increasing stability, mutation of these residues can advantageously decrease binding to human factor H (fH). In addition, however, the mutations disclosed herein can be combined with other mutations e.g. to decrease binding to human factor H (fH), for which several mutations are already known in the art.

Thus, in general the invention provides a mutant v2 or v3 fHbp which has increased stability relative to a wild-type fHbp (e.g. relative to SEQ ID NOs: 2 or 3) and which, optionally, has lower affinity for human factor H than a wild-type fHbp (e.g. relative to SEQ ID NOs: 2 or 3). The increase in stability and the optional reduction in fH affinity preferably result from the same mutation(s), but in some embodiments they may be due to the separate effect of combined mutations. Mutant fHbp proteins with both increased stability and reduced fH affinity are preferred.

In a first embodiment the invention provides a polypeptide comprising a mutant fHbp v2 amino acid sequence, wherein: (a) the amino acid sequence has at least k % sequence identity to SEQ ID NO: 5, and/or comprises a fragment of SEQ ID NO: 5; but (b) the amino acid sequence differs from SEQ ID NO: 5 at one or more of the following residues: S32, V33, L39, L41, F69, V100, I113, F122, L123, V124, S125, G126, L127, G128, S151, H239, and/or E240.

Where feature (a) relates to a fragment, the fragment will include at least one of the residues listed in (b), but that residue will differ when compared to that residue in SEQ ID NO: 5. A fragment of (a) will generally be at least 7 amino acids long e.g. 8, 10, 12, 14, 16, 18, 20, 22, 24, 26, 28, 30, 32, 24, 26, 28, 40, 45, 50, 55, 60 contiguous amino acids or more from SEQ ID NO: 5. The fragment will typically include at least one epitope from SEQ ID NO: 5. Epitope identification and mapping is established for fHbp [11; 27-31]. Sharing at least 30 contiguous amino acids with SEQ ID NO: 5 will be typical, and usually a mutant fHbp v2 amino acid sequence will include several (e.g. 2, 3, 4, 5 or more) fragments from SEQ ID NO: 5. Overall, a mutant fHbp v2 amino acid sequence can have at least k % sequence identity to and include several fragments of SEQ ID NO: 5.

The value of k may be selected from 80, 85, 86, 87, 88, 89, 90, 91, 92, 93, 94, 95, 96, 97, 98, 99 or more. It is preferably 90 (i.e. the mutant fHbp v2 amino acid sequence has at least 90% identity to SEQ ID NO: 5) and is more preferably 95.

The polypeptide can, after administration to a host animal, elicit antibodies which can recognise a wild-type meningococcal polypeptide consisting of SEQ ID NO: 4. These antibodies are ideally bactericidal (see below). These antibodies can include some antibodies which do not recognise a v1 or a v3 polypeptide (e.g. a wild-type meningococcal polypeptide consisting of SEQ ID NO: 46 and a wild-type meningococcal polypeptide consisting of SEQ ID NO: 40), although they may also include some antibodies which cross-react with v1 and/or v3 polypeptides.

The polypeptide has, under the same experimental conditions, a higher stability than the same polypeptide but without the sequence difference/s of (b) e.g. higher stability than a wild-type meningococcal polypeptide consisting of SEQ ID NO: 4. The stability enhancement can be assessed using differential scanning calorimetry (DSC) e.g. as discussed in references 32 & 33. DSC has previously been used to assess the stability of v2 fHbp [24]. Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

In some embodiments, the polypeptide of the invention is truncated relative to SEQ ID NO: 5. Compared to the wild-type mature sequence, SEQ ID NO: 5 is already truncated at the N-terminus up to and including the polyglycine sequence (compare SEQ ID NOs: 4 and 5), but SEQ ID NO: 5 can be truncated at the C-terminus and/or further truncated at the N-terminus.

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur even below 40° C. with wild-type v2 sequences [24] (whereas C-terminal domains can have a Tm of 80° C. or more). Thus the mutant fHbp v2 amino acid sequence of the invention preferably has a N-terminal domain with a Tm of at least 45° C. e.g. ≥50° C., ≥55° C., ≥60° C., ≥65° C., ≥70° C., ≥75° C., or even ≥80° C.

In a second embodiment, the invention provides a polypeptide comprising a mutant fHbp v3 amino acid sequence, wherein: (a) the amino acid sequence has at least j % sequence identity to SEQ ID NO: 17, and/or comprises a fragment of SEQ ID NO: 17; but (b) the amino acid sequence differs from SEQ ID NO: 17 at one or more of the following residues: S32, I33, L39, L41, F72, V103, T116, F125, L126, V127, S128, G129, L130, G131, S154, H242, and/or E243.

Where feature (a) relates to a fragment, the fragment will include at least one of the residues listed in (b), but that residue will differ when compared to that residue in SEQ ID NO: 17. A fragment of (a) will generally be at least 7 amino acids long e.g. 8, 10, 12, 14, 16, 18, 20, 22, 24, 26, 28, 30, 32, 24, 26, 28, 40, 45, 50, 55, 60 contiguous amino acids or more from SEQ ID NO: 17. The fragment will typically include at least one epitope from SEQ ID NO: 17. Epitope identification and mapping is established for fHbp [11; 27-31]. Sharing at least 30 contiguous amino acids with SEQ ID NO: 17 will be typical, and usually a mutant fHbp v3 amino acid sequence will include several (e.g. 2, 3, 4, 5 or more) fragments from SEQ ID NO: 17. Overall, a mutant fHbp v3 amino acid sequence can have at least j % sequence identity to and include several fragments of SEQ ID NO: 17.

The value of j may be selected from 80, 85, 86, 87, 88, 89, 90, 91, 92, 93, 94, 95, 96, 97, 98, 99 or more. It is preferably 90 (i.e. the mutant fHbp v3 amino acid sequence has at least 90% identity to SEQ ID NO: 17) and is more preferably 95.

The polypeptide can, after administration to a host animal, elicit antibodies which can recognise a wild-type meningococcal polypeptide consisting of SEQ ID NO: 40. These antibodies are ideally bactericidal (see below). These antibodies can include some antibodies which do not recognise a v1 or a v2 polypeptide (e.g. a wild-type meningococcal polypeptide consisting of SEQ ID NO: 46 and a wild-type meningococcal polypeptide consisting of SEQ ID NO: 4), although they may also include some antibodies which cross-react with v1 and/or v2 polypeptides.

The polypeptide has, under the same experimental conditions, a higher stability than the same polypeptide but without the sequence difference/s of (b) e.g. higher stability than a wild-type meningococcal polypeptide consisting of SEQ ID NO: 40. The stability enhancement can be assessed using differential scanning calorimetry (DSC) e.g. as discussed in references 32 & 33 DSC has previously been used to assess the stability of v3 fHbp [23]. Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

In some embodiments, the polypeptide of the invention is truncated relative to SEQ ID NO: 17. Compared to the wild-type mature sequence, SEQ ID NO: 17 is already truncated at the N-terminus up to and including the polyglycine sequence (compare SEQ ID NOs: 40 and 17), but SEQ ID NO: 17 can be truncated at the C-terminus and/or further truncated at the N-terminus.

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur at around 60° C. or less with wild-type v3 sequences [24] (whereas C-terminal domains can have a Tm of 80° C. or more). Thus the mutant fHbp v3 amino acid sequence of the invention preferably has a N-terminal domain with a Tm of at least 65° C. e.g. ≥70° C., ≥75° C., or even ≥80° C.

Mutations relative to SEQ ID NO: 5 Polypeptides of the first embodiment of the invention comprise an amino acid sequence which has at least k % identity to SEQ ID NO: 5, and/or comprise a fragment of SEQ ID NO: 5. In comparison to SEQ ID NO: 5, however, this amino sequence has a modification at one or more of amino acid residues S32, V33, L39, L41, F69, V100, I113, F122, L123, V124, S125, G126, L127, G128, S151, H239, and/or E240 e.g. at 2, 3, 4, 5 or more of these 17 residues. These residues are numbered according to SEQ ID NO: 5; to match the nascent wild-type sequence (SEQ ID NO: 2), the numbering should change +26 (i.e. Ser-32 of SEQ ID NO: 5 is Ser-58 of SEQ ID NO: 2), and to match the mature wild-type sequence (SEQ ID NO: 4) the numbering should change +7 (which also permits easy comparison with ref. 25).

Preferred residues for mutation are 532, V100, L123, V124, S125, G126, L127, G128, H239, and/or E240. Mutations at these residues give proteins having good stability compared to wild-type v2. Within this subset, preferred residues are S32, L123, V124, S125, G126, L127, and/or G128. The most preferred positions are S32, L123, V124, S125, G126, L127, and/or G128, with residues S32 and/or L123 being particularly preferred e.g. S32V and/or L123R. Where one or more of V100, S125, and/or G126 is mutated, it is preferred to mutate also a residue outside this trio.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative. In some embodiments the substitution does not use alanine.

Preferred substitutions at the specified residues are as follows: S32V; V33C; L39C; L41C; F69C; V100T; I113S; F122C; L123R; V124I; S125G or S125T; G126D; L127I; G128A; S151C; H239R; E240H.

Where the mutant fHbp v2 amino acid sequence includes a substitution at E240, this substitution will not be with alanine if only E240 is mutated, although it can be alanine if a further amino acid listed in (b) is substituted e.g. if residues E240 and H239 are both mutated. Ideally, E240 is not mutated on its own, and so a mutant fHbp v2 amino acid sequence with a substitution at E240 should also include a substitution at a second residue e.g. at both E240 and H239 (see mutants #1 and #11).

Where the mutant fHbp v2 amino acid sequence includes a substitution at F122, this substitution will not be with alanine if only F122 is mutated, although it can be alanine if a further amino acid listed in (b) is substituted e.g. if residues F122 and S151 are both mutated. Ideally, F122 is not mutated on its own, and so a mutant fHbp v2 amino acid sequence with a substitution at F122 should also include a substitution at a second residue. When F122 is substituted it is preferred that S151 is also substituted e.g. both are substituted with cysteine, to permit formation of a disulfide bridge (see mutant #10).

Where the mutant fHbp v2 amino acid sequence includes a substitution at L123, this substitution will not be with alanine if only L123 is mutated, although it can be alanine if a further amino acid listed in (b) is substituted e.g. if residues L123 and S32 are both mutated. If L123 is mutated on its own, substitution with arginine is preferred (e.g. see mutant #4). In some embodiments, however, L123 is not mutated on its own, and so a mutant fHbp v2 amino acid sequence with a substitution at L123 can also include a substitution at a second residue. When L123 is substituted it can be preferred that: (i) S32 is also substituted, as seen in mutant #3, and optionally S125 is also substituted, as seen in mutants #20 and #22; or (ii) one or more of residues 124-128 is/arc also substituted e.g. as seen in mutant #12.

Where the mutant fHbp v2 amino acid sequence includes a substitution at V124, it is preferred that this substitution will not be with alanine if only V124 is mutated, although it can be alanine if a further amino acid listed in (b) is substituted e.g. if one or more of residues 123-128 are also mutated. If V124 is mutated on its own, substitution with isoleucine is preferred. Ideally, however, V124 is not mutated on its own, and so a mutant fHbp v2 amino acid sequence with a substitution at V124 should also include a substitution at a second residue. When V124 is substituted it is preferred that one or more of residues 124-128 is/are also substituted e.g. as seen in mutant #12.

Where the mutant fHbp v2 amino acid sequence includes a substitution at L127, it is preferred that this substitution will not be with alanine if only L127 is mutated, although it can be alanine if a further amino acid listed in (b) is substituted e.g. if one or more of residues 123-128 are also mutated. If L127 is mutated on its own, substitution with isoleucine is preferred. Ideally, however, L127 is not mutated on its own, and so a mutant fHbp v2 amino acid sequence with a substitution at L127 should also include a substitution at a second residue. When L127 is substituted it is preferred that one or more of residues 124-128 is/are also substituted e.g. as seen in mutant #12.

Where the mutant fHbp v2 amino acid sequence includes a substitution at S32, it is preferred that this substitution will not be with alanine if only S32 is mutated, although it can be alanine if a further amino acid listed in (b) is substituted e.g. if residues L123 and S32 are both mutated. If S32 is mutated on its own, substitution with valine is preferred. Ideally, however, S32 is not mutated on its own, and so a mutant fHbp v2 amino acid sequence with a substitution at S32 should also include a substitution at a second residue. When S32 is substituted it is preferred that (i) L123 is also substituted e.g. as seen in mutant #3, and optionally S125 is also substituted, as seen in mutants #20 and #22; or (ii) S125 is also substituted e.g. as seen in mutants #19 and #21.

Where the mutant fHbp v2 amino acid sequence includes a substitution at I113, this substitution will not be with alanine if only I113 is mutated, although it can be alanine if a further amino acid listed in (b) is substituted. If I113 is mutated on its own, substitution with serine is preferred e.g. as seen in mutant #7.

Where the mutant fHbp v2 amino acid sequence includes a substitution at V33, this preferably is not with isoleucine. Where the mutant fHbp v2 amino acid sequence includes a substitution at I113, this preferably is not with threonine or with alanine. Where the mutant fHbp v2 amino acid sequence includes a substitution at S151, this preferably is not with phenylalanine. Where the mutant fHbp v2 amino acid sequence includes a substitution at both H239 and E240, this preferably is not to R239 and Q240.

Where more than one substitution is made, these may be selected from groups 2A to 2O as follows:

2A: residues 239 and 240 e.g. mutant #1.
2B: residues 32 and 123 e.g. mutant #3.
2C: residues 125 and 126 e.g. mutant #5.
2D: residues 100, 125 and 126 e.g. mutant #6.
2E: residues 33 and 39 e.g. mutant #8.
2F: residues 41 and 69 e.g. mutant #9.
2G: residues 122 and 151 e.g. mutant #10.
2H: residues 100, 125, 126, 239 and 240 e.g. mutant #11.
2I: residues 32 and 125 e.g. mutants #19 and #21.
2J: residues 32, 123 and 125 e.g. mutants #20 and #22.
2K: residues 33 and 39, both substituted by Cys e.g. mutant #8.
2L: residues 41 and 69, both substituted by Cys e.g. mutant #9.
2M: residues 122 and 151, both substituted by Cys e.g. mutant #10.
2N: residues 123, 124, 125, 126, 127 and 128 e.g. mutant #12.
2O: residues 32, 123, 124, 125, 126, 127 and 128.

Thus, for example, if residue 239 is to be substituted then a preferred second residue for substitution is 240 (i.e. group 2A); moreover, residues 100, 125 and 126 might also be modified (i.e. group 2H, which is a combination of groups 2A and 2D). Within groups 2A to 2N & 2O, preferred substitutions at the specified positions are those listed above. For groups 2K, 2L & 2M, the intention is to introduce a disulfide bridge. Within groups 2A to 2N, preferred mutants are 2A, 2B, 2C, 2D, 2I, 2J, and 2N. More preferred are 2C, 2I, and 2N, with 2N being particularly preferred. Group 2B provides the most preferred mutations, and in particular S32V and L123R (e.g. SEQ ID NOs: 20 and 45). Group 2O is another preferred set of mutations, which combines 2B, 2C and three further mutations (e.g. to give SEQ ID NO: 58).

The amino acid residues noted for mutation in a v2 sequence are numbered relative to SEQ ID NO: 5 which is from strain 2996. The corresponding amino acid residues in a v2 fHbp from any other strain can be readily identified by sequence alignment e.g. being the amino acid which, when aligned to SEQ ID NO: 5 using a pairwise alignment algorithm (e.g. the Needleman-Wunsch global alignment algorithm, as detailed below), aligns with the amino acid mentioned herein. Often the amino acid will be the same as seen in SEQ ID NO: 5 (e.g. residue 32 will be serine), but the alignment will easily identify if this is not the case.

In addition to the mutation(s) noted above, which aim to increase stability, a polypeptide of the invention can include one or more further mutation(s) e.g. to disrupt the polypeptide's interaction with siderophores or, more preferably, to disrupt the polypeptide's ability to bind to fH.

References 19 and 25 report that the interaction between fH and v2 fHbp can be disrupted by mutations at residues R80, D211, E218, E248, T220+H222 (double mutation), and G236. Numbered according to SEQ ID NO: 5, these residues are R73, D203, E210, E240, T213+H215, and G228. Of these positions, polypeptides mutated at D203, E210 or T213+H215 are preferred because reference 25 reports no impairment of important epitopes in these mutants. The specific substitutions studied in reference 25 were R73A, D203A, E210A, T213A+H215A, G228I, and E240A; these substitutions are suitable for use according to the invention.

Reference 24 reports that the interaction between fH and v2 fHbp can be disrupted by mutations at residues R145, S193, F194, L195, A265, E267, K268, V272, I273, L274, E283, T286, H288, F292, T304, and E313 and E283+T304 (double mutation). Numbered according to SEQ ID NO: 5, these residues are R73, S121, F122, L123, A192, E194, K195, V199, I200, L201, E210, T213, H215, F219, T231, and E240 and E210+T231. Four of these overlap with reference 25 (E210, T213, H215, E240). The specific substitutions studied in reference 24 used alanine (except for A265P and T304E), and these substitutions are suitable for use according to the invention.

Reference 24 reports that certain substitutions in v2 can increase affinity for fH, and these should be avoided if the intention is to disrupt binding to fH e.g. E85 in SEQ ID NO: 5 (residue 157 in ref. 24).

Residues which interact with siderophores can be mutated, using the guidance in references 16 and 34 e.g. by aligning SEQ ID NO: 5 herein with SEQ ID NO: 4 of reference 16 to identify residues which can interact with siderophores e.g. with catecholates, hydroxamates or carboxylates.

Further residues which can be mutated include, but are not limited to, S23, L24, D30, Q31, R34, D95, and/or L102 e.g. using the mutations suggested in reference 35.

The polypeptide of the first embodiment can comprise any of SEQ ID NOs: 18 to 36. Similarly, taking into account the 'ΔG' mutation (i.e. truncation of the nascent N-terminus up to and including the native poly-Gly sequence), the polypeptide of the first embodiment can comprise any of SEQ ID NOs: 18 to 36 excluding amino acids 1-26 thereof. For example, the polypeptide of the first embodiment can comprise SEQ ID NO: 45, or can comprise SEQ ID NO: 58.

Considering the possibility of further point mutations (e.g. to disrupt interactions with siderophores and/or fH) the polypeptide of the first embodiment can comprise any of SEQ ID NOs: 18 to 36 (or any of SEQ ID NOs: 18 to 36 excluding amino acids 1-26 thereof, such as SEQ ID NO: 45) but modified by up to 5 single amino acid changes (i.e. 1, 2, 3, 4 or 5 single amino acid substitutions, deletions and/or insertions) provided that the modified sequence can, after administration to a host animal, elicit antibodies which bind to a meningococcal fHbp polypeptide consisting of the amino acid sequence of SEQ ID NO: 46. Such amino acid changes should not reverse the mutations in these sequences relative to the wild-type sequence e.g. SEQ ID NO: 45 should not be mutated at residue V32 or R123.

The invention also provides a polypeptide comprising a fHbp v2 amino acid sequence, wherein the v2 amino acid sequence is identical to a v2 wild-type amino acid sequence except for a mutation at the amino acid position corresponding to Leu-123 of SEQ ID NO: 5, provided that the mutation is not a substitution to alanine (e.g. wherein the mutation is a substitution to arginine). For instance, the polypeptide can comprise SEQ ID NO: 5, but with a mutation (other than L123A) at L123.

SEQ ID NOs: 59 and 60 are two further examples of v2 mutants, namely the mature form of mutants #3 & #4 for strain 8047.

Mutations Relative to SEQ ID NO: 17

Polypeptides of the second embodiment of the invention comprise an amino acid sequence which has at least j % identity to SEQ ID NO: 17, and/or comprise a fragment of SEQ ID NO: 17. In comparison to SEQ ID NO: 17, however, this amino sequence has a modification at one or more of amino acid residues S32, I33, L39, L41, F72, V103, T116, F125, L126, V127, S128, G129, L130, G131, S154, H242, and/or E243 e.g. at 2, 3, 4, 5 or more of these 17 residues. These residues are numbered according to SEQ ID NO: 17; to match the nascent wild-type sequence (SEQ ID NO: 3), the numbering should change +31 (i.e. Ser-32 of SEQ ID NO: 17 is Ser-63 of SEQ ID NO: 3), and to match the mature wild-type sequence (SEQ ID NO: 40) the numbering should change +12.

Preferred residues for mutation are S32, V103, L126, V127, S128, G129, L130, G131, H242, and/or E243. Within this subset, preferred residues are S32, L126, V127, S128, G129, L130, and/or G131. The most preferred positions are S32, L126, V127, S128, G129, L130, and/or G131, with residues S32 and/or L126 being particularly preferred e.g. S32V and/or L126R.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative. In some embodiments the substitution does not use alanine.

Preferred substitutions at the specified residues are as follows: S32V; I33C; L39C; L41C; F72C; V103T; T116S; F125C; L126R; V127I; S128G or S128T; G129D; L130I; G131A; S154C; H242R; E243H.

Where the mutant fHbp v3 amino acid sequence includes a substitution at E243, this substitution will not be with alanine if only E243 is mutated, although it can be alanine if a further amino acid listed in (b) is substituted e.g. if residues E243 and H242 are both mutated. Ideally, E243 is not mutated on its own, and so a mutant fHbp v3 amino acid sequence with a substitution at E243 should also include a substitution at a second residue e.g. at both E243 and H242.

Where the mutant fHbp v3 amino acid sequence includes a substitution at F125, this substitution will not be with alanine if only F125 is mutated, although it can be alanine if a further amino acid listed in (b) is substituted e.g. if residues F125 and S154 are both mutated. Ideally, F125 is not mutated on its own, and so a mutant fHbp v3 amino acid sequence with a substitution at F125 should also include a substitution at a second residue. When F125 is substituted it is preferred that S154 is also substituted e.g. both are substituted with cysteine, to permit formation of a disulfide bridge.

Where the mutant fHbp v3 amino acid sequence includes a substitution at L126, this substitution will not be with alanine if only L126 is mutated, although it can be alanine if a further amino acid listed in (b) is substituted e.g. if residues L126 and S32 are both mutated. If L126 is mutated on its own, substitution with arginine is preferred. In some embodiments, however, L126 is not mutated on its own, and so a mutant fHbp v3 amino acid sequence with a substitution at L126 can also include a substitution at a second residue. When L126 is substituted it can be preferred that: (i) S32 is also substituted, and optionally S128 is also substituted; or (ii) one or more of residues 127-131 is/are also substituted.

Where the mutant fHbp v3 amino acid sequence includes a substitution at V127, it is preferred that this substitution will not be with alanine if only V127 is mutated, although it can be alanine if a further amino acid listed in (b) is substituted e.g. if one or more of residues 126-131 are also mutated. If V127 is mutated on its own, substitution with isoleucine is preferred. Ideally, however, V127 is not mutated on its own, and so a mutant fHbp v3 amino acid sequence with a substitution at V127 should also include a substitution at a second residue. When V127 is substituted it is preferred that one or more of residues 127-131 is/are also substituted.

Where the mutant fHbp v3 amino acid sequence includes a substitution at L130, it is preferred that this substitution will not be with alanine if only L130 is mutated, although it can be alanine if a further amino acid listed in (b) is substituted e.g. if one or more of residues 126-131 are also mutated. If L130 is mutated on its own, substitution with isoleucine is preferred. Ideally, however, L130 is not mutated on its own, and so a mutant fHbp v3 amino acid sequence with a substitution at L130 should also include a substitution at a second residue. When L130 is substituted it is preferred that one or more of residues 127-131 is/are also substituted.

Where the mutant fHbp v3 amino acid sequence includes a substitution at S32, it is preferred that this substitution will not be with alanine if only S32 is mutated, although it can be alanine if a further amino acid listed in (b) is substituted e.g. if one or more of residues if residues L126 and S32 are both mutated. If S32 is mutated on its own, substitution with valine is preferred. Ideally, however, S32 is not mutated on its own, and so a mutant fHbp v3 amino acid sequence with a substitution at S32 should also include a substitution at a second residue. When S32 is substituted it is preferred that (i) L 126 is also substituted, and optionally S128 us also substituted, or (ii) S128 is also substituted.

Where the mutant fHbp v3 amino acid sequence includes a substitution at T113, this substitution will not be with alanine if only T113 is mutated, although it can be alanine if a further amino acid listed in (b) is substituted. If T113 is mutated on its own, substitution with serine is preferred.

Where the mutant fHbp v3 amino acid sequence includes a substitution at 133, this preferably is not with valine. Where the mutant fHbp v3 amino acid sequence includes a substitution at T116, this preferably is not with isoleucine. Where the mutant fHbp v3 amino acid sequence includes a substitution at G129, this preferably is not with serine. Where the mutant fHbp v3 amino acid sequence includes a substitution at both H242 and E243, this preferably is not to R242 and Q243.

Where more than one substitution is made, these may be selected from groups 3A to 3O as follows:
3A: residues 242 and 243.
3B: residues 32 and 126.
3C: residues 128 and 129.
3D: residues 103, 128 and 129.
3E: residues 33 and 39.
3F: residues 41 and 72.
3G: residues 125 and 154.
3H: residues 103, 128, 129, 242 and 243.
3I: residues 32 and 128.
3J: residues 32, 126 and 128.
3K: residues 33 and 39, both substituted by Cys.
3L: residues 41 and 72, both substituted by Cys.
3M: residues 125 and 154, both substituted by Cys.
3N: residues 126, 127, 128, 129, 130 and 131.
3O: residues 32, 126, 127, 128, 129, 130 and 131.

Thus, for example, if residue 242 is to be substituted then a preferred second residue for substitution is 243 (i.e. group 3A); moreover, residues 103, 128 and 129 might also be modified (i.e. group 3H, which is a combination of groups 3A and 3D). Within groups 3A to 3N & 3O, preferred substitutions at the specified positions are those listed above. For groups 3K, 3L & 3M, the intention is to introduce a disulfide bridge. Within groups 3A to 3N, preferred mutants are 3A, 3B, 3C, 3D, 3I, 3J, and 3N. More preferred are 3C, 3I, and 3N, with 3N being particularly preferred. Group 3B provides the most preferred mutations, and in particular S32V and L126R (e.g. comprising SEQ ID NO: 44). Group 3O is another preferred mutation, which combines 3B, 3C and three further mutations (e.g. to give SEQ ID NO: 61). Mutation L126R alone provides SEQ ID NO: 53.

The amino acid residues noted for mutation in a v3 sequence are numbered relative to SEQ ID NO: 17 which is from strain M1239. The corresponding amino acid residues in a v3 fHbp from any other strain can be readily identified by sequence alignment e.g. being the amino acid which, when aligned to SEQ ID NO: 17 using a pairwise alignment algorithm (e.g. the Needleman-Wunsch global alignment algorithm, as detailed below), aligns with the amino acid mentioned herein. Often the amino acid will be the same as seen in SEQ ID NO: 17 (e.g. residue 32 will be serine), but the alignment will easily identify if this is not the case.

In addition to the mutation(s) noted above, which aim to increase stability, a polypeptide of the invention can include one or more further mutation(s) e.g. to disrupt the polypeptide's interaction with siderophores or, more preferably, to disrupt the polypeptide's ability to bind to fH.

Reference 24 reports that the interaction between fH and v3 fHbp can be disrupted by mutations at residues Q107, I147, L156, A157, L195, V196, V272, E283, T286, T304, V311, E313 and E283+T304 (double mutation). Numbered according to SEQ ID NO: 17, these residues are: Q35, I78, L87, A88, L126, V127, V202, E213, T216, T234, V241, E243 and E213+T234. The specific substitutions studied in reference 24 used alanine (except for A157E and T231E), and these substitutions are suitable for use according to the invention. Residues T216 and E243 are also reported in reference 23. Reference 36 reports that the interaction between fH and v3 fHbp can be disrupted by mutations at residues H288 and G318 (H218 and G248 numbered according to SEQ ID NO: 17), and these substitutions are suitable for use according to the invention e.g. H218R, G248D.

Ref 24 reports that certain substitutions in v3 can increase affinity for fH, and these should be avoided if the intention is to disrupt binding to fH e.g. P44 in SEQ ID NO: 17 (residue 106 in ref. 24)

Residues which interact with siderophores can be mutated, using the guidance in references 16 and 34 e.g. by aligning SEQ ID NO: 17 herein with SEQ ID NO: 4 of reference 16 to identify residues which can interact with siderophores e.g. with catecholates, hydroxamates or carboxylates.

The polypeptide of the second embodiment can comprise any of SEQ ID NOs: 41 to 44. Considering the possibility of further point mutations (e.g. to disrupt interactions with siderophores and/or fH) the polypeptide of the first embodiment can comprise any of SEQ ID NOs: 41 to 44 but modified by up to 5 single amino acid changes (i.e. 1, 2, 3, 4 or 5 single amino acid substitutions, deletions and/or insertions) provided that the modified sequence can, after administration to a host animal, elicit antibodies which bind to a meningococcal fHbp polypeptide consisting of the amino acid sequence of SEQ ID NO: 40. Such amino acid changes should not reverse the mutations in these sequences relative to the wild-type sequence e.g. SEQ ID NO: 44 should not be mutated at residue V32 or R126.

The invention also provides a polypeptide comprising a fHbp v3 amino acid sequence, wherein the v3 amino acid sequence is identical to a v3 wild-type amino acid sequence except for a mutation at the amino acid position corresponding to Leu-126 of SEQ ID NO: 17, provided that the mutation is not a substitution to alanine (e.g. wherein the mutation is a substitution to arginine). For instance, the polypeptide can comprise SEQ ID NO: 17, but with a mutation (other than L126A) at L126.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture), etc. Heterologous expression in an *E. coli* host is a preferred expression route.

Polypeptides of the invention are ideally at least 100 amino acids long e.g. 150aa, 175aa, 200aa, 225aa, or longer. They include a mutant fHbp v2 and/or v3 amino acid sequence, and the mutant fHbp v2 or v3 amino acid sequence should similarly be at least 100 amino acids long e.g. 150aa, 175aa, 200aa, 225aa, or longer.

The fHbp is naturally a lipoprotein in *N. meningitidis*. It has also been found to be lipidated when expressed in *E. coli* with its native leader sequence or with heterologous leader sequences. Polypeptides of the invention may have a N-terminus cysteine residue, which may be lipidated e.g. comprising a palmitoyl group, usually forming tripalmitoyl-S-glyceryl-cysteine. In other embodiments the polypeptides are not lipidated.

Polypeptides are preferably prepared in substantially pure or substantially isolated form (i.e. substantially free from other Neisserial or host cell polypeptides). In general, the polypeptides are provided in a non-naturally occurring environment e.g. they are separated from their naturally-occurring environment. In certain embodiments, the polypeptide is present in a composition that is enriched for the polypeptide as compared to a starting material. Thus purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, glycosylated, non-glycosylated, lipidated, disulfide bridges, etc.).

SEQ ID NOs 4, 5, 17 and 40 do not include a N-terminus methionine. If a polypeptide of the invention is produced by translation in a biological host then a start codon is required, which will provide a N-terminus methionine in most hosts. Thus a polypeptide of the invention will, at least at a nascent stage, include a methionine residue upstream of said SEQ ID NO sequence.

Cleavage of nascent sequences means that the mutant fHbp v2 or v3 amino acid sequence might itself provide the polypeptide's N-terminus. In other embodiments, however, a polypeptide of the invention can include a N-terminal sequence upstream of the mutant fHbp v2 or v3 amino acid sequence. In some embodiments the polypeptide has a single methionine at the N-terminus immediately followed by the mutant fHbp v2 or v3 amino acid sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. His_n where n=4, 5, 6, 7, 8, 9, 10 or more). Other suitable N-terminal amino acid sequences will be apparent to those skilled in the art e.g. the native upstream sequences present in SEQ ID NO: 2 or SEQ ID NO: 3.

A polypeptide of the invention may also include amino acids downstream of the final amino acid of the mutant fHbp v2 or v3 amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. His_n where n=4, 5, 6, 7, 8, 9, 10 or more), or sequences which enhance polypeptide stability. Other suitable C-terminal amino acid sequences will be apparent to those skilled in the art.

In some embodiments, the invention excludes polypeptides which include a histidine tag (cf. refs. 24 & 25), and in particular a hexahistidine tag at the C-terminus.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention may be attached or immobilised to a solid support.

Polypeptides of the invention may comprise a detectable label e.g. a radioactive label, a fluorescent label, or a biotin label. This is particularly useful in immunoassay techniques.

```
As disclosed in reference 164, fHbp can be split
into three domains, referred to as A, B and C.
Taking SEQ ID NO: 1, the three domains are (A)
1-119, (B) 120-183 and (C) 184-274:
MNRTAFCCLSLTTALILTACSSGGGGVAADIGAGLADALTAPLDHKDKG

LQSLTLDQSVRKNEKLKLAAQGAEKTYGNGDSLNTGKLKNDKVSRFDFI

RQIEVDGQLITLESGEFQVYKQSHSALTAFQTEQIQDSEHSGKMVAKRQ

FRIGDIAGEHTSFDKLPEGGRATYRGTAFGSDDAGGKLTYTIDFAAKQG

NGKIEHLKSPELNVDLAAADIKPDGKRHAVISGSVLYNQAEKGSYSLGI

FGGKAQEVAGSAEVKTVNGIRHIGLAAKQ
```

The mature form of domain 'A', from Cys-20 at its N-terminus to Lys-119, is called 'A_{mature}'.

Multiple fHbp sequences are known and these can readily be aligned using standard methods. By such alignments the skilled person can identify (a) domains 'A' (and 'A_{mature}'), 'B' and 'C' in any given fHbp sequence by comparison to the coordinates in the MC58 sequence, and (b) single residues in multiple fHbp sequences e.g. for identifying substitutions. For ease of reference, however, the domains are defined below:

Domain 'A' in a given fHbp sequence is the fragment of that sequence which, when aligned to SEQ ID NO: 1 using a pairwise alignment algorithm, starts with the amino acid aligned to Met-1 of SEQ ID NO: 1 and ends with the amino acid aligned to Lys-119 of SEQ ID NO: 1.

Domain 'A_{mature}' in a given fHbp sequence is the fragment of that sequence which, when aligned to SEQ ID NO: 1 using a pairwise alignment algorithm, starts with the amino acid aligned to Cys-20 of SEQ ID NO: 1 and ends with the amino acid aligned to Lys-119 of SEQ ID NO: 1.

Domain 'B' in a given fHbp sequence is the fragment of that sequence which, when aligned to SEQ ID NO: 1 using a pairwise alignment algorithm, starts with the amino acid aligned to Gln-120 of SEQ ID NO: 1 and ends with the amino acid aligned to Gly-183 of SEQ ID NO: 1.

Domain 'C' in a given fHbp sequence is the fragment of that sequence which, when aligned to SEQ ID NO: 1 using a pairwise alignment algorithm, starts with the amino acid aligned to Lys-184 of SEQ ID NO: 1 and ends with the amino acid aligned to Gln-274 of SEQ ID NO: 1.

The preferred pairwise alignment algorithm for defining the domains is the Needleman-Wunsch global alignment algorithm [158], using default parameters (e.g. with Gap opening penalty=10.0, and with Gap extension penalty=0.5, using the EBLOSUM62 scoring matrix). This algorithm is conveniently implemented in the needle tool in the EMBOSS package [159].

In some embodiments, a mutant fHbp v2 or v3 amino acid sequence of the invention is truncated to remove its domain A. In general, however, it is preferred that the mutant fHbp v2 or v3 amino acid sequence should include both a N-terminal β-barrel and a C-terminal β-barrel.

In some embodiments, a polypeptide comprises an amino acid sequence as described above, except that up to 10 amino acids (i.e. 1, 2, 3, 4, 5, 6, 7, 8, 9 or 10) at the N-terminus and/or up to 10 amino acids (i.e. 1, 2, 3, 4, 5, 6, 7, 8, 9 or 10) at the C-terminus are deleted.

Polypeptides of the invention typically consist of an artificial amino acid sequence, namely a sequence which is not present in any naturally-occurring meningococci.

Affinity for factor H can be quantitatively assessed using surface plasmon resonance e.g. as disclosed in references 18 and 21-24 with immobilised human fH. Mutations which provide an affinity reduction (i.e. an increase in the dissociation constant, $K_D$) of at least 10-fold, and ideally at least 100-fold, is preferred (when measured under the same experimental conditions relative to the same polypeptide but without the mutation).

Nucleic Acids

The invention provides nucleic acid encoding a polypeptide of the invention as defined above.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label.

The invention also provides vectors (such as plasmids) comprising nucleotide sequences of the invention (e.g. cloning or expression vectors, such as those suitable for nucleic acid immunisation) and host cells transformed with such vectors.

Bactericidal Responses

Preferred polypeptides of the invention can elicit antibody responses that are bactericidal against meningococci. Bactericidal antibody responses are conveniently measured in mice and are a standard indicator of vaccine efficacy (e.g. see end-note 14 of ref. 37; also ref. 38).

Polypeptides of the first embodiment invention can preferably elicit an antibody response which is bactericidal against a *N. meningitidis* strain which expresses a v2 fHbp sequence e.g. one or more of strains 961-5945, 2996, 96217, 312294, 11327, a22, gb013 (=M01-240013), e32, m1090, m4287, 860800, 599, 95N477, 90-18311, e11, m986, m2671, 1000, m1096, m3279, bz232, dk353, m3697, ngh38, and/or L93/4286. Bactericidal responses can for instance be assessed against var2 strain M2091 (ATCC 13091).

Preferred polypeptides of the first embodiment invention can elicit antibodies in a mouse which are bactericidal against strain M2091 in a serum bactericidal assay.

Polypeptides of the second embodiment invention can preferably elicit an antibody response which is bactericidal against a *N. meningitidis* strain which expresses a v3 fHbp sequence e.g. one or more of strains M1239, 16889, gb355 (=M01-240355), m3369, m3813, ngp165. Bactericidal responses can for instance be assessed against var3 strain M01-240355, which is a *Neisseria* MLST reference strains (id 19265 in ref. 39) which has been fully sequenced (see EMBL ID CP002422 [40])

Preferred polypeptides of the second embodiment invention can elicit antibodies in a mouse which are bactericidal against strain M01-240355 in a serum bactericidal assay.

For example, an immunogenic composition comprising these polypeptides can provide a serum bactericidal titer of ≥1:4 using the Goldschneider assay with human complement [41-43], and/or providing a serum bactericidal titer of ≥1:128 using baby rabbit complement.

Immunisation

Polypeptides of the invention may be used as the active ingredient of immunogenic compositions, and so the invention provides an immunogenic composition (e.g. a vaccine) comprising a polypeptide of the invention.

The invention also provides a method for raising an antibody response in a mammal, comprising administering an immunogenic composition of the invention to the mammal. The antibody response is preferably a protective and/or bactericidal antibody response. The invention also provides polypeptides of the invention for use in such methods.

The invention also provides a method for protecting a mammal against a Neisserial (e.g. meningococcal) infection, comprising administering to the mammal an immunogenic composition of the invention.

The invention provides polypeptides of the invention for use as medicaments (e.g. as immunogenic compositions or as vaccines) or as diagnostic reagents. It also provides the use of nucleic acid or polypeptide of the invention in the manufacture of a medicament for preventing Neisserial (e.g. meningococcal) infection in a mammal.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N. meningitidis* (for example in serogroup B).

Efficacy of therapeutic treatment can be tested by monitoring Neisserial infection after administration of the composition of the invention. Efficacy of prophylactic treatment can be tested by monitoring immune responses against fHbp after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 44.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [45]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. The term "prevention" means that the progression of the disease is reduced and/or eliminated, or that the onset of the disease is eliminated. For example, the immune system of a subject may be primed (e.g by vaccination) to trigger an immune response and repel infection such that the onset of the disease is eliminated. A vaccinated subject may thus get infected, but is better able to repel the infection than a control subject. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of ref. 46.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of ref. 46). The salts can take any suitable form (e.g. gel, crystalline, amorphous, etc.).

Further Antigenic Components

Compositions of the invention include mutant v2 and/or v3 fHbp sequence. It is useful if the composition should not include complex or undefined mixtures of antigens e.g. it is preferred not to include outer membrane vesicles in the composition. Polypeptides of the invention are preferably expressed recombinantly in a heterologous host and then purified.

As well as including a fHbp polypeptide, a composition of the invention may also include one or more further neisserial immunogen(s), as a vaccine which targets more than one immunogen per bacterium decreases the possibility of selecting escape mutants. Thus a composition can include a second polypeptide that, when administered to a mammal, elicits an antibody response that is bactericidal against meningococcus. The second polypeptide can be a meningococcal fHbp, but will often not be a fHbp e.g. it may be a NHBA sequence, a NadA sequence, etc.

Any such further neisserial immunogen may be present as a separate polypeptide to the mutant v2 or v3 fHbp of the invention or may be present as a fusion polypeptide with the modified fHbp. For instance, fusion of meningococcal 936 polypeptide and fHbp polypeptides is known [55,56]. Fusion proteins comprising SEQ ID NO: 44 and/or SEQ ID NO: 45 are particularly preferred, optionally wherein SEQ ID NO: 44 and/or 45 is/are modified by up to 5 single amino acid changes (i.e. 1, 2, 3, 4 or 5 single amino acid substitutions, deletions and/or insertions) as described elsewhere herein.

A composition of the invention may include a NHBA antigen. The Neisserial Heparin Binding Antigen (NHBA) antigen was included in the published genome sequence for meningococcal serogroup B strain MC58 [47] as gene NMB2132 (GenBank accession number GI: 7227388; SEQ ID NO: 6 herein). The sequences of NHBA antigen from many strains have been published since then. For example, allelic forms of NHBA can be seen in FIGS. 5 and 15 of reference 48, and in example 13 and FIG. 21 of reference 1 (SEQ IDs 3179 to 3184 therein). Various immunogenic fragments of the NHBA antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most useful NHBA antigens of the invention can elicit antibodies which, after administration to a subject, can bind to a meningococcal polypeptide consisting of amino acid sequence SEQ ID NO: 6. Advantageous NHBA antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [47] as gene NMB1994 (GenBank accession number GI:7227256; SEQ ID NO: 7 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a)

having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 7. The most useful NadA antigens of the invention can elicit antibodies which, after administration to a subject, can bind to a meningococcal polypeptide consisting of amino acid sequence SEQ ID NO: 7. Advantageous NadA antigens for use with the invention can elicit bactericidal anti-meningococcal antibodies after administration to a subject. SEQ ID NO: 15 is one such fragment.

A composition of the invention may include a NspA antigen. The NspA antigen was included in the published genome sequence for meningococcal serogroup B strain MC58 [47] as gene NMB0663 (GenBank accession number GI:7225888; SEQ ID NO: 8 herein). The antigen was previously known from references 49 & 50. The sequences of NspA antigen from many strains have been published since then. Various immunogenic fragments of NspA have also been reported. Preferred NspA antigens for use with the invention comprise n amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 8. The most useful NspA antigens of the invention can elicit antibodies which, after administration to a subject, can bind to a meningococcal polypeptide consisting of amino acid sequence SEQ ID NO: 8. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [47] as gene NMB1668 (SEQ ID NO: 9 herein). The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 9, where the value of i is 50, 60, 70, 80, 90, 95, 99 or more. In other embodiments a HmbR sequence used according to the invention may comprise a fragment of at least j consecutive amino acids from SEQ ID NO: 9, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 9 and/or (ii) comprising a fragment of at least j consecutive amino acids from SEQ ID NO: 9. Preferred fragments of j amino acids comprise an epitope from SEQ ID NO: 9. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 51. The most useful HmbR antigens of the invention can elicit antibodies which, after administration to a subject, can bind to a meningococcal polypeptide consisting of amino acid sequence SEQ ID NO: 9. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [47] as gene NMB0992 (GenBank accession number GI:7226232; SEQ ID NO: 10 herein). The sequences of NhhA antigen from many strains have been published since e.g. refs 48 & 52, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10. The most useful NhhA antigens of the invention can elicit antibodies which, after administration to a subject, can bind to a meningococcal polypeptide consisting of amino acid sequence SEQ ID NO: 10. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [47] as gene NMB1985 (GenBank accession number GI:7227246; SEQ ID NO: 11 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11. The most useful App antigens of the invention can elicit antibodies which, after administration to a subject, can bind to a meningococcal polypeptide consisting of amino acid sequence SEQ ID NO: 11. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [47] as gene NMB0182 (GenBank accession number GI:7225401; SEQ ID NO: 12 herein). The sequences of Omp85 antigen from many strains have been published since then. Further information on Omp85 can be found in references 53 and 54. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12. The most useful Omp85 antigens of the invention can elicit antibodies which, after administration to a subject, can bind to a meningococcal polypeptide consisting of amino acid sequence SEQ ID NO: 12. Advantageous Omp85 antigens for use with the invention can elicit bactericidal anti-meningococcal antibodies after administration to a subject.

A composition of the invention may include a 936 antigen. The 936 antigen was included in the published genome sequence for meningococcal serogroup B strain MC58 [47] as gene NMB2091 (SEQ ID NO: 13 herein). Preferred 936 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13. The most useful 936 antigens of the invention can elicit antibodies which, after administration to a subject, can bind to a meningococcal polypeptide consisting of amino acid sequence SEQ ID NO: 13. The 936 antigen is a good fusion partner for fHbp (e.g. see references 55 & 56).

A composition may comprise: a polypeptide comprising SEQ ID NO: 14; a polypeptide comprising SEQ ID NO: 15; and a polypeptide of the invention comprising a mutant fHbp v2 amino acid sequence and SEQ ID NO: 13 (cf. refs. 55 & 56).

A composition may comprise: a polypeptide comprising SEQ ID NO: 14; a polypeptide comprising SEQ ID NO: 15; and a polypeptide of the invention comprising a mutant fHbp v3 amino acid sequence and SEQ ID NO: 13 (cf. refs. 55 & 56).

In some embodiments, a polypeptide of the invention is combined with a further meningococcal fHbp sequence. In particular, a v2 polypeptide can be combined with a v1 and/or a v3 polypeptide to increase the spectrum of strain coverage [162]. Thus a composition can comprise: (i) a polypeptide of the invention comprising a mutant fHbp v2 amino acid sequence; and (ii) a v1 fHbp polypeptide and/or a v3 fHbp polypeptide. In other embodiments, a polypeptide of the invention can comprise (i) a mutant fHbp v2 amino acid sequence and (ii) a v1 fHbp amino acid sequence and/or a v3 fHbp amino acid sequence. Thus the v1 and/or v3 sequences can be combined with the mutant v2 sequence as separate entities in a composition, or within a fusion polypeptide.

Similarly, a v3 polypeptide can be combined with a v1 and/or a v2 polypeptide to increase the spectrum of strain coverage [162]. Thus a composition can comprise: (i) a polypeptide of the invention comprising a mutant fHbp v3 amino acid sequence; and (ii) a v1 fHbp polypeptide and/or a v2 fHbp polypeptide. In other embodiments, a polypeptide of the invention can comprise (i) a mutant fHbp v3 amino acid sequence and (ii) a v1 fHbp amino acid sequence and/or a v2 fHbp amino acid sequence. Thus the v1 and/or v2 sequences can be combined with the mutant v3 sequence as separate entities in a composition, or within a fusion polypeptide.

Moreover, mutant v2 and v3 polypeptides can be combined with each other to increase strain coverage. Thus a composition can comprise: (i) a polypeptide of the invention comprising a mutant fHbp v2 amino acid sequence; (ii) a polypeptide of the invention comprising a mutant fHbp v3 amino acid sequence; and (iii) a fHbp v1 polypeptide. In other embodiments, a polypeptide of the invention can comprise (i) a mutant fHbp v2 amino acid sequence (ii) a mutant v3 fHbp amino acid sequence and (iii) a fHbp v1 amino acid sequence. Thus the mutant v2 and v3 sequences can be combined with a v1 sequence as separate entities in a composition, or within a fusion polypeptide. The v1 sequence can be a wild-type sequence or a mutant sequence.

A v1 fHbp can comprise (a) an amino acid sequence which has at least k % identity to SEQ ID NO: 16, and/or (b) a fragment of SEQ ID NO: 16. Information about 'k' and fragments are given above. The fragment will typically include at least one epitope from SEQ ID NO: 16, and the v1 fHbp polypeptide will include at least one epitope which is not present in the v2 or v3 amino acid sequence of the invention, such that antibodies elicited by the v1 fHbp can recognise v1 strains. Ideally, the v1 fHbp can elicit antibodies which are bactericidal against v1 strains e.g. against strain MC58 (available from the ATCC as 'BAA-335'). The v1 fHbp can include an amino acid mutation which disrupts its ability to bind to fH.

A v2 fHbp can comprise (a) an amino acid sequence which has at least k % identity to SEQ ID NO: 5, and/or (b) a fragment of SEQ ID NO: 5. Information about 'k' and fragments are given above. The fragment will typically include at least one epitope from SEQ ID NO: 5, and the v2 fHbp polypeptide will include at least one epitope which is not present in the v3 amino acid sequence of the invention, such that antibodies elicited by the v2 fHbp can recognise v2 strains. Ideally, the v2 fHbp can elicit antibodies which are bactericidal against v2 strains e.g. against strain M2091 (ATCC 13091). The v2 fHbp can be a polypeptide of the first embodiment.

A v3 fHbp can comprise (a) an amino acid sequence which has at least k % identity to SEQ ID NO: 17, and/or (b) a fragment of SEQ ID NO: 17. Information about 'k' and fragments are given above. The fragment will typically include at least one epitope from SEQ ID NO: 17, and the v3 fHbp polypeptide will include at least one epitope which is not present in the v2 amino acid sequence of the invention, such that antibodies elicited by the v3 fHbp can recognise v3 strains. Ideally, the v3 fHbp can elicit antibodies which are bactericidal against v3 strains e.g. against strain M01-240355. The v3 fHbp can be a polypeptide of the second embodiment.

Thus, for instance, the invention provides a polypeptide comprising, within a single polypeptide chain, each of: (i) a fHbp v1 amino acid sequence; (ii) a mutant fHbp v2 amino acid sequence; and (iii) a mutant fHbp v3 amino acid sequence. The polypeptide can, after administration to a host animal, elicit antibodies which bind to each of: a meningococcal fHbp polypeptide consisting of the amino acid sequence of SEQ ID NO: 46; a meningococcal fHbp polypeptide consisting of the amino acid sequence of SEQ ID NO: 4; and a meningococcal fHbp polypeptide consisting of the amino acid sequence of SEQ ID NO: 40. The sequence of (i) can comprise an amino acid sequence which has at least k % identity to SEQ ID NO: 16. The sequence of (ii) can comprise an amino acid sequence which has at least k % identity to SEQ ID NO: 5, but differing from SEQ ID NO: 5 at one or more of the following residues: S32, V33, L39, L41, F69, V100, I113, F122, L123, V124, S125, G126, L127, G128, S151, H239, and/or E240. The sequence of (iii) can comprise an amino acid sequence which has at least k % identity to SEQ ID NO: 17, but differing from SEQ ID NO: 17 at one or more of the following residues: S32, I33, L39, L41, F72, V103, T116, F125, L126, V127, S128, G129, L130, G131, S154, H242, and/or E243. In a preferred embodiment: the sequence of (i) comprises SEQ ID NO: 16, optionally modified by up to 5 single amino acid changes (i.e. 1, 2, 3, 4 or 5 single amino acid substitutions, deletions and/or insertions); the sequence of (ii) comprises SEQ ID NO: 45, optionally modified by up to 5 single amino acid changes (i.e. 1, 2, 3, 4 or 5 single amino acid substitutions, deletions and/or insertions), provided such amino acid changes do not reverse the mutations in these sequences relative to the wild-type sequence; and the sequence of (iii) comprises SEQ ID NO: 44, optionally modified by up to 5 single amino acid changes (i.e. 1, 2, 3, 4 or 5 single amino acid substitutions, deletions and/or insertions e.g. to give SEQ ID NO: 53), provided such amino acid changes do not reverse the mutations in these sequences relative to the wild-type sequence. Amino acid sequences (i), (ii) and (iii) can be arranged in any order from N- to C-terminus in the polypeptide, but are preferably in the order (ii), then (iii), then (i). For instance, the invention provides a polypeptide of formula -A-B-C- wherein: A comprises SEQ ID NO: 45, optionally modified by up to 3 single amino acid substitutions; B comprises SEQ ID NO: 44, optionally modified by up to 3 single amino acid substitutions; and C comprises SEQ ID NO: 16, optionally modified by up to 3 single amino acid substitutions (e.g. substitution(s) to to disrupt binding to fH). A preferred C comprises SEQ ID NO: 49, where residue Arg-34 is mutated to Ser as reported for the 'R41 S' mutation in ref. 21.

A particularly preferred polypeptide comprises amino acid sequence SEQ ID NO: 47. This sequence includes, from N-terminus to C-terminus: the mutant v2 (SEQ ID NO: 45); the mutant v3 (SEQ ID NO: 44); and the mutant v1 (SEQ ID NO: 49). Between these three mutant fHbp sequences there is in each case a linker sequence, SEQ ID NO: 50. In one embodiment, the polypeptide comprises amino acid sequence SEQ ID NO: 48, which has a N-terminus methionine, then SEQ ID NO: 37, and then SEQ ID NO: 47.

SEQ ID NO: 47 (alone, or within SEQ ID NO: 48) can optionally be modified by up to 5 single amino acid changes (i.e. 1, 2, 3, 4 or 5 single amino acid substitutions, deletions and/or insertions), provided such amino acid changes do not reverse the mutations in the v1, v2, and v3 sequences relative to the wild-type sequence i.e. amino acid residues V32, R123, V285, R379, and S543 of SEQ ID NO: 47 should not be mutated to S32, L123, S285, L379, and R543. In one exceptional embodiment, however, V285 can revert to S285 and/or V32 can revert to S32.

The mutant fusion can ideally elicit antibodies which bind to each of: a wild-type v1 meningococcal fHbp polypeptide consisting of amino acid sequence SEQ ID NO: 46; a wild-type v2 meningococcal fHbp polypeptide consisting of amino acid sequence SEQ ID NO: 4; and a wild-type v3 meningococcal fHbp polypeptide consisting of amino acid sequence SEQ ID NO: 40.

In addition to Neisserial polypeptide antigens, the composition may include antigens for immunising against other diseases or infections. For example, the composition may include one or more of the following further antigens:

a saccharide antigen from *N. meningitidis* serogroup A, C, W135 and/or Y, such as the saccharide disclosed in ref. 57 from serogroup C (see also ref. 58) or in ref. 59.

a saccharide antigen from *Streptococcus pneumoniae* [e.g. 60, 61, 62].

an antigen from hepatitis A virus, such as inactivated virus [e.g. 63, 64].

an antigen from hepatitis B virus, such as the surface and/or core antigens [e.g. 64, 65], a diphtheria antigen, such as a diphtheria toxoid [e.g. chapter 3 of ref. 66] e.g. the $CRM_{197}$ mutant [e.g. 67].

a tetanus antigen, such as a tetanus toxoid (e.g. chapter 4 of ref. 66).

an antigen from *Bordetella pertussis*, such as pertussis holotoxin (PT) and filamentous haemagglutinin (FHA) from *B. pertussis*, optionally also in combination with pertactin and/or agglutinogens 2 and 3 (e.g. refs. 68 & 69).

a saccharide antigen from *Haemophilus influenzae* B [e.g. 58].

polio antigen(s) [e.g. 70, 71] such as IPV.

measles, mumps and/or rubella antigens (e.g. chapters 9, 10 & 11 of ref. 66).

influenza antigen(s) (e.g. chapter 19 of ref. 66), such as the haemagglutinin and/or neuraminidase surface proteins.

an antigen from *Moraxella catarrhalis* [e.g. 72].

an protein antigen from *Streptococcus agalactiae* (group B *streptococcus*) [e.g. 73, 74].

a saccharide antigen from *Streptococcus agalactiae* (group B *streptococcus*).

an antigen from *Streptococcus pyogenes* (group A *streptococcus*) [e.g. 74, 75, 76].

an antigen from *Staphylococcus aureus* [e.g. 77].

The composition may comprise one or more of these further antigens.

Toxic protein antigens may be detoxified where necessary (e.g. detoxification of pertussis toxin by chemical and/or genetic means [69]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 µg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (which could be RNA, such as a self-replicating RNA, or DNA, such as a plasmid) encoding the antigen may be used.

In some embodiments a composition of the invention comprises in addition to the fHbp sequence, conjugated capsular saccharide antigens from 1, 2, 3 or 4 of meningococcus serogroups A, C, W135 and Y. In other embodiments a composition of the invention comprises in addition to the fHbp sequence, at least one conjugated pneumococcal capsular saccharide antigen.

Meningococcus Serogroups Y, W135, C and A

Current serogroup C vaccines (Menjugate™ [57,78], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier. The Menactra™ vaccine contains conjugated capsular saccharide antigens from each of serogroups Y, W135, C and A.

Compositions of the present invention may include capsular saccharide antigens from one or more of meningococcus serogroups Y, W135, C and A, wherein the antigens are conjugated to carrier protein(s) and/or are oligosaccharides. For example, the composition may include a capsular saccharide antigen from: serogroup C; serogroups A and C; serogroups A, C and W135; serogroups A, C and Y; serogroups C, W135 and Y; or from all four of serogroups A, C, W135 and Y.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [79].

If hydrolysis is performed, the hydrolysate will generally be sized in order to remove short-length oligosaccharides [58]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 78, as used in Menjugate™.

The saccharide antigen may be chemically modified. This is particularly useful for reducing hydrolysis for serogroup A [80]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [80]. This modification improves resistance to hydrolysis.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique.

Typical carrier proteins are bacterial toxins, such as diphtheria or tetanus toxins, or toxoids or mutants thereof. The $CRM_{197}$ diphtheria toxin mutant [81] is useful, and is the carrier in the PREVNAR™ product. Other suitable carrier proteins include the *N. meningitidis* outer membrane protein complex [82], synthetic peptides [83,84], heat shock proteins [85,86], pertussis proteins [87,88], cytokines [89], lymphokines [89], hormones [89], growth factors [89], artificial proteins comprising multiple human $CD4^+$ T cell epitopes from various pathogen-derived antigens [90] such as N19 [91], protein D from *H. influenzae* [92-94], pneumolysin [95] or its non-toxic derivatives [96], pneumococcal surface protein PspA [97], iron-uptake proteins [98], toxin A or B from *C. difficile* [99], recombinant *P. aeruginosa* exoprotein A (rEPA) [100], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [101,102, etc.]). Other suitable techniques use carbodiimides, hydrazides, active esters, norborane, p-nitrobenzoic acid, N-hydroxysuccinimide, S-NHS, EDC, TSTU, etc.

Linkages via a linker group may be made using any known procedure, for example, the procedures described in references 103 and 104. One type of linkage involves reductive amination of the polysaccharide, coupling the resulting amino group with one end of an adipic acid linker group, and then coupling a protein to the other end of the adipic acid linker group [105,106]. Other linkers include B-propionamido [107], nitrophenyl-ethylamine [108], haloacyl halides [109], glycosidic linkages [110], 6-aminocaproic acid [111], ADH [112], $C_4$ to $C_{12}$ moieties [113] etc. As an alternative to using a linker, direct linkage can be used. Direct linkages to the protein may comprise oxidation of the polysaccharide followed by reductive amination with the protein, as described in, for example, references 114 and 115.

A process involving the introduction of amino groups into the saccharide (e.g. by replacing terminal $=O$ groups with $-NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

Outer Membrane Vesicles

Some compositions of the invention do not include complex or undefined mixtures of antigens, which are typical characteristics of OMVs. However, the invention can be used in conjunction with OMVs, as fHbp has been found to enhance their efficacy [4], in particular by over-expressing the polypeptides of the invention in the strains used for OMV preparation. See also below.

This approach may be used in general to improve preparations of *N. meningitidis* serogroup B microvesicles [116], 'native OMVs' [117], blebs or outer membrane vesicles [e.g. refs. 118 to 123, etc.]. These may be prepared from bacteria which have been genetically manipulated [124-127] e.g. to increase immunogenicity (e.g. hyper-express immunogens), to reduce toxicity, to inhibit capsular polysaccharide synthesis, to down-regulate PorA expression, etc. They may be prepared from hyperblebbing strains [128-131]. Vesicles from a non-pathogenic *Neisseria* may be included [132]. OMVs may be prepared without the use of detergents [133,134]. They may express non-Neisserial proteins on their surface [135]. They may be LPS-depleted. They may be mixed with recombinant antigens [118,136]. Vesicles from bacteria with different class I outer membrane protein subtypes may be used e.g. six different subtypes [137,138] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2, 10; P1.12-1,13; P1.7-2,4; P1.22,14; P1.7-1,1; P1.18-1,3,6.

Host Cells

The invention provides a bacterium which expresses a polypeptide of the invention. The bacterium may be a meningococcus or an *E. coli*. The bacterium may constitutively express the polypeptide, but in some embodiments expression may be under the control of an inducible promoter. The bacterium may hyper-express the polypeptide (cf. ref. 139). Expression of the polypeptide is ideally not phase variable.

The invention also provides outer membrane vesicles prepared from a bacterium of the invention (particularly from a meningococcus). It also provides a process for producing vesicles from a bacterium of the invention. Vesicles prepared from these strains preferably include the polypeptide of the invention, which should be in an immunoaccessible form in the vesicles i.e. an antibody which can bind to purified polypeptide of the invention should also be able to bind to the polypeptide which is present in the vesicles.

These outer membrane vesicles include any proteoliposomic vesicle obtained by disruption of or blebbing from a meningococcal outer membrane to form vesicles therefrom that include protein components of the outer membrane. Thus the term includes OMVs (sometimes referred to as 'blebs'), microvesicles (MVs [116]) and 'native OMVs' ('NOMVs' [117]).

MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 130 & 131 describe *Neisseria* with high MV production.

OMVs are prepared artificially from bacteria, and may be prepared using detergent treatment (e.g. with deoxycholate), or by non-detergent means (e.g. see reference 134). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [140 & 141] being preferred for treating *Neisseria*) at a pH sufficiently high not to precipitate the detergent [142]. Other techniques may be performed substantially in the absence of detergent [134] using techniques such as sonication, homogenisation, microfluidisation, cavitation, osmotic shock, grinding, French press, blending, etc. Methods using no or low detergent can retain useful antigens such as NspA and fHbp [134]. Thus a method may use an OMV extraction buffer with about 0.5% deoxycholate or lower e.g. about 0.2%, about 0.1%, <0.05% or zero.

A useful process for OMV preparation is described in reference 143 and involves ultrafiltration on crude OMVs, rather than instead of high speed centrifugation. The process may involve a step of ultracentrifugation after the ultrafiltration takes place. OMVs can also be purified using the two stage size filtration process described in ref. 154.

Vesicles for use with the invention can be prepared from any meningococcal strain. The vesicles will usually be from a serogroup B strain, but it is possible to prepare them from serogroups other than B (e.g. reference 142 discloses a process for serogroup A), such as A, C, W135 or Y. The strain may be of any serotype (e.g. 1, 2a, 2b, 4, 14, 15, 16, etc.), any serosubtype, and any immunotype (e.g. L1; L2; L3; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3.

Bacteria of the invention may, in addition to encoding a polypeptide of the invention, have one or more further modifications. For instance, they may have a modified fur gene [144]. Expression of nspA expression may be up-regulated with concomitant porA and cps knockout. Further knockout mutants of *N. meningitidis* for OMV production are disclosed e.g. in reference 150. Reference 145 discloses the construction of vesicles from strains modified to express six different PorA subtypes. Mutant *Neisseria* with low endotoxin levels, achieved by knockout of enzymes involved in LPS biosynthesis, may also be used [146,147]. Mutant *Neisseria* engineered to reduce or switch off expression of at least one gene involved in rendering toxic the lipid A portion of LPS, in particular of lpxl1 gene, can be used with the invention [148]. Similarly, mutant *Neisseria* engineered to reduce or switch off expression of at least one gene involved in the capsular polysaccharide synthesis or export, in particular of synX and/or ctrA genes can be used with the invention. These or others mutants can all be used with the invention.

Thus a strain used with the invention may in some embodiments express more than one PorA subtype. 6-valent and 9-valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12-1,13; P1.7-2,4; P1.22,14; P1.7-1,1 and/or P1.18-1,3,6. In other embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76).

In some embodiments a strain may hyper-express (relative to the corresponding wild-type strain) certain proteins. For instance, strains may hyper-express NspA, protein 287 [118], fHbp [139](including fHbp of the invention), TbpA and/or TbpB [136], Cu,Zn-superoxide dismutase, HmbR, etc.

A gene encoding a polypeptide of the invention may be integrated into the bacterial chromosome or may be present in episomal form e.g. within a plasmid.

Advantageously for vesicle production, a meningococcus may be genetically engineered to ensure that expression of the polypeptide is not subject to phase variation. Methods for reducing or eliminating phase variability of gene expression in meningococcus are disclosed in reference 149. For example, a gene may be placed under the control of a constitutive or inducible promoter, or by removing or replacing the DNA motif which is responsible for its phase variability.

In some embodiments a strain may include one or more of the knockout and/or hyper-expression mutations disclosed in references 122, 124, 128, and 150. For instance, following the guidance and nomenclature in these four documents, useful genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; or (d) CtrA, CtrB, CtrD, FrpB, OpA, OpC, PilC, PorB, SiaD, SynA, SynB, SynX and/or SynC.

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no α chain.

Depending on the meningococcal strain used for preparing the vesicles, they may or may not include the strain's native fHbp antigen [151].

In one preferred embodiment, a meningococcus does not express a functional MltA protein. As discussed in refs. 152 & 153, knockout of MltA (the membrane-bound lytic transglycosylase, also known as GNA33) in meningococcus provides bacteria which spontaneously release large amounts of membrane vesicles into culture medium, from which they can be readily purified. For instance, the vesicles can be purified using the two stage size filtration process of ref. 154, comprising: (i) a first filtration step in which vesicles are separated from the bacteria based on their different sizes, with the vesicles passing into the filtrate; and (ii) a second filtration step in which the vesicles are retained in the retentate. The MltA mutation (down-regulation or knockout) has been used in 'GMMA' vaccines [155], and can conveniently be combined with further down regulation or knockout of in particular of at least one gene involved in rendering toxic the lipid A portion of LPS, particularly of lpxl1 and/or of at least one gene involved in the capsular polysaccharide synthesis or export, particularly of synX and/or ctrA genes. GMMA (Generalized Modules for Membrane Antigens) are genetically detoxified OMV that are produced from meningococcal strains that have been engineered to release GMMA with reduced reactogenicity and increased immunogenicity. GMMA induce less proinflammatory cytokines than OMV when tested in the monocyte activation test (MAT).

A preferred meningococcal strain for a 'GMMA' vaccine using this approach expresses a mutant v2 fHbp and/or a mutant v3 fHbp of the invention, and expression can be driven by strong promoters. Vesicles released by this strain include the mutant v2 and/or v3 fHbp proteins in immunogenic form, and administration of the vesicles can provide bactericidal antibody response as discussed in reference 155. The strain can also express a v1 fHbp, or a v1 fHbp can instead be provided as a separate recombinant protein in soluble form (and the v1 fHbp can be a wild-type or a mutant sequence e.g. mutated to disrupt its ability to bind to fH, as discussed above). The invention provides such strains, and also provides the vesicles which these strains release e.g. as purified from culture media after growth of the strains. A preferred v2 mutant for expression in these strains has a mutation at S32 and/or L123 as discussed herein, and a preferred v3 mutant for expression in these strains has a mutation at S32 and/or L126 as discussed herein. Thus vesicles prepared from meningococci expressing these v2 and v3 mutant fHbp sequences are particularly preferred immunogens for use in vaccines of the invention. A useful wild-type v2 sequence for mutagenesis in this way comprises SEQ ID NO: 51 or SEQ ID NO: 54 (comprising ΔG form SEQ ID NO: 55), and a useful wild-type v3 sequence for mutagenesis in this way comprises SEQ ID NO: 52.

Useful promoters for use in such strains include those disclosed in references 156 and 157. For instance, the promoter can be: (a) the promoter from a porin gene, preferably porA or porB, particularly from *N. meningitidis*; or (b) a rRNA gene promoter (such as a 16S rRNA gene), particularly from *N. meningitidis*. Where a meningococcal porin promoter is used, it is preferably from porA, and even more particularly a −10 region from a meningococcal porA gene promoter, and/or a −35 region from a meningococcal porA gene promoter (preferably wherein the −10 region and the −35 region are separated by an intervening sequence of 12-20 nucleotides, and wherein the intervening sequence either contains no poly-G sequence or includes a poly-G sequence having no more than eight consecutive G nucleotides). Where a rRNA gene promoter is used, it can comprise more particularly (i) a −10 region from a meningococcal rRNA gene promoter and/or (ii) a −35 region from a meningococcal rRNA gene promoter. It is also possible to use a hybrid of (a) and (b), for instance to have a −10 region from a porA promoter and a −35 region from a rRNA promoter (which can be a consensus −35 region). A useful promoter can thus be a promoter which includes either (i) a −10 region from a (particularly meningococcal) rRNA gene and a −35 region from a (particularly meningococcal) porA gene, or (ii) a −10 region from a (particularly meningococcal) porA gene and a −35 region from a (particularly meningococcal) rRNA gene.

If LOS is present in a vesicle it is possible to treat the vesicle so as to link its LOS and protein components ("intra-bleb" conjugation [150]).

General

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.). The term "consisting essentially of" limits the scope of a claim to the specified materials or steps "and those that do not materially affect the basic and novel characteristic(s)" of the claimed invention.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

"Sequence identity" can be determined by the Smith-Waterman homology search algorithm as implemented in the MPSRCH program (Oxford Molecular), using an affine gap search with parameters gap open penalty=12 and gap extension penalty=1, but is preferably determined by the Needleman-Wunsch global alignment algorithm [158], using default parameters (e.g. with Gap opening penalty=10.0, and with Gap extension penalty=0.5, using the EBLOSUM62 scoring matrix). This algorithm is conveniently implemented in the needle tool in the EMBOSS package [159]. Where the application refers to sequence identity to a particular SEQ ID, the identity should be calculated over the entire length of that SEQ ID.

The term "fragment" in reference to polypeptide sequences means that the polypeptide is a fraction of a full-length protein. Such fragments may possess qualitative biological activity in common with the full-length protein, for example, a fragment may contain or encode one or more epitopes, such as immunodominant epitopes, that allow similar immune response to be raised to the fragment as to the full length sequence. Polypeptide fragments generally have an amino (N) terminus portion and/or carboxy (C) terminus portion deleted as compared to the native protein, but wherein the remaining amino acid sequence of the fragment is identical to the amino acid sequence of the native protein. Polypeptide fragments may contain, for example: about 8, 10, 12, 14, 16, 18, 20, 22, 24, 26, 28, 30, 32, 24, 26, 28, 40, 45, 50, 55, 60, 70, 80, 90, 100, 150, 200, 240, 241, 242, 243, 244, 245, 246, 247, 248, 249, 250, 251, 252, 253, 254, 255, 256, 257, 258, 259, 260, 261, 262 contiguous amino acids, including all integers in between, of a reference polypeptide sequence, for example between 50 and 260, 50 and 255, 50 and 250, 50 and 200, 50 and 150 contiguous amino acids of a reference polypeptide sequence. The term fragment explicitly excludes full length fHbp polypeptides and mature lipoproteins thereof.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

In general, the invention does not encompass the various fHbp sequences specifically disclosed in references 2, 3, 5, 6, 7, 160, 161, 162, 163, 164, 165, 166, and 167.

SPECIFIC EMBODIMENTS OF THE INVENTION

Figure 1:
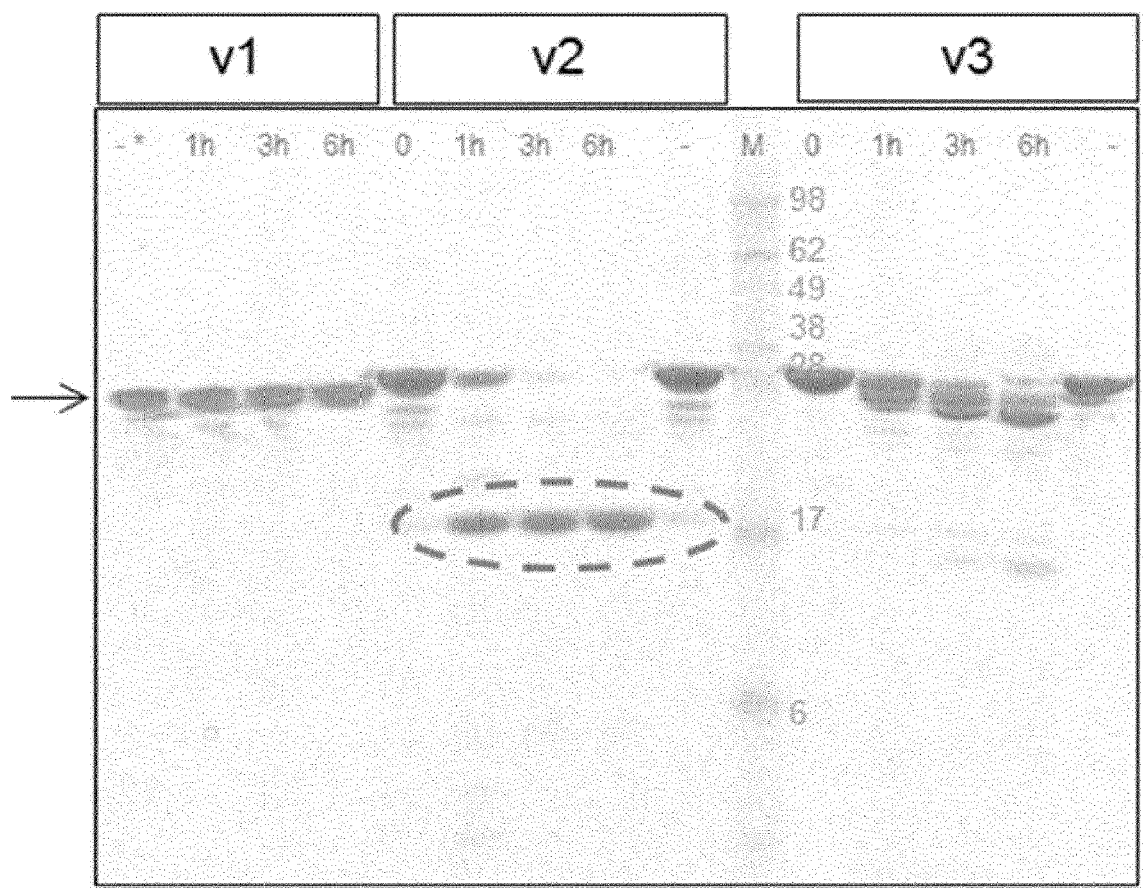
FIG. 1 shows the different sensitivity of fHbp variants to chymotrypsin cleavage. The arrow shows the position of full-length fHbp proteins.

The invention provides the following specific numbered embodiments:

I. A mutant v3 or v2 fHbp which has increased stability relative to a wild-type fHbp and, preferably, also has lower affinity for human factor H than a wild-type fHbp;
for instance:
(A) a polypeptide comprising a mutant fHbp v2 amino acid sequence, wherein: (a) the amino acid sequence has at least 80% sequence identity to SEQ ID NO: 5 and/or comprises a fragment of SEQ ID NO: 5 which is at least 7 amino acids long and contains at least one of the residues listed in (b); but (b) the amino acid sequence differs from SEQ ID NO: 5 at one or more of the following residues: 32, 33, 39, 41, 69, 100, 113, 122, 123, 124, 125, 126, 127, 128, 151, 239, and/or 240; provided that:
if the mutant fHbp v2 amino acid sequence includes a substitution only at residue 32, either this substitution is not with alanine or at least one further residue listed in (b) is substituted;
if the mutant fHbp v2 amino acid sequence includes a substitution only at residue 113, either this substitution is not with alanine or at least one further residue listed in (b) is substituted.
if the mutant fHbp v2 amino acid sequence includes a substitution only at residue 122, either this substitution is not with alanine or at least one further residue listed in (b) is substituted;
if the mutant fHbp v2 amino acid sequence includes a substitution at residue 123, either this substitution is not with alanine or at least one further residue listed in (b) is substituted;

if the mutant fHbp v2 amino acid sequence includes a substitution only at residue 124, either this substitution is not with alanine or at least one further residue listed in (b) is substituted;

if the mutant fHbp v2 amino acid sequence includes a substitution only at residue 127, either this substitution is not with alanine or at least one further residue listed in (b) is substituted; and if the mutant fHbp v2 amino acid sequence includes a substitution only at residue 240, either this substitution is not with alanine or at least one further residue listed in (b) is substituted.

or (B) a polypeptide comprising a mutant fHbp v3 amino acid sequence, wherein: (a) the amino acid sequence has at least 80% sequence identity to SEQ ID NO: 17 and/or comprises a fragment of SEQ ID NO: 17 which is at least 7 amino acids long and contains at least one of the residues listed in (b); but (b) the amino acid sequence differs from SEQ ID NO: 17 at one or more of the following residues: 32, 33, 39, 41, 72, 103, 116, 125, 126, 127, 128, 129, 130, 131, 154, 242, and/or 243; provided that:

if the mutant fHbp v3 amino acid sequence includes a substitution at residue 32, either this substitution is not with alanine or at least one further residue listed in (b) is substituted;

if the mutant fHbp v3 amino acid sequence includes a substitution at residue 113, either this substitution is not with alanine or at least one further residue listed in (b) is substituted.

if the mutant fHbp v3 amino acid sequence includes a substitution only at residue 125, either this substitution is not with alanine or at least one further residue listed in (b) is substituted;

if the mutant fHbp v3 amino acid sequence includes a substitution at residue 126, either this substitution is not with alanine or at least one further residue listed in (b) is substituted;

if the mutant fHbp v3 amino acid sequence includes a substitution at residue 127, either this substitution is not with alanine or at least one further residue listed in (b) is substituted;

if the mutant fHbp v3 amino acid sequence includes a substitution at residue 130, either this substitution is not with alanine or at least one further residue listed in (b) is substituted; and if the mutant fHbp v3 amino acid sequence includes a substitution only at residue 243, either this substitution is not with alanine or at least one further residue listed in (b) is substituted.

2. The polypeptide of embodiment 1(B), wherein the amino acid sequence differs from SEQ ID NO: 17 by substitution at one or more of the residues listed in (b); for instance, where the substitution(s) are selected from the group consisting of: S32V; I33C; L39C; L41C; F72C; V103T; T116S; F125C; L126R; V127I; S128G or S128T; G129D; L130I; G131A; S154C; H242R; and E243H.

3. The polypeptide of embodiment 1(B) or embodiment 2, comprising more than one substitution at the residues listed in (b), and selected from groups 3A to 30 as noted above.

4. The polypeptide of embodiment 1(A), wherein the amino acid sequence differs from SEQ ID NO: 5 by substitution at one or more of the residues listed in (b); for instance, where the substitution(s) are selected from the group consisting of: S32V; V33C; L39C; L41C; F69C; V100T; I113S; F122C; L123R; V124I; S125G or S125T; G126D; L127I; G128A; S151C; H239R; and E240H.

5. The polypeptide of embodiment 1(A) or embodiment 4, comprising more than one substitution at the residues listed in (b), and selected from groups 2A to 20 as noted above.

6. The polypeptide of any of embodiments 1-5, also including one or more further mutation(s) which disrupt(s) the polypeptide's ability to bind to human factor H; for instance, in v2 including a substitution at one or more of R73, D203, E210, G228, S121, F122, L123, A192, E194, V199, I200, L201, T213, H215, F219, T231, and E240, or in v3 including a substitution at one or more of Q35, I178, L87, A88, L126, V127, V202, E213, T216, T234, V241, and E243.

7. A polypeptide comprising:

amino acid sequence SEQ ID NO: 44, optionally with 1, 2, 3, 4, or 5 single amino acid substitutions, deletions and/or insertions, wherein the polypeptide can elicit antibodies which bind to a meningococcal fHbp polypeptide consisting of the amino acid sequence of SEQ ID NO: 40 (for example, comprising amino acid sequence SEQ ID NO: 44 with 1, 2, or 3 single amino acid substitutions), but not mutated at residue V32 or R126;

amino acid sequence SEQ ID NO: 45, optionally with 1, 2, 3, 4, or 5 single amino acid substitutions, deletions and/or insertions, wherein the polypeptide can elicit antibodies which bind to a meningococcal fHbp polypeptide consisting of the amino acid sequence of SEQ ID NO: 2 (for example, comprising amino acid sequence SEQ ID NO: 45 with 1, 2, or 3 single amino acid substitutions), but not mutated at residue V32 or R123;

a fHbp v3 amino acid sequence, wherein the v3 amino acid sequence is identical to a v3 wild-type amino acid sequence except for a mutation at the amino acid position corresponding to Leu-126 of SEQ ID NO: 17, provided that the mutation is not a substitution to alanine (e.g. wherein the mutation is a substitution to arginine);

a fHbp v2 amino acid sequence, wherein the v2 amino acid sequence is identical to a v2 wild-type amino acid sequence except for a mutation at the amino acid position corresponding to Leu-123 of SEQ ID NO: 5, provided that the mutation is not a substitution to alanine (e.g. wherein the mutation is a substitution to arginine); or amino acid sequence SEQ ID NO: 47, optionally with 1, 2, 3, 4, or 5 single amino acid substitutions, deletions and/or insertions, wherein the polypeptide can elicit antibodies which bind to each of: a meningococcal fHbp polypeptide consisting of the amino acid sequence of SEQ ID NO: 46; a meningococcal fHbp polypeptide consisting of the amino acid sequence of SEQ ID NO: 4; and a meningococcal fHbp polypeptide consisting of the amino acid sequence of SEQ ID NO: 40 (for instance, consisting of amino acid sequence SEQ ID NO: 48).

8. A plasmid or other nucleic acid comprising a nucleotide sequence encoding the polypeptide of any of embodiment 1 to 7.

9. A host cell transformed with the plasmid of embodiment 8; e.g. wherein the cell is a meningococcal bacterium, such as a meningococcal bacterium having down-regulation or knockout of mltA and also optionally has down-regulation or knockout of: (i) at least one gene involved in rendering the lipid A portion of LPS toxic, particularly of lpxl1; and/or (ii) at least one gene involved in capsular polysaccharide synthesis or export, particularly of synX and/or ctrA.

10. Membrane vesicles prepared from the host cell of embodiment 9, wherein the vesicles include a polypeptide of any one of embodiments 1 to 7.

11. An immunogenic composition comprising a polypeptide of any one of embodiments 1 to 7, or a vesicle of embodiment 10.

12. The composition of embodiment 11, further comprising a second polypeptide that, when administered to a mammal, elicits an antibody response that is bactericidal against meningococcus.

13. The composition of embodiment 11 or 12, further comprising (i) a conjugated capsular saccharide from N. meningitidis serogroup A, C, W135 and/or Y and/or (ii) a conjugated capsular saccharide from S. pneumoniae 14. A method for raising an antibody response in a mammal, comprising administering an immunogenic composition of any of embodiments 11 to 13.

MODES FOR CARRYING OUT THE INVENTION fHbp Mutations

The v2 fHbp is recognised as being unstable. To analyse the underlying structural reasons for this undesirable property, with a view to engineering the sequence to improve stability, the inventors analysed sequence alignments and 3D structures of fHbp polypeptides. One area of particular interest was the structural interface between the N-terminal and C-terminal domains [168].

The inventors identified the mutations explained in Table 1. Three of the positions identified for mutation overlap with references 24 and 25, but the invention does not encompass the polypeptides reported in the prior art i.e. where the polypeptides include substitutions solely at these positions by alanine. For instance, E240 can be substituted with histidine to match v1, and is ideally paired with substitution at residue H239 (mutants #1 and #11). Similarly, if F122 is substituted then it is preferably paired with substitution at S151, both with cysteine to permit formation of a disulfide bridge (mutant #10). Also, if L123 is substituted then it is can be substituted with arginine (rather than alanine), or it can be paired with substitution at other residues e.g. at S32 (see mutant #3), at S125 (see mutants #20 and #22), or with substitution at residues 124-128 (see mutant #12).

Stability Studies

Unstable proteins tend to be less folded and for this reason prone to cleavage and degradation by proteases. FIG. 1 shows that v2 fHbp is more sensitive to chymotrypsin degradation than v1 and v3, and so this test can be used to assess stability of the mutant proteins.

For FIG. 1, wild-type fHbp v1, v2 and v3 were prepared at 0.5 mg/μL in 50 mM Tris-HCl, 150 mM NaCl, pH 8. Chymotrypsin was added at 1:100 (w/w) ratio. Samples were incubated at 24° C., 50 mL volume, no shaking. Samples were extracted and boiled for 0, 1, 3, or 6 hours; then run on 12% bis-Tris gel (MES buffer). The left-hand lane, marked *, indicates a sample incubated for 6 hours without protease.

Figure 2:
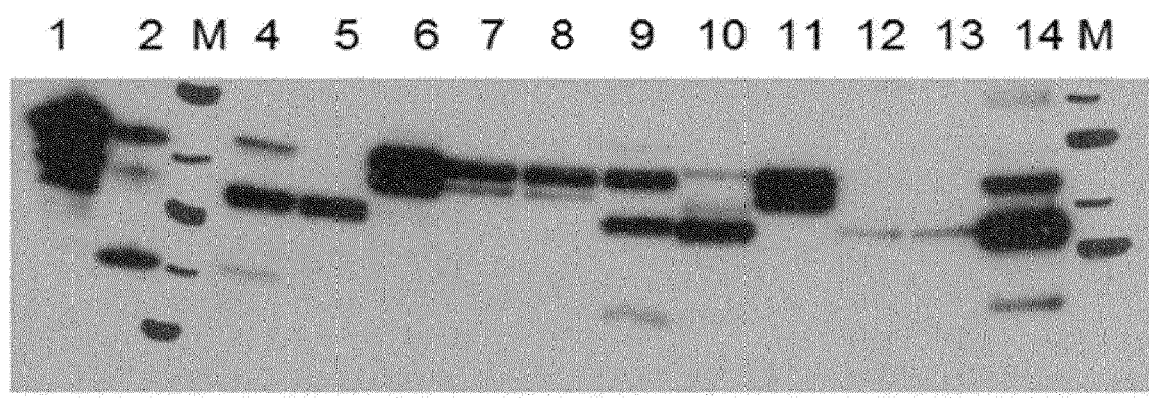
FIG. 2 shows western blot analysis of v2 mutants. Lanes are: (1 & 2) Recombinant purified v2 wild type; (4) v2 wild type lysate; (5) mutant #1; (6) mutant #2; (7) mutant #4; (8) mutant #5; (9) mutant #7; (10) mutant #8; (11) mutant #12; (12) mutant #14 (13) mutant #15; (14) fHbp var2 NΔG-trx control i.e. v2 protein where N-terminal sequence GPDS-DRLQQRR (SEQ ID NO: 37) is replaced by GSKDISS (SEQ ID NO: 38). Lanes 2-14 included chymotrypsin. M is molecular markers.
Figure 3:
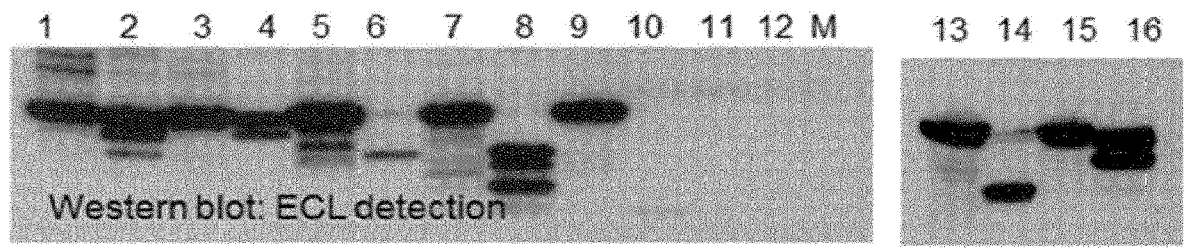
FIG. 3 shows further western blot analysis of v2 mutants. Lanes are: (1&2) mutant #3; (3&4) mutant #6; (5&6) mutant #9; (7&8) mutant #10; (9&10) mutant #13; (11&12) Δgono; (13&14) v2 wildtype; (15&16) mutant #22. Odd-numbered lanes are for proteins which were incubated without chymotrypsin, whereas even-numbered lanes were for proteins incubated with chymotrypsin. The 'Δgono' protein is a recombinant v2 where the N-terminal sequence (SEQ ID NO: 37) has been removed.
Figure 4:
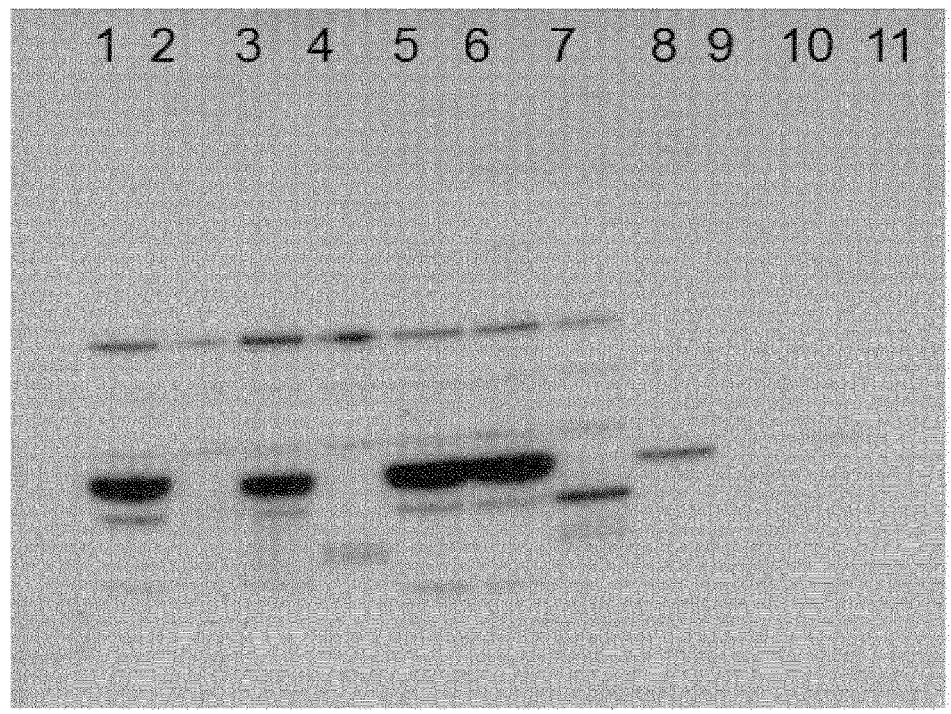
FIG. 4 shows further western blot analysis of v2 mutants. Lanes are: (l&2) mutant #11; (3&4) N-trx; (5-7) mutant #19; (8&9) mutant #20; (10&11) mutant #21. Lanes 2, 4, 7, 9 and 11 proteins which were incubated with chymotrypsin, whereas the other lanes had no chymotrypsin. The 'N-trx' protein is a recombinant v2 where the N-terminal sequence (SEQ ID NO: 37) is replaced by SEQ ID NO: 39.

Cell lysates of E. coli expressing the recombinant proteins have been incubated with 1:100 w/w ratio chymotrypsin for 3 hours at 25° C. The degradation pattern has been analysed by Western blotting following the incubation with an immune polyclonal serum elicited in rabbit against all three fHbp variants. The presence of cleavage products at lower apparent molecular weight (FIGS. 2-4) is interpreted as an indication of instability, whereas persistence of a band corresponding to an apparent MW of ~30 kDa is interpreted as an indication of increased stability. Mutants #1-6, #12 and #22 all showed increased resistance to chymotrypsin cleavage compared to the wild type v2.

DSC has been used as an independent approach to assess the effects of mutations on the stability of purified recombinant fHbp v2 proteins. $T_m$ (melting temperature) measured by DSC corresponds to the temperature at which the analysed protein is 50% in the folded state and 50% in the unfolded state. Changes which stabilize the conformation of a protein will increase Tm, whereas destabilizing changes will decrease Tm. As seen in FIG. 3D of ref. 24, the DSC profile of wild-type v2 fHbp shows two Tm values: $T_{m1}$ at ~40° C., which corresponds to the melting temperature of the N-terminal domain, and $T_{m2}$ at ~80° C. corresponding to the melting temperature of the C-terminal domain. Values of $T_{m1}$ and $T_{m2}$ for analyzed mutants are shown in Table 1. Mutants #2, #4, #5, #12, #19 and #21 showed increased $T_m$ of the N-terminal domain relative to the wild-type protein, and this effect was more marked for mutants #2, #4 and #12.

Size-exclusion chromatography (SEC) was used to assess the percentage of monomeric protein, and results are also shown in Table 1.

Mutants #2, #3, and #4

Figure 5:
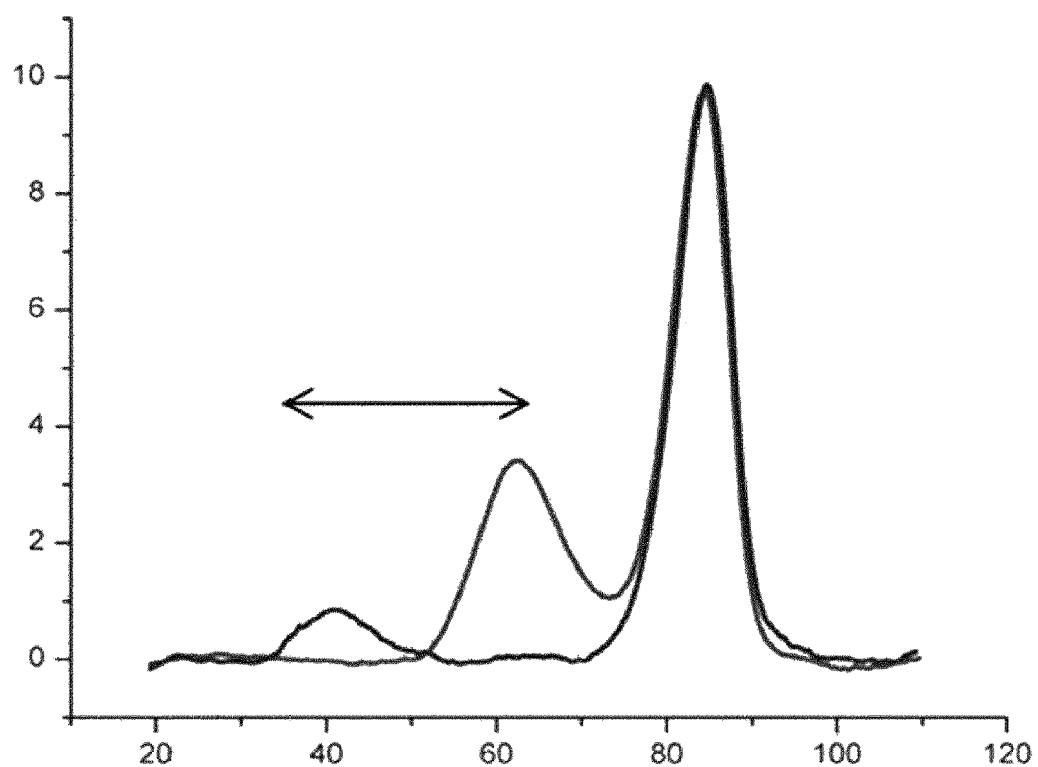
FIG. 5 shows DSC results for wild-type and S58V/L149R mutant v2 fHbp. The C-terminal domain was unaffected by the mutation, but the Tm of the N-terminal domain was increased by >20° C. (marked with the arrow). The y-axis shows Cp (kcal/mol/° C.), and the x-axis show temperature (° C.).

Mutant #3 (group 2B) gave the best overall results in the v2 stability studies. This protein (SEQ ID NO: 20) includes mutations at Ser-58 (S32 in SEQ ID NO: 5) and Leu-149 (L123 in SEQ ID NO: 5), with substitutions by Val and Arg, respectively. The mutant v2 protein (SEQ ID NO: 20, comprising SEQ ID NO: 45) was analysed by DSC and, compared to the wild-type sequence, the $T_m$ of its N-terminus domain is >20° C. higher (FIG. 5).

In a serum bactericidal assay this v2 mutant could compete for binding to human antibodies which had been raised using a wild-type v2 sequence.

Figure 6:
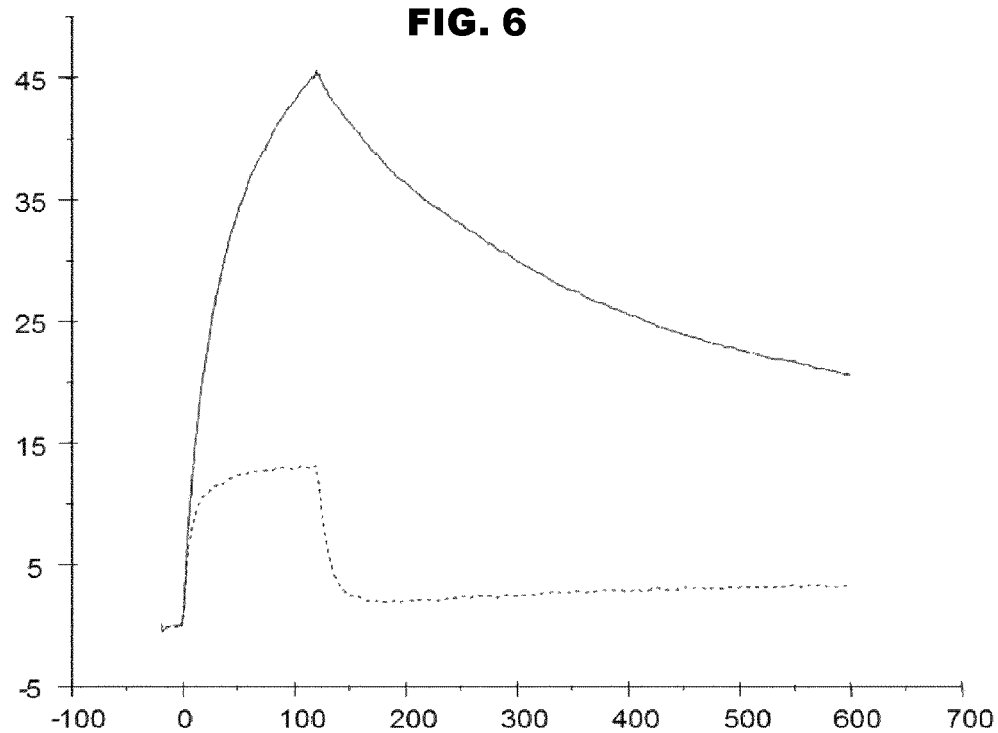
FIG. 6 shows the SPR response of wild-type (solid) and mutant (dashed) v2 fHbp.

Although the S58V and L149R mutations had been introduced to improve stability, and did indeed achieve this goal, FIG. 6 shows that the mutant v2 polypeptide (dotted line) surprisingly showed much reduced binding to fH compared to the wild-type v2 sequence (solid line) when measured by surface plasmon resonance against immobilised fH. The S58V mutation on its own had little impact on fH binding, and the S58V/L149R double mutant showed higher fH binding than fHbp carrying only the L149R mutant.

When mutant #3 was further combined with the 'E313A' mutation in v2 there was a complete loss of fH binding as assessed by SPR.

The equivalent mutations were introduced into a v3 sequence (SEQ ID NO: 17), to give v3 mutant SEQ ID NO: 44. The effects of the individual S58V and L149R mutations on fH binding were studied in v3 (i.e. the v3 equivalents of v2 mutants #2 and #4). Thus, numbered according to SEQ ID NO: 17, mutation S32V or L126R was introduced into the v3 sequence. These two mutants were compared to two different wild-type v3 sequences, and also to the 'E313A' mutant which is known to disrupt fH binding in v3 [23].

Figure 7:
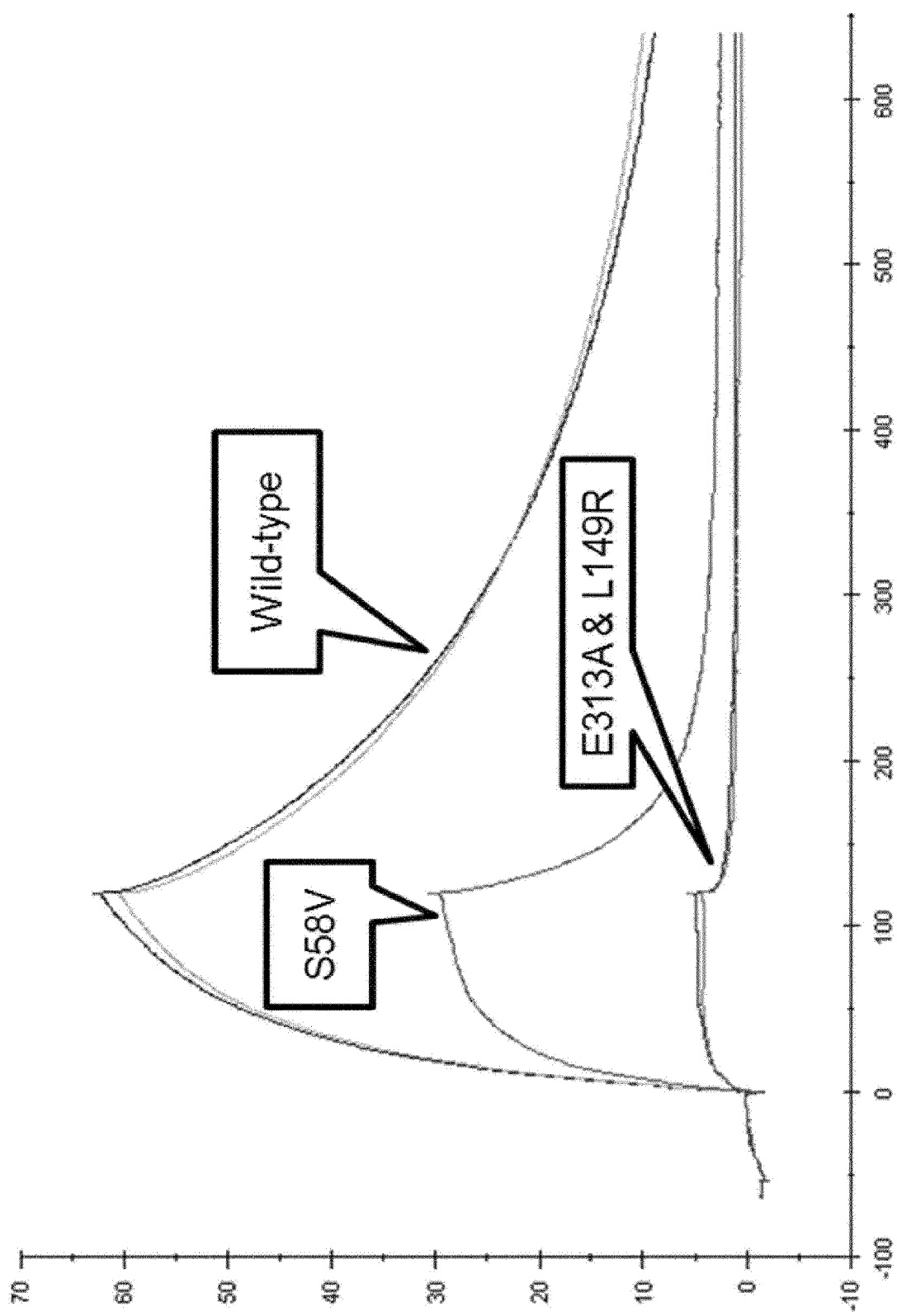
FIG. 7 shows the SPR response of v3 fHbp, either as wild-type (top) or with various mutations.

As shown in FIG. 7, wild-type v3 binds fH (top two lines). The S58V mutation, which was designed to improve stability, reduced the SPR peak value by about 2-fold. Most surprisingly, the L149R mutation (again, designed to improve stability) reduced fH affinity to a similar level to the known E313A mutant (bottom two lines).

The S58V and L149R mutations in v3 were also studied by DSC, and were found to increase the N-terminal Tm by 5.5° C. (S58V) or by 6.7° C. (L149R) relative to wild-type. The Tm of both mutants was higher than seen in the v2 double mutant (63.5° C.—see Table 1). The L149R v3 mutant also showed a higher Tm value for its C-terminal domain, whereas there was almost no shift here for the S58V v3 mutant. SPR showed that fH binding by mutant #2 was reduced by about a half, but for mutant #4 fH affinity was reduced to a similar level to the known E313A mutant (as also seen with v2). When the two mutations were combined (i.e. mutant #3) the $T_m$ increase compared to wild-type was 11.2° C. When the 'E313A' mutation was added to mutant #3 fH binding was almost completely eliminated, although the T, of the N-terminal domain also decreased by 2.9° C. when compared to mutant #3 (while remaining 8.3° C. higher than v3 wild-type). The 'E313A' mutation alone was much less stable than wild-type, showing a Tm decrease of 6.3° C.

Thus mutations #2 and #4 can be used alone, or in combination (i.e. mutant #3), optionally with further mutations, to stabilise v2 or v3 fHbp but also to disrupt fH affinity.

A serum bactericidal assay was used for assessing the immunogenic efficacy of mutants #3 and #4 in v2 and v3. In addition, the 'E313A' mutant was also tested in v2 and v3, either alone or in combination with the #3 mutations. Wild-type v2 and v3 fHbp were also tested for comparison. The proteins were administered at 20 µg/dose with an aluminium hydroxide adjuvant and the resulting sera were tested for bactericidal activity against a panel of seven strains (four v2 strains, three v3 strains) including strains which express the same fHbp as the starting wild-type fHbp sequences (i.e. v2 sequence 2.16 and v3 sequence 3.42).

Results for the v2 proteins were as follows (SEQ ID is for the ΔG form; *=homologous fHbp):

| Protein | SEQ ID | SBA against v2 strains | | | | SBA against v3 strains | | |
|---|---|---|---|---|---|---|---|---|
| | | v2.16* | v2.19 | v2.21 | v2.24 | v3.42* | v3.28 | v3.30 |
| w.t. | 5 | 32768 | 32 | 32 | 1024 | >32768 | <16 | 32 |
| #4 | 21 | 32768 | <16 | <16 | 128 | 1024 | <16 | 16 |
| #3 | 45 | 4096 | 32 | <16 | <16 | >32768 | 128 | <16 |
| #3 + E313A | 57 | 4096 | 16 | <16 | <16 | >32768 | <16 | <16 |
| E313A | 56 | 128 | 16 | <16 | <16 | 4096 | <16 | <16 |

Results for the v3 proteins were as follows:

| Protein | SEQ ID | SBA against v3 strains | | | SBA against v2 strains | | | |
|---|---|---|---|---|---|---|---|---|
| | | v3.42* | v3.28 | v3.30 | v2.16* | v2.19 | v2.21 | v2.24 |
| w.t. | 17 | >32768 | 512 | 1024 | 1024 | 32 | 64 | 256 |
| #4 | 53 | 1024 | <16 | 16 | <16 | 16 | <16 | 128 |
| #3 | 44 | 4096 | 32 | 16 | 4096 | <16 | 16 | 16 |
| #3 + E313A | 43 | 256 | <16 | 16 | 64 | <16 | <16 | 16 |
| E313A | 41 | 4096 | 32 | 256 | 8192 | 32 | 32 | 128 |

Combination of Mutants #2 and #12

Mutants #2 and #12 each showed improvements in v2 stability, so these two mutants were combined into a single fHbp (SEQ ID NO: 58, ΔG form). Compared to mutant #12 the N-terminal $T_m$ of this combined mutant increased by a further 4.2° C., giving the highest $T_m$ of any of the tested mutant v2 proteins. Furthermore, it showed a strongly reduced fH binding (SPR peak value reduced about 8×).

Mutant Fusion Protein

Mutant v2 and v3 sequences were fused via a GSGGGG linker (SEQ ID NO: 50), also with a mutant v1 sequence, to give SEQ ID NO: 48. This sequence includes the S58V and L149R mutations for both v2 and v3, and the R41 S mutation [21] for vi. SEQ ID NO: 47 includes, from N-terminus to C-terminus: v2 mutant #3 (SEQ ID NO: 45); v3 mutant #3 (SEQ ID NO: 44); and v1 'R41S' mutant (SEQ ID NO: 49), connected by the glycine-rich linker sequence, SEQ ID NO: 50. The fusion protein can conveniently be expressed by adding a N-terminus sequence of Met-[SEQ ID NO: 37]-, thus providing a mature protein SEQ ID NO: 48.

This fusion protein thus takes advantage of the observation that mutant #3 provides for both v2 and v3 a large increase in stability ($T_m$) and a large decrease in fH affinity. For v1 the R41 S mutation has little effect on thermal stability but strongly reduces fH binding.

Figure 8:
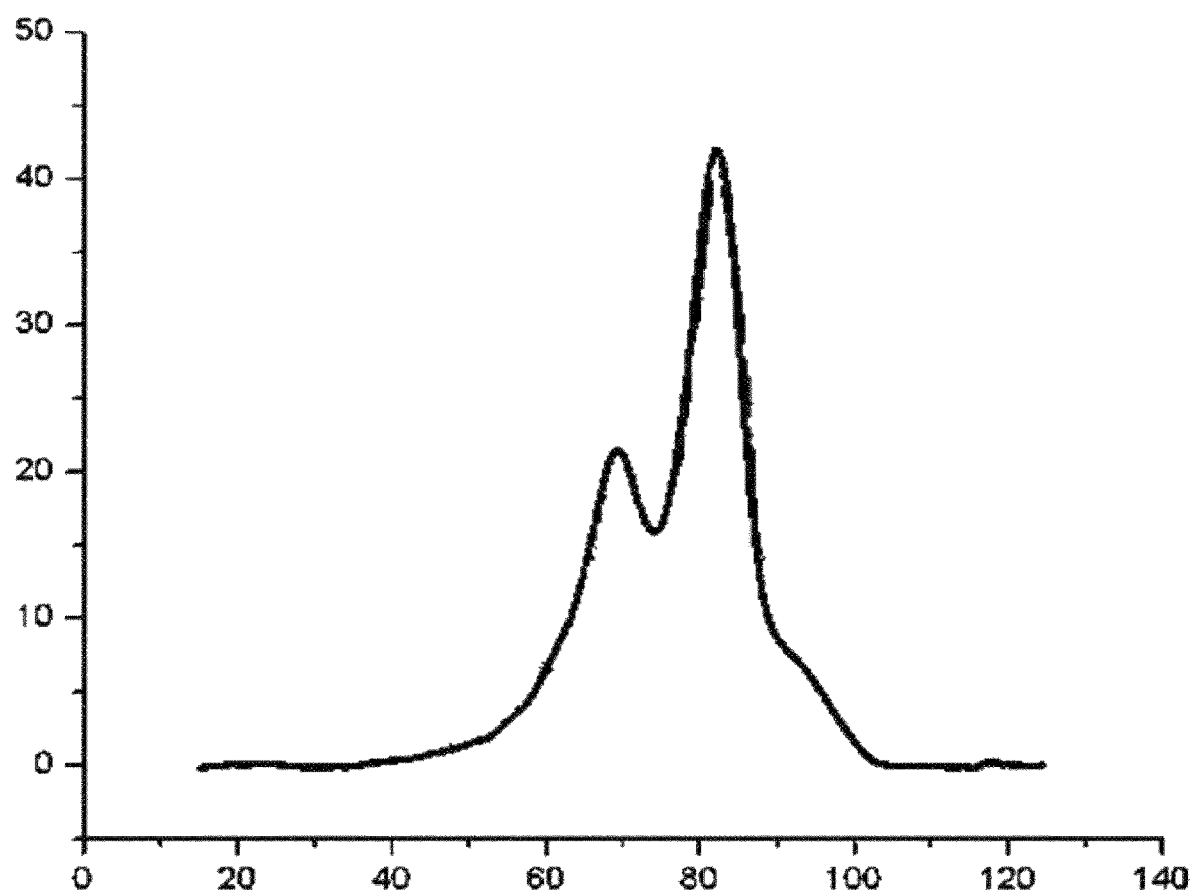
FIG. 8 shows DSC results for the triple fusion protein of SEQ ID NO: 48. The axes are as in FIG. 5.

DSC studies of the triple fusion protein (FIG. 8) show that the three N-terminal transitions fall together in a broad peak centred at 68° C. The three C-termini transitions also fall together. UPLC showed that the protein was 94.9% pure, and HPLC analysis showed <1.5% oligomers.

Mutant Proteins Expressed in 'GMMA' Membrane Vesicles

A v1 meningococcal strain was prepared with knockouts of mltA, lpxL1 and synX to provide a genetic background for hyper-expressing v2 and v3 fHbp lipoproteins under the control of the 'ST2' promoter [157] in a 'GMMA' vaccine. The v2 genes were integrated into the genome at the deleted lpxL1 locus whereas the v3 genes were integrated at the synX locus. In addition, the native v1 fHbp gene was deleted so that v2 and v3 could be studied without interference.

Mutants #3 and #4 were tested for v2, and mutant #4 was tested for v3. In addition, a strain with both of the v2 and v3 #4 mutants was prepared. For these bacteria fHbp expression and fH binding were assessed by FACS.

For strains expressing only v2 fHbp FACS showed that the various proteins were expressed at similar levels, at levels 2 logs higher than the background Δfhbp strain. In terms of fH binding, however, mutants #3 and #4 showed much less binding, with binding in mutant #4 being only slightly above background. These results mirror the SPR data obtained with recombinant v2 proteins.

For the strain expressing v3 mutant #4 FACS showed full expression of fHbp, but its fH binding was abolished (matching the fH binding seen with the 'H222R' mutation [19,25]).

For the strain expressing mutant #4 from v2 and v3, both fHbp proteins could be detected by FACS but fH binding was only slightly above that seen in the background Δfhbp strain.

Western blot analysis was used to test the stability of fHbp expression in these bacteria when growing in liquid culture for 6 days. Expression of mutant v2 proteins remained stable over time, even when v3 was co-expressed. Expression of mutant v3 proteins also remained stable, except in the strain expressing both the v2 and v3 mutant, where v3 expression declined over time.

It will be understood that the invention is described above by way of example only and modifications may be made whilst remaining within the scope and spirit of the invention.

REFERENCES

[1] WO99/57280.
[2] Masignani et al. (2003) *J Exp Med* 197:789-799.
[3] Welsch et al. (2004) *J Immunol* 172:5605-15.
[4] Hou et al. (2005) *J Infect Dis* 192(4):580-90.
[5] WO03/063766.
[6] Fletcher et al. (2004) *Infect Immun* 72:2088-2100.
[7] Zhu et al. (2005) *Infect Immun* 73(10):6838-45.
[8] Cendron et al. (2011) *Acta Crystallogr Sect F Struct Biol Cryst Commun.* 67:531-5.
[9] Mascioni et al. (2009) *J Biol Chem* 284:8738-46.
[10] Pizza et al. (2008) *Vaccine* 26 Suppl 8:I46-8.
[11] Malito et al. (2013) *PNAS USA* 110:3304-9.
[12] Marshall et al. (2012) *Pediatr Infect Dis J* 31:1061-8.
[13] McNeil et al. (2013) *Microbiol Mol Biol Rev* 77:234-52.
[14] Serruto et al. (2012) *Vaccine* 30 Suppl2: B87-97.
[15] Scarselli et al. (2011) *Sci Transl Med* 3:91ra62.
[16] WO2011/051893.
[17] WO2010/046715.
[18] Schneider et al. (2009) *Nature* 458:890-5.
[19] WO2011/126863.
[20] Beernink et al. (2010) *Clin Vaccine Immunol* 17:1074-8.
[21] Beernink et al. (2011) *J Immunol* 186:3606-14.
[22] Rossi et al. (2013) *Vaccine* 31:5451-7.
[23] van der Veen et al. (2014) *Infect Immun* PMID 24379280.
[24] Johnson et al. (2012) *PLoS Pathogen* 8:e1002981.
[25] Pajon et al. (2012) *Infect Immun* 80:2667-77.
[26] Granoff et al. (2013) *Clin Vaccine Immunol* 20:1099-107.
[27] Beernink et al. (2008) *Infect Immun* 76:4232-40.
[28] Scarselli et al. (2009) *J Mol Biol* 386:97-108.
[29] Giuntini et al. (2012) *PLoS One* 7:e34272.
[30] Vu et al. (2012) *Sci Rep* 2:341.
[31] Faleri et al. (2013) *FASEB J* fj.13-239012.
[32] Johnson (2013) *Arch Biochem Biophys* 531:100-9.
[33] Bruylants et al. (2005) *Current Medicinal Chemistry* 12:2011-20.
[34] Veggi et al. (2012) *Biochemistry* 51:9384-93.
[35] WO2014/030003.
[36] Jongerius et al. (2013) *PLoS Pathog* 9(8): e1003528.
[37] Pizza et al. (2000) *Science* 287:1816-1820.
[38] WO2007/028408.
[39] http://pubmlst.org/neisseria/
[40] Budroni et al. (2011) *PNAS USA* 108:4494-99.
[41] Goldschneider et al. (1969) *J. Exp. Med.* 129:1307-26.
[42] Santos et al. (2001) *Clinical and Diagnostic Laboratory Immunology* 8:616-23.
[43] Frasch et al. (2009) *Vaccine* 27S:B112-6.
[44] Gennaro (2000) *Remington: The Science and Practice of Pharmacy.* 20th edition, ISBN: 0683306472.
[45] WO03/009869.
[46] *Vaccine Design* . . . (1995) eds. Powell & Newman. ISBN: 030644867X. Plenum.
[47] Tettelin et al. (2000) *Science* 287:1809-1815.
[48] WO00/66741.
[49] Martin et al. (1997) *J Exp Med* 185(7):1173-83.
[50] WO96/29412.
[51] Perkins-Balding et al. (2003) *Microbiology* 149:3423-35.
[52] WO01/55182.
[53] WO01/38350.
[54] WO00/23595.
[55] Giuliani et al. (2006) *Proc Natl Acad Sci USA.* 103: 10834-9.
[56] WO2004/032958.
[57] Costantino et al. (1992) *Vaccine* 10:691-698.
[58] Costantino et al. (1999) *Vaccine* 17:1251-1263.
[59] WO03/007985.
[60] Watson (2000) *Pediatr Infect Dis J* 19:331-332.
[61] Rubin (2000) *Pediatr Clin North Am* 47:269-285, v.
[62] Jedrzejas (2001) *Microbiol Mol Biol Rev* 65:187-207.
[63] Bell (2000) *Pediatr Infect Dis J* 19:1187-1188.
[64] Iwarson (1995) *APMIS* 103:321-326.
[65] Gerlich et al. (1990) Vaccine 8 Suppl:S63-68 & 79-80.
[66] Vaccines (1988) eds. Plotkin & Mortimer. ISBN 0-7216-1946-0.
[67] Del Guidice et al. (1998) *Molecular Aspects of Medicine* 19:1-70.
[68] Gustafsson et al. (1996) *N. Engl. J. Med.* 334:349-355.
[69] Rappuoli et al. (1991) *TIBTECH* 9:232-238.
[70] Sutter et al. (2000) *Pediatr Clin North Am* 47:287-308.
[71] Zimmerman & Spann (1999) *Am Fam Physician* 59:113-118, 125-126.
[72] McMichael (2000) *Vaccine* 19 Suppl 1:S101-107.
[73] Schuchat (1999) *Lancet* 353(9146):51-6.
[74] WO02/34771.
[75] Dale (1999) *Infect Dis Clin North Am* 13:227-43, viii.
[76] Ferretti et al. (2001) *PNAS USA* 98: 4658-4663.
[77] Kuroda et al. (2001) *Lancet* 357(9264):1225-1240; see also pages 1218-1219.
[78] Jones (2001) *Curr Opin Investig Drugs* 2:47-49.
[79] Ravenscroft et al. (1999) *Vaccine* 17:2802-2816.
[80] WO03/080678.
[81] *Research Disclosure,* 453077 (January 2002).
[82] EP-A-0372501.
[83] EP-A-0378881.
[84] EP-A-0427347.
[85] WO93/17712.
[86] WO94/03208.
[87] WO98/58668.
[88] EP-A-0471177.
[89] WO91/01146.
[90] Falugi et al. (2001) *Eur J Immunol* 31:3816-3824.
[91] Baraldo et al. (2004) *Infect Immun* 72(8):4884-7.
[92] EP-A-0594610.
[93] Ruan et al. (1990) *J Immunol* 145:3379-3384.
[94] WO00/56360.
[95] Kuo et al. (1995) *Infect Immun* 63:2706-13.
[96] Michon et al. (1998) *Vaccine.* 16:1732-41.
[97] WO02/091998.
[98] WO01/72337.
[99] WO00/61761.
[100] WO00/33882
[101] Lees et al. (1996) *Vaccine* 14:190-198.
[102] WO95/08348.
[103] U.S. Pat. No. 4,882,317
[104] U.S. Pat. No. 4,695,624
[105] Porro et al. (1985) *Mol Immunol* 22:907-919.s
[106] EP-A-0208375
[107] WO00/10599
[108] Gever et al. Med. Microbiol. Immunol, 165:171-288 (1979).
[109] U.S. Pat. No. 4,057,685.
[110] U.S. Pat. Nos. 4,673,574; 4,761,283; 4,808,700.
[111] U.S. Pat. No. 4,459,286.
[112] U.S. Pat. No. 4,965,338

[113] U.S. Pat. No. 4,663,160.
[114] U.S. Pat. No. 4,761,283
[115] U.S. Pat. No. 4,356,170
[116] WO02/09643.
[117] Katial et al. (2002) *Infect Immun* 70:702-707.
[118] WO01/52885.
[119] European patent 0301992.
[120] Bjune et al. (1991) *Lancet* 338(8775):1093-1096.
[121] Fukasawa et al. (1999) *Vaccine* 17:2951-2958.
[122] WO02/09746.
[123] Rosenqvist et al. (1998) *Dev. Biol. Stand.* 92:323-333.
[124] WO01/09350.
[125] European patent 0449958.
[126] EP-A-0996712.
[127] EP-A-0680512.
[128] WO02/062378.
[129] WO99/59625.
[130] U.S. Pat. No. 6,180,111.
[131] WO01/34642.
[132] WO03/051379.
[133] U.S. Pat. No. 6,558,677.
[134] WO2004/019977.
[135] WO02/062380.
[136] WO00/25811.
[137] Peeters et al. (1996) *Vaccine* 14:1008-1015.
[138] Vermont et al. (2003) *Infect Immun* 71:1650-1655.
[139] WO2006/081259.
[140] European patent 0011243.
[141] Fredriksen et al. (1991) *NIPH Ann.* 14(2):67-80.
[142] WO01/91788.
[143] WO2005/004908.
[144] WO98/56901.
[145] Claassen et al. (1996) 14(10):1001-8.
[146] WO99/10497.
[147] Steeghs et al. (2001) *The EMBO Journal* 20:6937-6945.
[148] Fisseha et al. (2005) *Infect Immun* 73:4070-80.
[149] WO2004/015099.
[150] WO2004/014417.
[151] WO2004/046177.
[152] WO2006/046143.
[153] Adu-Bobie et al. (2004) *Infect Immun* 72:1914-19.
[154] WO2011/036562.
[155] Koeberling et al. (2014) *Vaccine* 32:2688-95.
[156] WO2013/033398.
[157] WO2013/113917.
[158] Needleman & Wunsch (1970) *J. Mol. Biol.* 48, 443-453.
[159] Rice et al. (2000) *Trends Genet* 16:276-277.
[160] WO01/64920.
[161] WO03/020756.
[162] WO2004/048404.
[163] WO2004/094596
[164] WO2006/024954.
[165] WO2007/060548.
[166] WO2009/104097.
[167] WO2013/132452.
[168] Krissinel & Henrick (2007) *J. Mol. Biol.* 372:774-97.

TABLE 1

| # | Residue(s)* | Mutation(s) | Notes | SEQ ID NO | Chym ** | Tm1 °C. | Tm2 °C. | Mon *** |
|---|---|---|---|---|---|---|---|---|
| 1 | H239 + E240 | R, H | Interface between N- and C-terminal domains. The aim is to mimic v1. An additional DSC transition was observed at 100.3° C., and some aggregation was detected. | 18 | Yes | N/A | 83.5 | 34.29 |
| 2 | S32 | V | N-terminal domain. Hydrophilic S32 side chain points into hydrophobic cavity. The aim is to increase hydrophobicity and stabilise the cavity. | 19 | Yes | 57.0 | 84.2 | 80.38 |
| 3 | S32 + L123 | V, R | Mutants #2 + #4 | 20 | Yes | 63.5 | 83.84 | 76.1 |
| 4 | L123 | R | N-terminal domain. In v1 the reverse change decreased stability [11]. | 21 | Yes | 54.1 | 84.1 | 89.97 |
| 5 | S125 + G126 | G, D | N-terminal domain. The aim is to mimic v1 | 22 | Yes | 52.3 | 83.3 | 90.48 |
| 6 | V100 + S125 + G126 | T, G, D | N-terminal domain. The aim is to mimic v1 | 23 | Yes | 52 | 83.7 | 86.41 |
| 7 | I113 | S | Surface loop of the N-terminal domain. Remove potential protease cleavage site from surface | 24 | No | ND | ND | ND |
| 8 | V33 + L39 | C, C | Core of the N-terminal domain. Introduce a S-S bridge. Some aggregation was detected. | 25 | No | 55.9 | 85 | 28.71 |
| 9 | L41 + F69 | C, C | Core of the N-terminal domain. Introduce a S-S bridge. | 26 | No | 46.4 | 84.4 | 33.5 + 53.22 |
| 10 | F122 + S151 | C, C | Core of the N-terminal domain. Introduce a S-S bridge. | 27 | No | — | — | — |
| 11 | V100 + S125 + G126 + H239 + E240 | T, G, D, R, H | Mutants #1 + #6 | 28 | No | 47.9 | 82.2 | 85.1 |
| 12 | L123 – G128 | RIGDIA | N-terminal domain. The aim is to mimic v1 in the whole region of 123-128 | 29 | Yes | 62.8 | 84.4 | 71.28 |
| 13 | V100 | T | Partial mutant #6 | 30 | No | 43 | 84.3 | 91.06 |
| 14 | L41 | C | Partial mutant #9. Some aggregation was detected. | 31 | No | — | 85 | 24.82 |
| 15 | F122 | C | Partial mutant #10. Some aggregation was detected. | 32 | No | — | 84.4 | 16.63 |
| 19 | S32 + S125 | V, T | N-terminal domain. Further increase hydrophobicity relative to #2 | 33 | No | 50.6 | 83.5 | 81.3 |
| 20 | S32 + S125 + L123 | V, T, R | Combine #4 + #19 | 34 | No | — | — | — |
| 21 | S32 + S125 | V, G | N-terminal domain. Further increase hydrophobicity relative to #2 | 35 | No | 52.8 | 84 | 75.3 |
| 22 | S32 + S125 + L123 | V, G, R | Combine #4 + #21 | 36 | Yes | — | — | — |
| 23 | S32 + L123 – G128 | RIGDIAS | Combine #2 + #12 | 62 | Yes | 66.3 | 84.7 | — |

*Numbered according to SEQ ID NO: 5; add +26 to match SEQ ID NOs: 18 to 39.
** Resistance to chymotrypsin cleavage.
*** % monomeric form

The invention claimed is:

1. A method for preventing or for protecting against Neisserial infection in a mammal comprising administering to the mammal an immunogenic composition comprising a fusion polypeptide, wherein the fusion polypeptide comprises a mutant v2 factor H Binding Protein (fHbp) polypeptide and a mutant v3 factor H Binding Protein (fHbp) polypeptide,
   (a) wherein the mutant v2 fHbp polypeptide comprises an amino acid sequence having at least 90% sequence identity to SEQ ID NO: 5 and includes an amino acid residue corresponding to residue 32 of SEQ ID NO: 5, wherein the amino acid sequence of the mutant v2 fHbp polypeptide differs from SEQ ID NO: 5 at residue 32 by the substitution S32V, and/or
   (b) wherein the mutant v3 fHbp polypeptide comprises an amino acid sequence having at least 90% sequence identity to SEQ ID NO: 17 and includes an amino acid residue corresponding to residue 32 from SEQ ID NO: 17, wherein the amino acid sequence of the mutant v3 fHbp polypeptide differs from SEQ ID NO: 17 at residue 32 by the substitution S32V.

2. The method of claim 1, wherein the mutant v2 fHbp polypeptide further differs from SEQ ID NO: 5 by substitution at one or more of L123, V124, S125, G126, L127 and/or G128.

3. The method of claim 2, wherein the substitution(s) are selected from the group consisting of: L123R; V124I; S125G or S125T; G126D; L127I; and G128A.

4. The method of claim 1, wherein the mutant v2 fHbp polypeptide further comprises a L123 mutation.

5. The method of claim 4, wherein the L123 mutation is a L123R mutation.

6. The method of claim 1, wherein the mutant v3 fHbp polypeptide further differs from SEQ ID NO: 17 by substitution at one or more of S32, I33, L39, L41, F72, V103, T116, F125, L126, V127, S128, G129, L130, G131, S154, H242, and/or E243.

7. The method of claim 6, wherein the substitution(s) are selected from the group consisting of: I33C, L39C, L41C, F72C, V103T, T116S, F125C, L126R, V127I, S128G or S128T, G129D, L130I, G131A, S154C, H242R, and E243H.

8. The method of claim 1, wherein the mutant v3 fHbp polypeptide further comprises a L126 mutation.

9. The method of claim 8, wherein the L126 mutation is L126R.

10. The method of claim 1, wherein the immunogenic composition further comprises a polypeptide having the amino acid sequence of SEQ ID NO: 45; wherein SEQ ID NO: 45 is modified by up to 5 single amino acid substitutions, deletions and/or insertions; and wherein the 5 single amino acid substitutions, deletions and/or insertions do not include amino acid positions V32 and R123.

11. The method of claim 1, wherein the immunogenic composition further comprises a polypeptide having the amino acid sequence of SEQ ID NO: 44, wherein SEQ ID NO: 44 is modified by up to 5 single amino acid substitutions, deletions and/or insertions, and wherein the 5 single amino acid substitutions, deletions and/or insertions do not include amino acid positions V32 and R126.

12. The method of claim 1, wherein the mutant v2 fHbp polypeptide and the mutant v3 fHbp polypeptide are arranged in the order v2 fHbp polypeptide followed by v3 fHbp polypeptide from N- to C-terminus.

13. The method of claim 12, wherein a linker having the amino acid sequence of SEQ ID NO: 50 is between the mutant v2 fHbp polypeptide and the mutant v3 fHbp polypeptide.

14. The method of claim 1, further comprising (i) a conjugated capsular saccharide from N. meningitidis serogroup A, C, W135 and/or Y.

15. The method of claim 1, wherein the immunogenic composition comprises the fusion polypeptide and one or more of (i) a Neisserial Heparin Binding Antigen (NHBA) polypeptide (ii) a Neisserial Adhesin (NadA) polypeptide and/or (iii) meningococcal outer membrane vesicles (OMVs).

16. The method according to claim 15, wherein the OMVs are from a serogroup B strain.

17. The method according to claim 15, wherein the immunogenic composition further comprises an aluminum hydroxide adjuvant.

18. The method according to claim 1, wherein said mammal is a human.

* * * * *

SEQUENCE LISTING

```
Sequence total quantity: 61
SEQ ID NO: 1              moltype = AA  length = 274
FEATURE                   Location/Qualifiers
source                    1..274
                          mol_type = protein
                          organism = Neisseria meningitidis
SEQUENCE: 1
MNRTAFCCLS LTTALILTAC SSGGGGVAAD IGAGLADALT APLDHKDKGL QSLTLDQSVR    60
KNEKLKLAAQ GAEKTYGNGD SLNTGKLKND KVSRFDFIRQ IEVDGQLITL ESGEFQVYKQ   120
SHSALTAFQT EQIQDSEHSG KMVAKRQFRI GDIAGEHTSF DKLPEGGRAT YRGTAFGSDD   180
AGGKLTYTID FAAKQGNGKI EHLKSPELNV DLAAADIKPD GKRHAVISGS VLYNQAEKGS   240
YSLGIFGGKA QEVAGSAEVK TVNGIRHIGL AAKQ                               274

SEQ ID NO: 2              moltype = AA  length = 273
FEATURE                   Location/Qualifiers
source                    1..273
                          mol_type = protein
                          organism = Neisseria meningitidis
SEQUENCE: 2
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 3              moltype = AA  length = 281
FEATURE                   Location/Qualifiers
source                    1..281
                          mol_type = protein
                          organism = Neisseria meningitidis
SEQUENCE: 3
MNRTAFCCLS LTTALILTAC SSGGGGSGGG GVAADIGTGL ADALTAPLDH KDKGLKSLTL    60
EDSIPQNGTL TLSAQGAEKT FKAGDKDNSL NTGKLKNDKI SRFDFVQKIE VDGQTITLAS   120
GEFQIYKQNH SAVVALQIEK INNPDKTDSL INQRSFLVSG LGGEHTAFNQ LPGGKAEYHG   180
KAFSSDDPNG RLHYSIDFTK KQGYGRIEHL KTLEQNVELA AAELKADEKS HAVILGDTRY   240
GSEEKGTYHL ALFGDRAQEI AGSATVKIGE KVHEIGIAGK Q                       281

SEQ ID NO: 4              moltype = AA  length = 254
FEATURE                   Location/Qualifiers
source                    1..254
                          mol_type = protein
                          organism = Neisseria meningitidis
SEQUENCE: 4
CSSGGGGVAA DIGAGLADAL TAPLDHKDKS LQSLTLDQSV RKNEKLKLAA QGAEKTYGNG    60
DSLNTGKLKN DKVSRFDFIR QIEVDGQLIT LESGEFQIYK QDHSAVVALQ IEKINNPDKI   120
DSLINQRSFL VSGLGGEHTA FNQLPDGKAE YHGKAFSSDD AGGKLTYTID FAAKQGHGKI   180
EHLKTPEQNV ELAAAELKAD EKSHAVILGD TRYGSEEKGT YHLALFGDRA QEIAGSATVK   240
IGEKVHEIGI AGKQ                                                     254

SEQ ID NO: 5              moltype = AA  length = 247
FEATURE                   Location/Qualifiers
source                    1..247
                          mol_type = protein
                          organism = Neisseria meningitidis
SEQUENCE: 5
VAADIGAGLA DALTAPLDHK DKSLQSLTLD QSVRKNEKLK LAAQGAEKTY GNGDSLNTGK    60
LKNDKVSRFD FIRQIEVDGQ LITLESGEFQ IYKQDHSAVV ALQIEKINNP DKIDSLINQR   120
SFLVSGLGGE HTAFNQLPDG KAEYHGKAFS SDDAGGKLTY TIDFAAKQGH GKIEHLKTPE   180
QNVELAAAEL KADEKSHAVI LGDTRYGSEE KGTYHLALFG DRAQEIAGSA TVKIGEKVHE   240
IGIAGKQ                                                             247

SEQ ID NO: 6              moltype = AA  length = 488
FEATURE                   Location/Qualifiers
source                    1..488
                          mol_type = protein
                          organism = Neisseria meningitidis
SEQUENCE: 6
MFKRSVIAMA CIFALSACGG GGGGSPDVKS ADTLSKPAAP VVSEKETEAK EDAPQAGSQG    60
QGAPSAQGSQ DMAAVSEENT GNGGAVTADN PKNEDEVAQN DMPQNAAGTD SSTPNHTPDP   120
NMLAGNMENQ ATDAGESSQP ANQPDMANAA DGMQGDDPSA GGQNAGNTAA QGANQAGNNQ   180
AAGSSDPIPA SNPAPANGGS NFGRVDLANG VLIDGPSQNI TLTHCKGDSC SGNNFLDEEV   240
QLKSEFEKLS DADKISNYKK DGKNDKFVGL VADSVQMKGI NQYIIFYKPK PTSFARFRRS   300
ARSRRSLPAE MPLIPVNQAD TLIVDGEAVS LTGHSGNFIA PEGNYRYLTY GAEKLPGGSY   360
ALRVQGEPAK GEMLAGAAVY NGEVLHFHTE NGRPYPTRGR FAAKVDFGSK SVDGIIDSGD   420
DLHMGTQKFK AAIDGNGFKG TWTENGSGDV SGKFYGPAGE EVAGKYSYRP TDAEKGGFGV   480
FAGKKEQD                                                            488

SEQ ID NO: 7              moltype = AA  length = 364
```

```
FEATURE                Location/Qualifiers
source                 1..364
                       mol_type = protein
                       organism = Neisseria meningitidis
SEQUENCE: 7
MSMKHFPSKV LTTAILATFC SGALAATSDD DVKKAATVAI VAAYNNGQEI NGFKAGETIY    60
DIGEDGTITQ KDATAADVEA DDFKGLGLKK VVTNLTKTVN ENKQNVDAKV KAAESEIEKL   120
TTKLADTDAA LADTDAALDE TTNALNKLGE NITTFAEETK TNIVKIDEKL EAVADTVDKH   180
AEAFNDIADS LDETNTKADE AVKTANEAKQ TAEETKQNVD AKVKAAETAA GKAEAAAGTA   240
NTAADKAEAV AAKVTDIKAD IATNKADIAK NSARIDSLDK NVANLRKETR QGLAEQAALS   300
GLFQPYNVGR FNVTAAVGGY KSESAVAIGT GFRFTENFAA KAGVAVGTSS GSSAAYHVGV   360
NYEW                                                                364

SEQ ID NO: 8           moltype = AA  length = 174
FEATURE                Location/Qualifiers
source                 1..174
                       mol_type = protein
                       organism = Neisseria meningitidis
SEQUENCE: 8
MKKALATLIA LALPAAALAE GASGFYVQAD AAHAKASSSL GSAKGFSPRI SAGYRINDLR    60
FAVDYTRYKN YKAPSTDFKL YSIGASAIYD FDTQSPVKPY LGARLSLNRA SVDLGGSDSF   120
SQTSIGLGVL TGVSYAVTPN VDLDAGYRYN YIGKVNTVKN VRSGELSAGV RVKF         174

SEQ ID NO: 9           moltype = AA  length = 792
FEATURE                Location/Qualifiers
source                 1..792
                       mol_type = protein
                       organism = Neisseria meningitidis
SEQUENCE: 9
MKPLQMLPIA ALVGSIFGNP VLAADEAATE TTPVKAEIKA VRVKGQRNAP AAVERVNLNR    60
IKQEMIRDNK DLVRYSTDVG LSDSGRHQKG FAVRGVEGNR VGVSIDGVNL PDSEENSLYA   120
RYGNFNSSRL SIDPELVRNI EIVKGADSFN TGSGALGGGV NYQTLQGRDL LLDDRQFGVM   180
MKNGYSTRNR EWTNTLGFGV SNDRVDAALL YSQRRGHETE SAGNRGYAVE GEGSGANIRG   240
SARGIPDSSK HKYNHHALGK IAYQINDNHR IGASLNGQGG HNYTVEESYN LTASSWREAD   300
DVNRRRNANL FYEWMPDSNW LSSLKADFDY QKTKVAAVNN KGSFPMDYST WTRNYNQKDL   360
DEIYNRSMDT RFKRFTLRLD SHPLQLGGGR HRLSFKTFVS RRDFENLNRD DYYFSGRVVR   420
TTSSIQHPVK TTNYGFSLSD QIQWNDVFSS RAGIRYDHTK MTPQELNAEC HACDKTPPAA   480
NTYKGWSGFV GLAAQLNQAW RVGYDITSGY RVPNASEVYF TYNHGSGNWL PNPNLKAERS   540
TTHTLSLQGR SEKGMLDANL YQSNYRNFLS EEQKLTTSGT PGCTEENAYY GICSDPYKEK   600
LDWQMKNIDK ARIRGIELTG RLNVDKVASF VPEGWKLFGS LGYAKSKLSG DNSLLSTQPL   660
KVIAGIDYES PSEKWGVFSR LTYLGAKKVK DAQYTVYENK GWGTPLQKKV KDYPWLNKSA   720
YVFDMYGFYK PAKNLTLRAG VYNLFNRKYT TWDSLRGLYS YSTTNAVDRD GKGLDRYRAP   780
GRNYAVSLEW KF                                                      792

SEQ ID NO: 10          moltype = AA  length = 591
FEATURE                Location/Qualifiers
source                 1..591
                       mol_type = protein
                       organism = Neisseria meningitidis
SEQUENCE: 10
MNKIYRIIWN SALNAWVVVS ELTRNHTKRA SATVKTAVLA TLLFATVQAS ANNEEQEEDL    60
YLDPVQRTVA VLIVNSDKEG TGEKEKVEEN SDWAVYFNEK GVLTAREITL KAGDNLKIKQ   120
NGTNFTYSLK KDLTDLTSVG TEKLSFSANG NKVNITSDTK GLNFAKETAG TNGDTTVHLN   180
GIGSTLTDTL LNTGATTNVT NDNVTDDEKK RAASVKDVLN AGWNIKGVKP GTTASDNVDF   240
VRTYDTVEFL SADTKTTTVN VESKDNGKKT EVKIGAKTSV IKEKDGKLVT GKDKGENGSS   300
TDEGEGLVTA KEVIDAVNKA GWRMKTTTAN GQTGQADKFE TVTSGTNVTF ASGKGTTATV   360
SKDDQGNITV MYDVNVGDAL NVNQLQNSGW NLDSKAVAGS SGKVISGNVS PSKGKMDETV   420
NINAGNNIEI TRNGKNIDIA TSMTPQFSSV SLGAGADAPT LSVDGDALNV GSKKDNKPVR   480
ITNVAPGVKE GDVTNVAQLK GVAQNLNNRI DNVDGNARAG IAQAIATAGL VQAYLPGKSM   540
MAIGGGTYRG EAGYAIGYSS ISDGGNWIIK GTASGNSRGH FGASASVGYQ W            591

SEQ ID NO: 11          moltype = AA  length = 1457
FEATURE                Location/Qualifiers
source                 1..1457
                       mol_type = protein
                       organism = Neisseria meningitidis
SEQUENCE: 11
MKTTDKRTTE THRKAPKTGR IRFSPAYLAI CLSFGILPQA WAGHTYFGIN YQYYRDFAEN    60
KGKFAVGAKD IEVYNKKGEL VGKSMTKAPM IDFSVVSRNG VAALVGDQYI VSVAHNGGYN   120
NVDFGAEGRN PDQHRFTYKI VKRNNYKAGT KGHPYGGDYH MPRLHKFVTD AEPVEMTSYM   180
DGRKYIDQNN YPDRVRIGAG RQYWRSDEDE PNNRESSYHI ASAYSWLVGG NTFAQNGSGG   240
GTVNLGSEKI KHSPYGFLPT GGSFGDSGSP MFIYDAQKQK WLINGVLQTG NPYIGKSNGF   300
QLVRKDWFYD EIFAGDTHSV FYEPRQNGKY SFNDDNNGTG KINAKHEHNS LPNRLKTRTV   360
QLFNVSLSET AREPVYHAAG GVNSYRPRLN NGENISFIDE GKGELILTSN INQGAGGLYF   420
QGDFTVSPEN NETWQGAGVH ISEDSTVTWK VNGVANDRLS KIGKGTLHVQ AKGENQGSIS   480
VGDGTVILDQ QADDKKKQA FSEIGLVSGR GTVQLNADNQ FNPDKLYPGF RGGRLDLNGH   540
SLSFHRIQNT DEGAMIVNHN QDKESTVTIT GNKDIATTGN NNSLDSKKEI AYNGWFGEKD   600
TTKTNGRLNL VYQPAAEDRT LLLSGGTNLN GNITQTNGKL FFSGRPTPHA YNHLNDHWSQ   660
KEGIPRGEIV WDNDWINRTF KAENFQIKGG QAVVSRNVAK VKGDWHLSNH AQAVFGVAPH   720
```

```
QSHTICTRSD WTGLTNCVEK TITDDKVIAS LTKTDISGNV DLADHAHLNL TGLATLNGNL    780
SANGDTRYTV SHNATQNGNL SLVGNAQATF NQATLNGNTS ASGNASFNLS DHAVQNGSLT    840
LSGNAKANVS HSALNGNVSL ADKAVFHFES SRFTGQISGG KDTALHLKDS EWTLPSGTEL    900
GNLNLDNATI TLNSAYRHDA AGAQTGSATD APRRRSRRSR RSLLSVTPPT SVESRFNTLT    960
VNGKLNGQGT FRFMSELFGY RSDKLKLAES SEGTYTLAVN NTGNEPASLE QLTVVEGKDN   1020
KPLSENLNFT LQNEHVDAGA WRYQLIRKDG EFRLHNPVKE QELSDKLGKA EAKKQAEKDN   1080
AQSLDALIAA GRDAVEKTES VAEPARQAGG ENVGIMQAEE EKKRVQADKD TALAKQREAE   1140
TRPATTAFPR ARRARRDLPQ LQPQPQPQPQ RDLISRYANS GLSEFSATLN SVFAVQDELD   1200
RVFAEDRRNA VWTSGIRDTK HYRSQDFRAY RQQTDLRQIG MQKNLGSGRV GILFSHNRTE   1260
NTFDDGIGNS ARLAHGAVFG QYGIDRFYIG ISAGAGFSSG SLSDGIGGKI RRRVLHYGIQ   1320
ARYRAGFGGF GIEPHIGATR YFVQKADYRY ENVNIATPGL AFNRYRAGIK ADYSFKPAQH   1380
ISITPYLSLS YTDAASGKVR TRVNTAVLAQ DFGKTRSAEW GVNAEIKGFT LSLHAAAAKG   1440
PQLEAQHSAG IKLGYRW                                                 1457

SEQ ID NO: 12           moltype = AA  length = 797
FEATURE                 Location/Qualifiers
source                  1..797
                        mol_type = protein
                        organism = Neisseria meningitidis
SEQUENCE: 12
MKLKQIASAL MMLGISPLAL ADFTIQDIRV EGLQRTEPST VFNYLPVKVG DTYNDTHGSA     60
IIKSLYATGF FDDVRVETAD GQLLLTVIER PTIGSLNITG AKMLQNDAIK KNLESFGLAQ    120
SQYFNQATLN QAVAGLKEEY LGRGKLNIQI TPKVTKLARN RVDIDITIDE GKSAKITDIE    180
FEGNQVYSDR KLMRQMSLTE GGIWTWLTRS NQFNEQKFAQ DMEKVTDFYQ NNGYFDFRIL    240
DTDIQTNEDK TKQTIKITVH EGGRFRWGKV SIEGDTNEVP KAELEKLLTM KPGKWYERQQ    300
MTAVLGEIQN RMGSAGYAYS EISVQPLPNA ETKTVDFVLH IEPGRKIYVN EIHITGNNKT    360
RDEVVRRELR QMESAPYDTS KLQRSKERVE LLGYFDNVQF DAVPLAGTPD KVDLNMSLTE    420
RSTGSLDLSA GWVQDTGLVM SAGVSQDNLF GTGKSAALRA SRSKTTLNGS LSFTDPYFTA    480
DGVSLGYDVY GKAFDPRKAS TSIKQYKTTT AGAGIRMSVP VTEYDRVNFG LVAEHLTVNT    540
YNKAPKHYAD FIKKYGKTDG TDGSPFKGWLY KGTVGWGRNK TDSALWPTRG YLTGVNAEIA    600
LPGSKLQYYS ATHNQTWFFP LSKTFTLMLG GEVGIAGGYG RTKEIPFFEN FYGGGLGSVR    660
GYESGTLGPK VYDEYGEKIS YGGNKKANVS AELLFPMPGA KDARTVRLSL FADAGSVWDG    720
KTYDDNSSSA TGGRVQNIYG AGNTHKSTFT NELRYSAGGA VTWLSPLGPM KFSYAYPLKK    780
KPEDEIQRFQ FQLGTTF                                                  797

SEQ ID NO: 13           moltype = AA  length = 180
FEATURE                 Location/Qualifiers
source                  1..180
                        mol_type = protein
                        organism = Neisseria meningitidis
SEQUENCE: 13
MVSAVIGSAA VGAKSAVDRR TTGAQTDDNV MALRIETTAR SYLRQNNQTK GYTPQISVVG     60
YDRHLLLLGQ VATEGEKQFV GQIARSEQAA EGVYNYITVA SLPRTAGDIA GDTWNTSKVR    120
ATLLGISPAT RARVKIVTYG NVTYVMGILT PEEQAQITQK VSTTGVQKV ITLYQNYVQR    180

SEQ ID NO: 14           moltype = AA  length = 644
FEATURE                 Location/Qualifiers
source                  1..644
                        mol_type = protein
                        organism = Neisseria meningitidis
SEQUENCE: 14
MASPDVKSAD TLSKPAAPVV SEKETEAKED APQAGSQGQG APSAQGGQDM AAVSEENTGN     60
GGAAATDKPK NEDEGAQNDM PQNAADTDSL TPNHTPASNM PAGNMENQAP DAGESEQPAN    120
QPDMANTADG MQGDDPSAGG ENAGNTAAQG TNQAENNQTA GSQNPASSTN PSATNSGGDF    180
GRTNVGNSVV IDGPSQNITL THCKGDSCSG NNFLDEEVQL KSEFEKLSDA DKISNYKKDG    240
KNDGKNDKFV GLVADSVQMK GINQYIIFYK PKPTSFARFR RSARSRRSLP AEMPLIPVNQ    300
ADTLIVDGEA VSLTGHSGNI FAPEGNYRYL TYGAEKLPGG SYALRVQGEP SKGEMLAGTA    360
VYNGEVLHFH TENGRPSPSR GRFAAKVDFG SKSVDGIIDS DGLHMGTQK FKAAIDGNGF    420
KGTWTENGGG DVSGKFYGPA GEEVAGKYSY RPTDAEKGGP GVFAGKKEQD GSGGGGATYK    480
VDEYHANARF AIDHFNTSTN VGGFYGLTGS VEFDQAKRDG KIDITIPVAN LQSGSQHFTD    540
HLKSADIFDA AQYPDIRFVS TKFNFNGKKL VSVDGNLTMH GKTAPVKLKA EKFNCYQSPM    600
AKTEVCGGDF STTIDRTKWG VDYLNVGMT KSVRIDIQIE AAKQ                     644

SEQ ID NO: 15           moltype = AA  length = 327
FEATURE                 Location/Qualifiers
source                  1..327
                        mol_type = protein
                        organism = Neisseria meningitidis
SEQUENCE: 15
ATNDDDVKKA ATVAIAAAYN NGQEINGFKA GETIYDIDED GTITKKDATA ADVEADDFKG     60
LGLKKVVTNL TKTVNENKQN VDAKVKAAES EIEKLTTKLA DTDAALADTD AALDATTNAL    120
NKLGENITTF AEETKTNIVK IDEKLEAVAD TVDKHAEAFN DIADSLDETN TKADEAVKTA    180
NEAKQTAEET KQNVDAKVKA AETAAGKAEA AAGTANTAAD KAEAVAAKVT DIKADIATNK    240
DNIAKKANSA DVYTREESDS KFVRIDGLNA TTEKLDTRLA SAEKSIADHD TRLNGLDKTV    300
SDLRKETRQG LAEQAALSGL FQPYNVG                                      327

SEQ ID NO: 16           moltype = AA  length = 248
FEATURE                 Location/Qualifiers
source                  1..248
```

```
                        mol_type = protein
                        organism = Neisseria meningitidis
SEQUENCE: 16
VAADIGAGLA DALTAPLDHK DKGLQSLTLD QSVRKNEKLK LAAQGAEKTY GNGDSLNTGK   60
LKNDKVSRFD FIRQIEVDGQ LITLESGEFQ VYKQSHSALT AFQTEQIQDS EHSGKMVAKR  120
QFRIGDIAGE HTSFDKLPEG GRATYRGTAF GSDDAGGKLT YTIDFAAKQG NGKIEHLKSP  180
ELNVDLAAAD IKPDGKRHAV ISGSVLYNQA EKGSYSLGIF GGKAQEVAGS AEVKTVNGIR  240
HIGLAAKQ                                                          248

SEQ ID NO: 17           moltype = AA  length = 250
FEATURE                 Location/Qualifiers
source                  1..250
                        mol_type = protein
                        organism = Neisseria meningitidis
SEQUENCE: 17
VAADIGTGLA DALTAPLDHK DKGLKSLTLE DSIPQNGTLT LSAQGAEKTF KAGDKDNSLN   60
TGKLKNDKIS RFDFVQKIEV DGQTITLASG EFQIYKQNHS AVVALQIEKI NNPDKTDSLI  120
NQRSFLVSGL GGEHTAFNQL PGGKAEYHGK AFSSDDPNGR LHYSIDFTKK QGYGRIEHLK  180
TLEQNVELAA AELKADEKSH AVILGDTRYG SEEKGTYHLA LFGDRAQEIA GSATVKIGEK  240
VHEIGIAGKQ                                                        250

SEQ ID NO: 18           moltype = AA  length = 273
FEATURE                 Location/Qualifiers
source                  1..273
                        mol_type = protein
                        organism = Neisseria meningitidis
SEQUENCE: 18
MNRTAFCCLS LTAALILTAC SSGGGGVAAD IGAGLADALT APLDHKDKSL QSLTLDQSVR   60
KNEKLKLAAQ GAEKTYGNGD SLNTGKLKND KVSRFDFIRQ IEVDGQLITL ESGEFQIYKQ  120
DHSAVVALQI EKINNPDKID SLINQRSFLV SGLGGEHTAF NQLPDGKAEY HGKAFSSDDA  180
GGKLTYTIDF AAKQGHGKIE HLKTPEQNVE LAAAELKADE KSHAVILGDT RYGSEEKGTY  240
HLALFGDRAQ EIAGSATVKI GEKVRHIGIA GKQ                              273

SEQ ID NO: 19           moltype = AA  length = 273
FEATURE                 Location/Qualifiers
source                  1..273
                        mol_type = protein
                        organism = Neisseria meningitidis
SEQUENCE: 19
MNRTAFCCLS LTAALILTAC SSGGGGVAAD IGAGLADALT APLDHKDKSL QSLTLDQVVR   60
KNEKLKLAAQ GAEKTYGNGD SLNTGKLKND KVSRFDFIRQ IEVDGQLITL ESGEFQIYKQ  120
DHSAVVALQI EKINNPDKID SLINQRSFLV SGLGGEHTAF NQLPDGKAEY HGKAFSSDDA  180
GGKLTYTIDF AAKQGHGKIE HLKTPEQNVE LAAAELKADE KSHAVILGDT RYGSEEKGTY  240
HLALFGDRAQ EIAGSATVKI GEKVRHIGIA GKQ                              273

SEQ ID NO: 20           moltype = AA  length = 273
FEATURE                 Location/Qualifiers
source                  1..273
                        mol_type = protein
                        organism = Neisseria meningitidis
SEQUENCE: 20
MNRTAFCCLS LTAALILTAC SSGGGGVAAD IGAGLADALT APLDHKDKSL QSLTLDQVVR   60
KNEKLKLAAQ GAEKTYGNGD SLNTGKLKND KVSRFDFIRQ IEVDGQLITL ESGEFQIYKQ  120
DHSAVVALQI EKINNPDKID SLINQRSFRV SGLGGEHTAF NQLPDGKAEY HGKAFSSDDA  180
GGKLTYTIDF AAKQGHGKIE HLKTPEQNVE LAAAELKADE KSHAVILGDT RYGSEEKGTY  240
HLALFGDRAQ EIAGSATVKI GEKVHEIGIA GKQ                              273

SEQ ID NO: 21           moltype = AA  length = 273
FEATURE                 Location/Qualifiers
source                  1..273
                        mol_type = protein
                        organism = Neisseria meningitidis
SEQUENCE: 21
MNRTAFCCLS LTAALILTAC SSGGGGVAAD IGAGLADALT APLDHKDKSL QSLTLDQSVR   60
KNEKLKLAAQ GAEKTYGNGD SLNTGKLKND KVSRFDFIRQ IEVDGQLITL ESGEFQIYKQ  120
DHSAVVALQI EKINNPDKID SLINQRSFRV SGLGGEHTAF NQLPDGKAEY HGKAFSSDDA  180
GGKLTYTIDF AAKQGHGKIE HLKTPEQNVE LAAAELKADE KSHAVILGDT RYGSEEKGTY  240
HLALFGDRAQ EIAGSATVKI GEKVHEIGIA GKQ                              273

SEQ ID NO: 22           moltype = AA  length = 273
FEATURE                 Location/Qualifiers
source                  1..273
                        mol_type = protein
                        organism = Neisseria meningitidis
SEQUENCE: 22
MNRTAFCCLS LTAALILTAC SSGGGGVAAD IGAGLADALT APLDHKDKSL QSLTLDQSVR   60
KNEKLKLAAQ GAEKTYGNGD SLNTGKLKND KVSRFDFIRQ IEVDGQLITL ESGEFQIYKQ  120
DHSAVVALQI EKINNPDKID SLINQRSFLV GDLGGEHTAF NQLPDGKAEY HGKAFSSDDA  180
GGKLTYTIDF AAKQGHGKIE HLKTPEQNVE LAAAELKADE KSHAVILGDT RYGSEEKGTY  240
```

-continued

```
HLALFGDRAQ EIAGSATVKI GEKVHEIGIA GKQ                               273

SEQ ID NO: 23            moltype = AA  length = 273
FEATURE                  Location/Qualifiers
source                   1..273
                         mol_type = protein
                         organism = Neisseria meningitidis
SEQUENCE: 23
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVTALQI EKINNPDKID SLINQRSFLV GDLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                               273

SEQ ID NO: 24            moltype = AA  length = 273
FEATURE                  Location/Qualifiers
source                   1..273
                         mol_type = protein
                         organism = Neisseria meningitidis
SEQUENCE: 24
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVVALQI EKINNPDKSD SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                               273

SEQ ID NO: 25            moltype = AA  length = 273
FEATURE                  Location/Qualifiers
source                   1..273
                         mol_type = protein
                         organism = Neisseria meningitidis
SEQUENCE: 25
MNRTAFCCLS LTAALILTAC SSGGGGVAAD IGAGLADALT APLDHKDKSL QSLTLDQSCR    60
KNEKCKLAAQ GAEKTYGNGD SLNTGKLKND KVSRFDFIRQ IEVDGQLITL ESGEFQIYKQ   120
DHSAVVALQI EKINNPDKID SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                               273

SEQ ID NO: 26            moltype = AA  length = 273
FEATURE                  Location/Qualifiers
source                   1..273
                         mol_type = protein
                         organism = Neisseria meningitidis
SEQUENCE: 26
MNRTAFCCLS LTAALILTAC SSGGGGVAAD IGAGLADALT APLDHKDKSL QSLTLDQSVR    60
KNEKLKCAAQ GAEKTYGNGD SLNTGKLKND KVSRCDFIRQ IEVDGQLITL ESGEFQIYKQ   120
DHSAVVALQI EKINNPDKID SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                               273

SEQ ID NO: 27            moltype = AA  length = 273
FEATURE                  Location/Qualifiers
source                   1..273
                         mol_type = protein
                         organism = Neisseria meningitidis
SEQUENCE: 27
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSCLV SGLGGEHTAF NQLPDGKAEY HGKAFSCDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                               273

SEQ ID NO: 28            moltype = AA  length = 273
FEATURE                  Location/Qualifiers
source                   1..273
                         mol_type = protein
                         organism = Neisseria meningitidis
SEQUENCE: 28
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVTALQI EKINNPDKID SLINQRSFLV GDLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVRHIGIA GKQ                               273

SEQ ID NO: 29            moltype = AA  length = 273
FEATURE                  Location/Qualifiers
source                   1..273
                         mol_type = protein
                         organism = Neisseria meningitidis
```

```
SEQUENCE: 29
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSFRI GDIAGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 30           moltype = AA   length = 273
FEATURE                 Location/Qualifiers
source                  1..273
                        mol_type = protein
                        organism = Neisseria meningitidis
SEQUENCE: 30
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVTALQI EKINNPDKID SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 31           moltype = AA   length = 273
FEATURE                 Location/Qualifiers
source                  1..273
                        mol_type = protein
                        organism = Neisseria meningitidis
SEQUENCE: 31
MNRTAFCCLS LTAALILTAC SSGGGGVAAD IGAGLADALT APLDHKDKSL QSLTLDQSVR    60
KNEKLKCAAQ GAEKTYGNGD SLNTGKLKND KVSRFDFIRQ IEVDGQLITL ESGEFQIYKQ   120
DHSAVVALQI EKINNPDKID SLINQRSFLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 32           moltype = AA   length = 273
FEATURE                 Location/Qualifiers
source                  1..273
                        mol_type = protein
                        organism = Neisseria meningitidis
SEQUENCE: 32
MNRTAFCCLS LTAALILTAC SSGGGGVAAD IGAGLADALT APLDHKDKSL QSLTLDQSVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSCLV SGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 33           moltype = AA   length = 273
FEATURE                 Location/Qualifiers
source                  1..273
                        mol_type = protein
                        organism = Neisseria meningitidis
SEQUENCE: 33
MNRTAFCCLS LTAALILTAC SSGGGGVAAD IGAGLADALT APLDHKDKSL QSLTLDQVVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSFLV TGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 34           moltype = AA   length = 273
FEATURE                 Location/Qualifiers
source                  1..273
                        mol_type = protein
                        organism = Neisseria meningitidis
SEQUENCE: 34
MNRTAFCCLS LTAALILTAC SSGGGGVAAD IGAGLADALT APLDHKDKSL QSLTLDQVVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSFRV TGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273

SEQ ID NO: 35           moltype = AA   length = 273
FEATURE                 Location/Qualifiers
source                  1..273
                        mol_type = protein
                        organism = Neisseria meningitidis
SEQUENCE: 35
MNRTAFCCLS LTAALILTAC SSGGGGVAAD IGAGLADALT APLDHKDKSL QSLTLDQVVR    60
KNEKLKLAAQ GAEKTYGNGD SLNTGKLKND KVSRFDFIRQ IEVDGQLITL ESGEFQIYKQ   120
DHSAVVALQI EKINNPDKID SLINQRSFLV GGLGGEHTAF NQLPDGKAEY HGKAFSSDDA   180
GGKLTYTIDF AAKQGHGKIE HLKTPEQNVE LAAAELKADE KSHAVILGDT RYGSEEKGTY   240
HLALFGDRAQ EIAGSATVKI GEKVHEIGIA GKQ                                273
```

| | | |
|---|---|---|
| SEQ ID NO: 36<br>FEATURE<br>source | moltype = AA   length = 273<br>Location/Qualifiers<br>1..273<br>mol_type = protein<br>organism = Neisseria meningitidis | |
| SEQUENCE: 36<br>MNRTAFCCLS LTAALILTAC SSGGGGVAAD IGAGLADALT APLDHKDKSL QSLTLDQVVR<br>KNEKLKLAAQ GAEKTYGNGD SLNTGKLKND KVSRFDFIRQ IEVDGQLITL ESGEFQIYKQ<br>DHSAVVALQI EKINNPDKID SLINQRSFRV GGLGGEHTAF NQLPDGKAEY HGKAFSSDDA<br>GGKLTYTIDF AAKQGHGKIE HLKTPEQNVE LAAAELKADE KSHAVILGDT RYGSEEKGTY<br>HLALFGDRAQ EIAGSATVKI GEKVHEIGIA GKQ | | 60<br>120<br>180<br>240<br>273 |
| SEQ ID NO: 37<br>FEATURE<br>REGION<br><br>source | moltype = AA   length = 11<br>Location/Qualifiers<br>1..11<br>note = N-terminal sequence<br>1..11<br>mol_type = protein<br>organism = synthetic construct | |
| SEQUENCE: 37<br>GPDSDRLQQR R | | 11 |
| SEQ ID NO: 38<br>FEATURE<br>REGION<br><br>source | moltype = AA   length = 7<br>Location/Qualifiers<br>1..7<br>note = N-terminal sequence<br>1..7<br>mol_type = protein<br>organism = synthetic construct | |
| SEQUENCE: 38<br>GSKDISS | | 7 |
| SEQ ID NO: 39<br>FEATURE<br>REGION<br><br>source | moltype = AA   length = 11<br>Location/Qualifiers<br>1..11<br>note = N-terminal sequence<br>1..11<br>mol_type = protein<br>organism = synthetic construct | |
| SEQUENCE: 39<br>GSKDISSGGG G | | 11 |
| SEQ ID NO: 40<br>FEATURE<br>source | moltype = AA   length = 262<br>Location/Qualifiers<br>1..262<br>mol_type = protein<br>organism = Neisseria meningitidis | |
| SEQUENCE: 40<br>CSSGGGGSGG GGVAADIGTG LADALTAPLD HKDKGLKSLT LEDSIPQNGT LTLSAQGAEK<br>TFKAGDKDNS LNTGKLKNDK ISRFDFVQKI EVDGQTITLA SGEFQIYKQN HSAVVALQIE<br>KINNPDKTDS LINQRSFLVS GLGGEHTAFN QLPGGKAEYH GKAFSSDDPN GRLHYSIDFT<br>KKQGYGRIEH LKTLEQNVEL AAAELKADEK SHAVILGDTR YGSEEKGTYH LALFGDRAQE<br>IAGSATVKIG EKVHEIGIAG KQ | | 60<br>120<br>180<br>240<br>262 |
| SEQ ID NO: 41<br>FEATURE<br>source | moltype = AA   length = 250<br>Location/Qualifiers<br>1..250<br>mol_type = protein<br>organism = Neisseria meningitidis | |
| SEQUENCE: 41<br>VAADIGTGLA DALTAPLDHK DKGLKSLTLE DSIPQNGTLT LSAQGAEKTF KAGDKDNSLN<br>TGKLKNDKIS RFDFVQKIEV DGQTITLASG EFQIYKQNHS AVVALQIEKI NNPDKTDSLI<br>NQRSFLVSGL GGEHTAFNQL PGGKAEYHGK AFSSDDPNGR LHYSIDFTKK QGYGRIEHLK<br>TLEQNVELAA AELKADEKSH AVILGDTRYG SEEKGTYHLA LFGDRAQEIA GSATVKIGEK<br>VHAIGIAGKQ | | 60<br>120<br>180<br>240<br>250 |
| SEQ ID NO: 42<br>FEATURE<br>source | moltype = AA   length = 250<br>Location/Qualifiers<br>1..250<br>mol_type = protein<br>organism = Neisseria meningitidis | |
| SEQUENCE: 42<br>VAADIGTGLA DALTAPLDHK DKGLKSLTLE DVIPQNGTLT LSAQGAEKTF KAGDKDNSLN<br>TGKLKNDKIS RFDFVQKIEV DGQTITLASG EFQIYKQNHS AVVALQIEKI NNPDKTDSLI<br>NQRSFLVSGL GGEHTAFNQL PGGKAEYHGK AFSSDDPNGR LHYSIDFTKK QGYGRIEHLK<br>TLEQNVELAA AELKADEKSH AVILGDTRYG SEEKGTYHLA LFGDRAQEIA GSATVKIGEK<br>VHAIGIAGKQ | | 60<br>120<br>180<br>240<br>250 |
| SEQ ID NO: 43 | moltype = AA   length = 250 | |

| FEATURE | Location/Qualifiers |
| --- | --- |
| source | 1..250 |
| | mol_type = protein |
| | organism = Neisseria meningitidis |

SEQUENCE: 43

```
VAADIGTGLA DALTAPLDHK DKGLKSLTLE DVIPQNGTLT LSAQGAEKTF KAGDKDNSLN   60
TGKLKNDKIS RFDFVQKIEV DGQTITLASG EFQIYKQNHS AVVALQIEKI NNPDKTDSLI  120
NQRSFRVSGL GGEHTAFNQL PGGKAEYHGK AFSSDDPNGR LHYSIDFTKK QGYGRIEHLK  180
TLEQNVELAA AELKADEKSH AVILGDTRYG SEEKGTYHLA LFGDRAQEIA GSATVKIGEK  240
VHAIGIAGKQ                                                        250
```

| SEQ ID NO: 44 | moltype = AA length = 250 |
| --- | --- |
| FEATURE | Location/Qualifiers |
| source | 1..250 |
| | mol_type = protein |
| | organism = Neisseria meningitidis |

SEQUENCE: 44

```
VAADIGTGLA DALTAPLDHK DKGLKSLTLE DVIPQNGTLT LSAQGAEKTF KAGDKDNSLN   60
TGKLKNDKIS RFDFVQKIEV DGQTITLASG EFQIYKQNHS AVVALQIEKI NNPDKTDSLI  120
NQRSFRVSGL GGEHTAFNQL PGGKAEYHGK AFSSDDPNGR LHYSIDFTKK QGYGRIEHLK  180
TLEQNVELAA AELKADEKSH AVILGDTRYG SEEKGTYHLA LFGDRAQEIA GSATVKIGEK  240
VHEIGIAGKQ                                                        250
```

| SEQ ID NO: 45 | moltype = AA length = 247 |
| --- | --- |
| FEATURE | Location/Qualifiers |
| source | 1..247 |
| | mol_type = protein |
| | organism = Neisseria meningitidis |

SEQUENCE: 45

```
VAADIGAGLA DALTAPLDHK DKSLQSLTLD QVVRKNEKLK LAAQGAEKTY GNGDSLNTGK   60
LKNDKVSRFD FIRQIEVDGQ LITLESGEFQ IYKQDHSAVV ALQIEKINNP DKIDSLINQR  120
SFRVSGLGGE HTAFNQLPDG KAEYHGKAFS SDDAGGKLTY TIDFAAKQGH GKIEHLKTPE  180
QNVELAAAEL KADEKSHAVI LGDTRYGSEE KGTYHLALFG DRAQEIAGSA TVKIGEKVHE  240
IGIAGKQ                                                           247
```

| SEQ ID NO: 46 | moltype = AA length = 255 |
| --- | --- |
| FEATURE | Location/Qualifiers |
| source | 1..255 |
| | mol_type = protein |
| | organism = Neisseria meningitidis |

SEQUENCE: 46

```
CSSGGGGVAA DIGAGLADAL TAPLDHKDKG LQSLTLDQSV RKNEKLKLAA QGAEKTYGNG   60
DSLNTGKLKN DKVSRFDFIR QIEVDGQLIT LESGEFQVYK QSHSALTAFQ TEQIQDSEHS  120
GKMVAKRQFR IGDIAGEHTS FDKLPEGGRA TYRGTAFGSD DAGGKLTYTI DFAAKQGNGK  180
IEHLKSPELN VDLAAADIKP DGKRHAVISG SVLYNQAEKG SYSLGIFGGK AQEVAGSAEV  240
KTVNGIRHIG LAAKQ                                                  255
```

| SEQ ID NO: 47 | moltype = AA length = 757 |
| --- | --- |
| FEATURE | Location/Qualifiers |
| REGION | 1..757 |
| | note = v2-v3-v1 mutant fusion |
| source | 1..757 |
| | mol_type = protein |
| | organism = synthetic construct |

SEQUENCE: 47

```
VAADIGAGLA DALTAPLDHK DKSLQSLTLD QVVRKNEKLK LAAQGAEKTY GNGDSLNTGK   60
LKNDKVSRFD FIRQIEVDGQ LITLESGEFQ IYKQDHSAVV ALQIEKINNP DKIDSLINQR  120
SFRVSGLGGE HTAFNQLPDG KAEYHGKAFS SDDAGGKLTY TIDFAAKQGH GKIEHLKTPE  180
QNVELAAAEL KADEKSHAVI LGDTRYGSEE KGTYHLALFG DRAQEIAGSA TVKIGEKVHE  240
IGIAGKQGSG GGGVAADIGT GLADALTAPL DHKDKGLKSL TLEDVIPQNG TLTLSAQGAE  300
KTFKAGDKDN SLNTGKLKND KISRFDFVQK IEVDGQTITL ASGEFQIYKQ NHSAVVALQI  360
EKINNPDKTD SLINQRSFRV SGLGGEHTAF NQLPGGKAEY HGKAFSSDDP NGRLHYSIDF  420
TKKQGYGRIE HLKTLEQNVE LAAAELKADE KSHAVILGDT RYGSEEKGTY HLALFGDRAQ  480
EIAGSATVKI GEKVHEIGIA GKQGSGGGGV AADIGAGLAD ALTAPLDHKD KGLQSLTLDQ  540
SVSKNEKLKL AAQGAEKTYG NGDSLNTGKL KNDKVSRFDF IRQIEVDGQL ITLESGEFQV  600
YKQSHSALTA FQTEQIQDSE HSGKMVAKRQ FRIGDIAGEH TSFDKLPEGG RATYRGTAFG  660
SDDAGGKLTY TIDFAAKQGN GKIEHLKSPE LNVDLAAADI KPDGKRHAVI SGSVLYNQAE  720
KGSYSLGIFG GKAQEVAGSA EVKTVNGIRH IGLAAKQ                          757
```

| SEQ ID NO: 48 | moltype = AA length = 769 |
| --- | --- |
| FEATURE | Location/Qualifiers |
| REGION | 1..769 |
| | note = v2-v3-v1 mutant fusion |
| source | 1..769 |
| | mol_type = protein |
| | organism = synthetic construct |

SEQUENCE: 48

```
MGPDSDRLQQ RRVAADIGAG LADALTAPLD HKDKSLQSLT LDQVVRKNEK LKLAAQGAEK   60
TYGNGDSLNT GKLKNDKVSR FDFIRQIEVD GQLITLESGE FQIYKQDHSA VVALQIEKIN  120
```

```
NPDKIDSLIN QRSFRVSGLG GEHTAFNQLP DGKAEYHGKA FSSDDAGGKL TYTIDFAAKQ    180
GHGKIEHLKT PEQNVELAAA ELKADEKSHA VILGDTRYGS EEKGTYHLAL FGDRAQEIAG    240
SATVKIGEKV HEIGIAGKQG SGGGGVAADI GTGLADALTA PLDHKDKGLK SLTLEDVIPQ    300
NGTLTLSAQG AEKTFKAGDK DNSLNTGKLK NDKISRFDFV QKIEVDGQTI TLASGEFQIY    360
KQNHSAVVAL QIEKINNPDK TDSLINQRSF RVSGLGGKA EYHGKAFSSD                420
DPNGRLHYSI DFTKKQGYGR IEHLKTLEQN VELAAAELKA DEKSHAVILG DTRYGSEEKG    480
TYHLALFGDR AQEIAGSATV KIGEKVHEIG IAGKQGSGGG GVAADIGAGL ADALTAPLDH    540
KDKGLQSLTL DQSVSKNEKL KLAAQGAEKT YGNGDSLNTG KLKNDKVSRF DFIRQIEVDG    600
QLITLESGEF QVYKQSHSAL TAFQTEQIQD SEHSGKMVAK RQFRIGDIAG EHTSFDKLPE    660
GGRATYRGTA FGSDDAGGKL TYTIDFAAKQ GNGKIEHLKS PELNVDLAAA DIKPDGKRHA    720
VISGSVLYNQ AEKGSYSLGI FGGKAQEVAG SAEVKTVNGI RHIGLAAKQ                769

SEQ ID NO: 49         moltype = AA  length = 248
FEATURE               Location/Qualifiers
source                1..248
                      mol_type = protein
                      organism = Neisseria meningitidis
SEQUENCE: 49
VAADIGAGLA DALTAPLDHK DKGLQSLTLD QSVSKNEKLK LAAQGAEKTY GNGDSLNTGK     60
LKNDKVSRFD FIRQIEVDGQ LITLESGEFQ VYKQSHSALT AFQTEQIQDS EHSGKMVAKR    120
QFRIGDIAGE HTSFDKLPEG GRATYRGTAF GSDDAGGKLT YTIDFAAKQG NGKIEHLKSP    180
ELNVDLAAAD IKPDGKRHAV ISGSVLYNQA EKGSYSLGIF GGKAQEVAGS AEVKTVNGIR    240
HIGLAAKQ                                                            248

SEQ ID NO: 50         moltype = AA  length = 6
FEATURE               Location/Qualifiers
REGION                1..6
                      note = Linker
source                1..6
                      mol_type = protein
                      organism = synthetic construct
SEQUENCE: 50
GSGGGG                                                                6

SEQ ID NO: 51         moltype = AA  length = 247
FEATURE               Location/Qualifiers
source                1..247
                      mol_type = protein
                      organism = Neisseria meningitidis
SEQUENCE: 51
VAADIGARLA DALTAPLDHK DKSLQSLTLD QSVRKNEKLK LAAQGAEKTY GNGDSLNTGK     60
LKNDKVSRFD FIRQIEVDGQ LITLESGEFQ IYKQDHSAVV ALQIEKINNP DKIDSLINQR    120
SFLVSGLGGE HTAFNQLPDG KAEYHGKAFS SDDAGGKLTY TIDFAAKQGH GKIEHLKTPE    180
QNVELAAAEL KADEKSHAVI LGDTRYGSEE KGTYHLALFG DRAQEIAGSA TVKIGEKVHE    240
IGIAGKQ                                                             247

SEQ ID NO: 52         moltype = AA  length = 248
FEATURE               Location/Qualifiers
source                1..248
                      mol_type = protein
                      organism = Neisseria meningitidis
SEQUENCE: 52
VAADIGAGLA DALTAPLDHK DKGLQSLTLD QSVRKNEKLK LAAQGAEKTY GNGDSLNTGK     60
LKNDKVSRFD FIRQIEVDGK LITLESGEFQ VYKQSHSALT ALQTEQVQDS EDSGKMVAKR    120
QFRIGDIAGE HTSFDKLPKG GSATYRGTAF GSDDAGGKLT YTIDFAAKQG HGKIEHLKSP    180
ELNVELATAE LKADEKSHAV ILGDTRYGGE EKGTYHLALF GDRAQEIAGS ATVKIREKVH    240
EIGIAGKQ                                                            248

SEQ ID NO: 53         moltype = AA  length = 250
FEATURE               Location/Qualifiers
source                1..250
                      mol_type = protein
                      organism = Neisseria meningitidis
SEQUENCE: 53
VAADIGTGLA DALTAPLDHK DKGLKSLTLE DSIPQNGTLT LSAQGAEKTF KAGDKDNSLN     60
TGKLKNDKIS RFDFVQKIEV DGQTITLASG EFQIYKQNHS AVVALQIEKI NNPDKTDSLI    120
NQRSFRVSGL GGEHTAFNQL PGGKAEYHGK AFSSDDPNGR LHYSIDFTKK QGYGRIEHLK    180
TLEQNVELAA AELKADEKSH AVILGDTRYG SEEKGTYHLA LFGDRAQEIA GSATVKIGEK    240
VHEIGIAGKQ                                                          250

SEQ ID NO: 54         moltype = AA  length = 273
FEATURE               Location/Qualifiers
source                1..273
                      mol_type = protein
                      organism = Neisseria meningitidis
SEQUENCE: 54
MNRTAFCCLS LTTALILTAC SSGGGGVAAD IGARLADALT APLDHKDKSL QSLTLDQSVR     60
KNEKLKLAAQ GAEKTYGNGD SLNTGKLKND KVSRFDFIRQ IEVDGQLITL ESGEFQIYKQ    120
DHSAVVALQI EKINNPDKID SLINQRSFLV SGLGGEHTAF NQLPDGKAEY HGKAFSSDDA    180
```

```
GGKLTYTIDF AAKQGHGKIE HLKTPEQNVE LAAAELKADE KSHAVILGDT RYGSEEKGTY    240
HLALFGDRAQ EIAGSATVKI GEKVHEIGIA GKQ                                 273

SEQ ID NO: 55          moltype = AA  length = 247
FEATURE                Location/Qualifiers
source                 1..247
                       mol_type = protein
                       organism = Neisseria meningitidis
SEQUENCE: 55
VAADIGARLA DALTAPLDHK DKSLQSLTLD QSVRKNEKLK LAAQGAEKTY GNGDSLNTGK    60
LKNDKVSRFD FIRQIEVDGQ LITLESGEFQ IYKQDHSAVV ALQIEKINNP DKIDSLINQR    120
SFLVSGLGGE HTAFNQLPDG KAEYHGKAFS SDDAGGKLTY TIDFAAKQGH GKIEHLKTPE    180
QNVELAAAEL KADEKSHAVI LGDTRYGSEE KGTYHLALFG DRAQEIAGSA TVKIGEKVHE    240
IGIAGKQ                                                              247

SEQ ID NO: 56          moltype = AA  length = 247
FEATURE                Location/Qualifiers
source                 1..247
                       mol_type = protein
                       organism = Neisseria meningitidis
SEQUENCE: 56
VAADIGAGLA DALTAPLDHK DKSLQSLTLD QSVRKNEKLK LAAQGAEKTY GNGDSLNTGK    60
LKNDKVSRFD FIRQIEVDGQ LITLESGEFQ IYKQDHSAVV ALQIEKINNP DKIDSLINQR    120
SFLVSGLGGE HTAFNQLPDG KAEYHGKAFS SDDAGGKLTY TIDFAAKQGH GKIEHLKTPE    180
QNVELAAAEL KADEKSHAVI LGDTRYGSEE KGTYHLALFG DRAQEIAGSA TVKIGEKVHA    240
IGIAGKQ                                                              247

SEQ ID NO: 57          moltype = AA  length = 247
FEATURE                Location/Qualifiers
source                 1..247
                       mol_type = protein
                       organism = Neisseria meningitidis
SEQUENCE: 57
VAADIGAGLA DALTAPLDHK DKSLQSLTLD QVVRKNEKLK LAAQGAEKTY GNGDSLNTGK    60
LKNDKVSRFD FIRQIEVDGQ LITLESGEFQ IYKQDHSAVV ALQIEKINNP DKIDSLINQR    120
SFRVSGLGGE HTAFNQLPDG KAEYHGKAFS SDDAGGKLTY TIDFAAKQGH GKIEHLKTPE    180
QNVELAAAEL KADEKSHAVI LGDTRYGSEE KGTYHLALFG DRAQEIAGSA TVKIGEKVHA    240
IGIAGKQ                                                              247

SEQ ID NO: 58          moltype = AA  length = 247
FEATURE                Location/Qualifiers
source                 1..247
                       mol_type = protein
                       organism = Neisseria meningitidis
SEQUENCE: 58
VAADIGAGLA DALTAPLDHK DKSLQSLTLD QVVRKNEKLK LAAQGAEKTY GNGDSLNTGK    60
LKNDKVSRFD FIRQIEVDGQ LITLESGEFQ IYKQDHSAVV ALQIEKINNP DKIDSLINQR    120
SFRIGDIAGE HTAFNQLPDG KAEYHGKAFS SDDAGGKLTY TIDFAAKQGH GKIEHLKTPE    180
QNVELAAAEL KADEKSHAVI LGDTRYGSEE KGTYHLALFG DRAQEIAGSA TVKIGEKVHE    240
IGIAGKQ                                                              247

SEQ ID NO: 59          moltype = AA  length = 254
FEATURE                Location/Qualifiers
source                 1..254
                       mol_type = protein
                       organism = Neisseria meningitidis
SEQUENCE: 59
CSSGGGGVAA DIGARLADAL TAPLDHKDKS LQSLTLDQSV RKNEKLKLAA QGAEKTYGNG    60
DSLNTGKLKN DKVSRFDFIR QIEVDGQLIT LESGEFQIYK QDHSAVVALQ IEKINNPDKI    120
DSLINQRSFR VSGLGGEHTA FNQLPDGKAE YHGKAFSSDD AGGKLTYTID FAAKQGHGKI    180
EHLKTPEQNV ELAAAELKAD EKSHAVILGD TRYGSEEKGT YHLALFGDRA QEIAGSATVK    240
IGEKVHEIGI AGKQ                                                      254

SEQ ID NO: 60          moltype = AA  length = 254
FEATURE                Location/Qualifiers
source                 1..254
                       mol_type = protein
                       organism = Neisseria meningitidis
SEQUENCE: 60
CSSGGGGVAA DIGARLADAL TAPLDHKDKS LQSLTLDQVV RKNEKLKLAA QGAEKTYGNG    60
DSLNTGKLKN DKVSRFDFIR QIEVDGQLIT LESGEFQIYK QDHSAVVALQ IEKINNPDKI    120
DSLINQRSFR VSGLGGEHTA FNQLPDGKAE YHGKAFSSDD AGGKLTYTID FAAKQGHGKI    180
EHLKTPEQNV ELAAAELKAD EKSHAVILGD TRYGSEEKGT YHLALFGDRA QEIAGSATVK    240
IGEKVHEIGI AGKQ                                                      254

SEQ ID NO: 61          moltype = AA  length = 250
FEATURE                Location/Qualifiers
source                 1..250
                       mol_type = protein
```

-continued

```
organism = Neisseria meningitidis
SEQUENCE: 61
VAADIGTGLA DALTAPLDHK DKGLKSLTLE DVIPQNGTLT LSAQGAEKTF KAGDKDNSLN    60
TGKLKNDKIS RFDFVQKIEV DGQTITLASG EFQIYKQNHS AVVALQIEKI NNPDKTDSLI   120
NQRSFRVSGL GGEHTAFNQL PGGKAEYHGK AFSSDDPNGR LHYSIDFTKK QGYGRIEHLK   180
TLEQNVELAA AELKADEKSH AVILGDTRYG SEEKGTYHLA LFGDRAQEIA GSATVKIGEK   240
VHEIGIAGKQ                                                         250
```